US012622898B2

(12) United States Patent
Zhao

(10) Patent No.: US 12,622,898 B2
(45) Date of Patent: May 12, 2026

(54) METHODS AND COMPOSITIONS FOR IMPROVING BONE MARROW HEMATOPOIETIC FUNCTIONS

(71) Applicant: SUN YAT-SEN UNIVERSITY, Guangzhou (CN)

(72) Inventor: Meng Zhao, Guangzhou (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 1060 days.

(21) Appl. No.: 17/769,672

(22) PCT Filed: Oct. 16, 2020

(86) PCT No.: PCT/CN2020/121570
§ 371 (c)(1),
(2) Date: Apr. 15, 2022

(87) PCT Pub. No.: WO2021/073610
PCT Pub. Date: Apr. 22, 2021

(65) Prior Publication Data
US 2024/0165090 A1 May 23, 2024

(30) Foreign Application Priority Data
Oct. 18, 2019 (WO) ................ PCT/CN2019/112050

(51) Int. Cl.
*A61K 31/4409* (2006.01)
*A61P 7/00* (2006.01)

(52) U.S. Cl.
CPC ............ *A61K 31/4409* (2013.01); *A61P 7/00* (2018.01)

(58) Field of Classification Search
CPC ...... A61K 31/685; A61K 31/4409; A61P 7/00
See application file for complete search history.

(56) References Cited

U.S. PATENT DOCUMENTS 11,826,356 B2 * 11/2023 Zhao .................. A61K 31/4409

FOREIGN PATENT DOCUMENTS

| | | |
|---|---|---|
| CN | 108670969 A | 10/2018 |
| CN | 109172574 A | 1/2019 |
| CN | 110051839 A | 7/2019 |

OTHER PUBLICATIONS

French (Journal of Pharmacology and Experimental Therapeutics vol. 333 pp. 129-139. Published 2010) (Year: 2010).*
To (Blood vol. 118 pp. 4530-4540 published 2011) (Year: 2011).*
Adamiak (Oncotarget vol. 8 pp. 65588-65600. Published online Jul. 24, 2017) (Year: 2017).*
De Haan (Blood vol. 131 pp. 479-481 published 2018) (Year: 2018).*
PCT/CN2020/121570 International Search Report dated Jan. 18, 2021.
Adamiak, M., et al., Mobilization studies in mice deficient in sphingosine kinase 2 support a crucial role of the plasma level of spinghosine-1-phosphate in the egress of hematopoietic stem progenitor cells; Oncotarget, vol. 8, No. 39, pp. 65588-65600 Jul. 24, 2017.
Cui, L.Z., et al., Overexpression of PDK2 and PDK3 reflects poor prognosis in acute myeloid leukemia, Cancer Gene Therapy, vol. 27, pp. 15-21, Dec. 2018.
Takubo, K., et al., Regulation of Glycolysis by Pdk Functions as a Metabolic Checkpoint for Cell Cycle Quiescence in Hematopoietic Stem Cells, Cell Stem Cell, vol. 12, pp. 49-61, Jan. 2013.

* cited by examiner

*Primary Examiner* — George W Kosturko
(74) *Attorney, Agent, or Firm* — Sughrue Mion, PLLC

(57) ABSTRACT

The present application provides methods and compositions for treating diseases or disorders related to hematopoietic dysfunctions and/or injuries, or for rejuvenating HSPCs.

8 Claims, 27 Drawing Sheets

Specification includes a Sequence Listing.

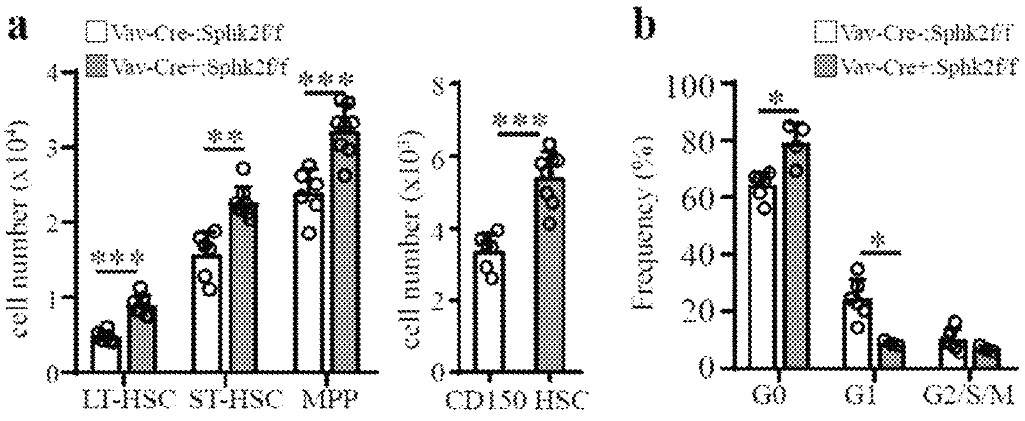
FIG.7
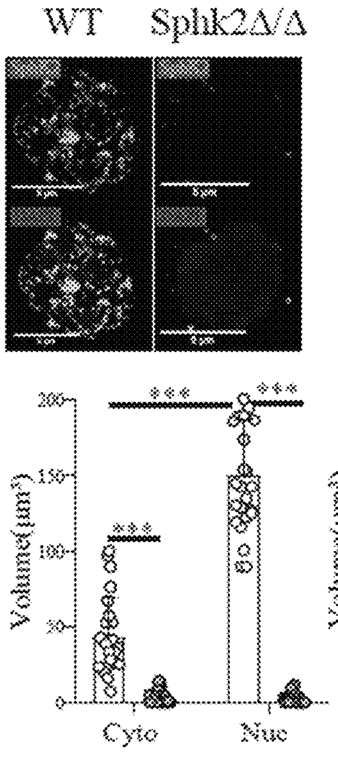
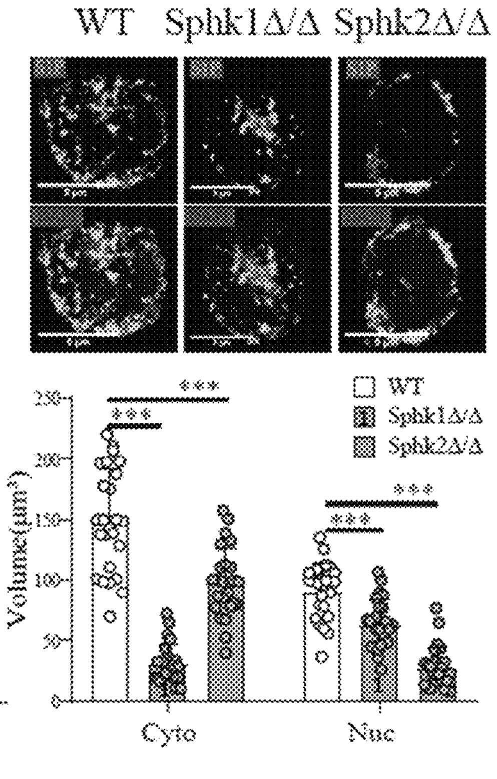
FIG.8
FIG.9

METHODS AND COMPOSITIONS FOR IMPROVING BONE MARROW HEMATOPOIETIC FUNCTIONS

CROSS REFERENCE TO RELATED APPLICATIONS

This application is a National Stage Application and claims priority under 35 U.S.C. § 371 to Patent Cooperation Treaty application PCT/CN2020/121570, filed Oct. 16, 2020, which claims the benefit of Patent Cooperation Treaty application PCT/CN2019/112050 filed Oct. 18, 2019. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022-04-15_262790-509361_ST25", is 528 bytes in size and was created on Apr. 15, 2022, and filed electronically herewith.

FIELD OF THE INVENTION

The present application relates to methods and compositions for improving the functions of hematopoietic system, such as methods and compositions for enhancing and/or rejuvenating the hematopoietic functions.

BACKGROUND

Hematopoietic stem and progenitor cells (HSPC) are a group of primitive hematopoietic cells existing in hematopoietic tissues, and mainly serve to differentiate to produce various blood cells, such as red blood cells, platelets and white blood cells, to support the renewal of hematopoietic and immune systems of the body. HSPCs play an important role in the maintenance and post-injury repair of normal hematopoietic function of the body. Primary lesions, radiation from the environment, and chemical drugs and radiation in clinical treatment can all cause serious injuries to hematopoietic stem and progenitor cells, resulting in hematopoiesis dysfunction, poor hemogram index, white blood cell decrease, immune dysfunction, and even survival rate reduction in the patients. Therefore, to expand hematopoietic stem cell number and/or improve the hematopoietic function of hematopoietic stem cells is crucial to the treatment of hematopoiesis dysfunction and related diseases. Improving the hematopoietic stem cell number and function is also critical for accelerating hematopoiesis reconstitution for patient subjected to bone marrow transplantation.

Further, during the process of aging, HSPCs gradually lose their self-renewal and regenerative potential, whereas the occurrence of cellular derailment strongly increases. Aged HSPCs may also be more susceptible to malignant transformation, leading to various disease and disorders. Aged HSCs also have reduced capacity to generate lymphocytes, which leads to comprised immune capacity during aging.

However, currently, there are very limited therapeutic interventions that are effective in expanding hematopoietic stem cell number and/or improving their functions. There are also very limited interventions that might be useful in preventing or delaying the HSPC aging process, let alone reversing the HSPC aging process or rejuvenating aged HSPCs.

SUMMARY

The present application relates to methods, systems and compositions for preventing, treating and/or alleviating diseases or disorders of the hematopoietic system, such as those related to hematopoietic dysfunctions and hematopoietic injury. The present application also provides methods, systems and compositions for improving the hematopoietic function of hematopoietic stem cells, for promoting hematopoietic recovery after bone marrow transplantation, and/or for rejuvenating hematopoietic stem and progenitor cells. The method, system and composition of the present application may involve attenuating an expression and/or function of Sphk2, and/or enhancing an expression and/or function of Pdk3.

Further, the present application relates to methods and systems for screening candidate agents for treating diseases or disorders related to hematopoietic dysfunction and/or hematopoietic stem cell injury, and/or for rejuvenating aged hematopoietic stem and progenitor cells. Such methods and systems may involve evaluating an effect of the candidate agent in attenuating an expression and/or function of Sphk2, and/or in enhancing an expression and/or function of Pdk3.

In one aspect, the present application provides a method for preventing, treating and/or alleviating a disease or disorder related to hematopoietic dysfunction and/or hematopoietic injury in a subject in need thereof.

In some embodiments, the method comprises attenuating an expression and/or function of Sphk2 in the subject.

In some embodiments, the method comprises attenuating an expression and/or function of Sphk2 in a hematopoietic stem cell and/or progenitor cell (HSPC) in the subject.

In some embodiments, the method comprises administering to the subject an HSPC, wherein an expression and/or function of Sphk2 of the HSPC is attenuated.

In some embodiments, the method comprises administering to the subject an HSPC derived from a donor, wherein the donor has attenuated expression and/or function of Sphk2.

In some embodiments, the method comprises enhancing an expression and/or function of Pdk3 in the subject.

In some embodiments, the method comprises enhancing an expression and/or function of Pdk3 in a hematopoietic stem cell and/or progenitor cell (HSPC) in the subject.

In some embodiments, the method comprises administering to the subject an HSPC, wherein an expression and/or function of Pdk3 of the HSPC is enhanced.

In some embodiments, the method comprises administering to the subject an HSPC derived from a donor, wherein the donor has enhanced expression and/or function of Pdk3.

In another aspect, the present application provides use of an agent capable of attenuating an expression and/or function of Sphk2 in the preparation or manufacture of a medicament, wherein the medicament is for preventing, treating and/or alleviating a disease or disorder related to hematopoietic dysfunction and/or hematopoietic injury in a subject in need thereof.

In another aspect, the present application provides an agent capable of attenuating an expression and/or function of Sphk2, for the use of preventing, treating and/or alleviating a disease or disorder related to hematopoietic dysfunction and/or hematopoietic injury in a subject in need thereof.

In another aspect, the present application provides use of an HSPC in the preparation or manufacture of a medicament, wherein an expression and/or function of Sphk2 of the HSPC is attenuated, and wherein the medicament is for preventing, treating and/or alleviating a disease or disorder related to hematopoietic dysfunction and/or hematopoietic injury in a subject in need thereof.

In another aspect, the present application provides use of an HSPC in the preparation or manufacture of a medicament, wherein the HSPC is derived from a donor having attenuated expression and/or function of Sphk2, and wherein the medicament is for preventing, treating and/or alleviating a disease or disorder related to hematopoietic dysfunction and/or hematopoietic injury in a subject in need thereof.

In another aspect, the present application provides an HSPC having attenuated expression and/or function of Sphk2, for the use of preventing, treating and/or alleviating a disease or disorder related to hematopoietic dysfunction and/or hematopoietic injury in a subject in need thereof.

In another aspect, the present application provides an HSPC derived from a donor having attenuated expression and/or function of Sphk2, for the use of preventing, treating and/or alleviating a disease or disorder related to hematopoietic dysfunction and/or hematopoietic injury in a subject in need thereof.

In another aspect, the present application provides use of an agent capable of enhancing an expression and/or function of Pdk3 in the preparation or manufacture of a medicament, wherein the medicament is for preventing, treating and/or alleviating a disease or disorder related to hematopoietic dysfunction and/or hematopoietic injury in a subject in need thereof.

In another aspect, the present application provides an agent capable of enhancing an expression and/or function of Pdk3, for the use of preventing, treating and/or alleviating a disease or disorder related to hematopoietic dysfunction and/or hematopoietic injury in a subject in need thereof.

In another aspect, the present application provides use of an HSPC in the preparation or manufacture of a medicament, wherein an expression and/or function of Pdk3 of the HSPC is enhanced, and wherein the medicament is for preventing, treating and/or alleviating a disease or disorder related to hematopoietic dysfunction and/or hematopoietic injury in a subject in need thereof.

In another aspect, the present application provides use of an HSPC in the preparation or manufacture of a medicament, wherein the HSPC is derived from a donor having enhanced expression and/or function of Pdk3, and wherein the medicament is for preventing, treating and/or alleviating a disease or disorder related to hematopoietic dysfunction and/or hematopoietic injury in a subject in need thereof.

In another aspect, the present application provides an HSPC having enhanced expression and/or function of Pdk3, for the use of preventing, treating and/or alleviating a disease or disorder related to hematopoietic dysfunction and/or hematopoietic injury in a subject in need thereof.

In another aspect, the present application provides an HSPC derived from a donor having enhanced expression and/or function of Pdk3, for the use of preventing, treating and/or alleviating a disease or disorder related to hematopoietic dysfunction and/or hematopoietic injury in a subject in need thereof.

In some embodiments, the disease or disorder related to hematopoietic dysfunction and/or hematopoietic injury comprises poor hemogram index, reduction of immune cells, reduction of white blood cells, reduction of platelets, and/or a bone marrow failure syndrome.

In some embodiments, the disease or disorder is primary or of primary origin.

In some embodiments, the disease or disorder is related to and/or caused by radiation or a therapy-induced injury.

In some embodiments, the therapy-induced injury comprises a radiotherapy-induced injury and/or a chemotherapy-induced injury.

In some embodiments, the chemotherapy comprises 5-fluorouracil.

In one aspect, the present application provides a method for increasing hematopoietic cell expansion in a subject in need thereof.

In some embodiments, the method comprises attenuating an expression and/or function of Sphk2 in the subject.

In some embodiments, the method comprises enhancing an expression and/or function of Pdk3 in the subject.

In some embodiments, the method comprises attenuating an expression and/or function of Sphk2 in an HSPC in the subject.

In some embodiments, the method comprises enhancing an expression and/or function of Pdk3 in an HSPC in the subject.

In one aspect, the present application provides use of an agent capable of attenuating an expression and/or function of Sphk2 in the preparation or manufacture of a composition for increasing hematopoietic cell expansion in a subject in need thereof.

In one aspect, the present application provides an agent capable of attenuating an expression and/or function of Sphk2, for the use of increasing hematopoietic cell expansion in a subject in need thereof.

In one aspect, the present application provides use of an HSPC in the preparation or manufacture of a composition for increasing hematopoietic cell expansion in a subject in need thereof, wherein an expression and/or function of Sphk2 of the HSPC is attenuated.

In one aspect, the present application provides use of an HSPC in the preparation or manufacture of a composition for increasing hematopoietic cell expansion in a subject in need thereof, wherein the HSPC is derived from a donor having attenuated expression and/or function of Sphk2.

In one aspect, the present application provides an HSPC having attenuated expression and/or function of Sphk2, for the use of increasing hematopoietic cell expansion in a subject in need thereof.

In one aspect, the present application provides an HSPC derived from a donor having attenuated expression and/or function of Sphk2, for the use of increasing hematopoietic cell expansion in a subject in need thereof.

In one aspect, the present application provides use of an agent capable of enhancing an expression and/or function of Pdk3 in the preparation or manufacture of a composition for increasing hematopoietic cell expansion in a subject in need thereof.

In one aspect, the present application provides an agent capable of enhancing an expression and/or function of Pdk3, for the use of increasing hematopoietic cell expansion in a subject in need thereof.

In one aspect, the present application provides use of an HSPC in the preparation or manufacture of a composition for increasing hematopoietic cell expansion in a subject in need thereof, wherein an expression and/or function of Pdk3 of the HSPC is enhanced.

In one aspect, the present application provides use of an HSPC in the preparation or manufacture of a composition for increasing hematopoietic cell expansion in a subject in need thereof, wherein the HSPC is derived from a donor having enhanced expression and/or function of Pdk3.

In one aspect, the present application provides an HSPC having enhanced expression and/or function of Pdk3, for the use of increasing hematopoietic cell expansion in a subject in need thereof.

In one aspect, the present application provides an HSPC derived from a donor having enhanced expression and/or function of Pdk3, for the use of increasing hematopoietic cell expansion in a subject in need thereof.

In some embodiments, the HSPC is a bone marrow derived HSPC.

In one aspect, the present application provides a method for promoting hematopoietic recovery after bone marrow transplantation in a subject in need thereof.

In some embodiments, the method comprises attenuating an expression and/or function of Sphk2 in the subject. In some embodiments, the expression and/or function of Sphk2 is attenuated in the subject after the bone marrow transplantation.

In some embodiments, the method comprises enhancing an expression and/or function of Pdk3 in the subject. In some embodiments, the expression and/or function of Pdk3 is enhanced in the subject after the bone marrow transplantation.

In some embodiments, the method comprises attenuating an expression and/or function of Sphk2 in an HSPC of the bone marrow being transplanted.

In some embodiments, the method comprises enhancing an expression and/or function of Pdk3 in an HSPC of the bone marrow being transplanted.

In some embodiments, the bone marrow is derived from a donor having attenuated expression and/or function of Sphk2.

In some embodiments, the bone marrow is derived from a donor having enhanced expression and/or function of Pdk3.

In some embodiments, the transplanted bone marrow comprises an HSPC with attenuated expression and/or function of Sphk2.

In some embodiments, the transplanted bone marrow comprises an HSPC with enhanced expression and/or function of Pdk3.

In one aspect, the present application provides use of an agent capable of attenuating an expression and/or function of Sphk2 in the preparation or manufacture of a composition for promoting hematopoietic recovery after bone marrow transplantation in a subject in need thereof. In some embodiments, the composition is to be administered to the subject after the bone marrow transplantation.

In one aspect, the present application provides an agent capable of attenuating an expression and/or function of Sphk2, for the use of promoting hematopoietic recovery after bone marrow transplantation in a subject in need thereof. In some embodiments, the agent is to be administered to the subject after the bone marrow transplantation.

In one aspect, the present application provides use of an HSPC in the preparation or manufacture of a composition for promoting hematopoietic recovery after bone marrow transplantation in a subject in need thereof, wherein an expression and/or function of Sphk2 of the HSPC is attenuated. In some embodiments, the composition is to be administered to the subject after the bone marrow transplantation.

In one aspect, the present application provides use of an HSPC in the preparation or manufacture of a composition for promoting hematopoietic recovery after bone marrow transplantation in a subject in need thereof, wherein the HSPC is derived from a donor having attenuated expression and/or function of Sphk2. In some embodiments, the composition is to be administered to the subject after the bone marrow transplantation.

In one aspect, the present application provides an HSPC having attenuated expression and/or function of Sphk2, for the use of promoting hematopoietic recovery after bone marrow transplantation in a subject in need thereof. In some embodiments, the HSPC is to be administered to the subject after the bone marrow transplantation.

In one aspect, the present application provides an HSPC derived from a donor having attenuated expression and/or function of Sphk2, for the use of promoting hematopoietic recovery after bone marrow transplantation in a subject in need thereof. In some embodiments, the HSPC is to be administered to the subject after the bone marrow transplantation.

In one aspect, the present application provides use of an agent capable of enhancing an expression and/or function of Pdk3 in the preparation or manufacture of a composition for promoting hematopoietic recovery after bone marrow transplantation in a subject in need thereof. In some embodiments, the composition is to be administered to the subject after the bone marrow transplantation.

In one aspect, the present application provides an agent capable of enhancing an expression and/or function of Pdk3, for the use of promoting hematopoietic recovery after bone marrow transplantation in a subject in need thereof. In some embodiments, the agent is to be administered to the subject after the bone marrow transplantation.

In one aspect, the present application provides use of an HSPC in the preparation or manufacture of a composition for promoting hematopoietic recovery after bone marrow transplantation in a subject in need thereof, wherein an expression and/or function of Pdk3 of the HSPC is enhanced. In some embodiments, the composition is to be administered to the subject after the bone marrow transplantation.

In one aspect, the present application provides use of an HSPC in the preparation or manufacture of a composition for promoting hematopoietic recovery after bone marrow transplantation in a subject in need thereof, wherein the HSPC is derived from a donor having enhanced expression and/or function of Pdk3. In some embodiments, the composition is to be administered to the subject after the bone marrow transplantation.

In one aspect, the present application provides an HSPC having enhanced expression and/or function of Pdk3, for the use of promoting hematopoietic recovery after bone marrow transplantation in a subject in need thereof. In some embodiments, the HSPC is to be administered to the subject after the bone marrow transplantation.

In one aspect, the present application provides an HSPC derived from a donor having enhanced expression and/or function of Pdk3, for the use of promoting hematopoietic recovery after bone marrow transplantation in a subject in need thereof. In some embodiments, the HSPC is to be administered to the subject after the bone marrow transplantation.

In some embodiments, the hematopoietic recovery comprises a recovery of white blood cell number after the bone marrow transplantation, a recovery of platelet number after the bone marrow transplantation, a recovery from hematopoietic dysfunction after the bone marrow transplantation, an expansion of HSPC number after the bone marrow transplantation, an improvement of a hematopoietic function of an HSPC after the bone marrow transplantation, an enhancement of blood cell generation by an HSPC after the bone marrow transplantation, an increase of platelet number after the bone marrow transplantation, and/or an increase of blood immune cell number after the bone marrow transplantation.

In one aspect, the present application provides a method for rejuvenating an HSPC of a subject in need thereof.

In some embodiments, the method comprises attenuating an expression and/or function of Sphk2 of the HSPC.

In some embodiments, the method comprises attenuating an expression and/or function of Sphk2 in the subject.

In some embodiments, the method comprises enhancing an expression and/or function of Pdk3 of the HSPC.

In some embodiments, the method comprises enhancing an expression and/or function of Pdk3 in the subject.

In one aspect, the present application provides use of an agent capable of attenuating an expression and/or function of Sphk2 in the preparation or manufacture of a composition for rejuvenating an HSPC of a subject in need thereof.

In one aspect, the present application provides an agent capable of attenuating an expression and/or function of Sphk2, for the use of rejuvenating an HSPC of a subject in need thereof.

In one aspect, the present application provides a rejuvenated HSPC, wherein an expression and/or function of Sphk2 has been attenuated in the HSPC.

In one aspect, the present application provides use of an agent capable of enhancing an expression and/or function of Pdk3 in the preparation or manufacture of a composition for rejuvenating an HSPC of a subject in need thereof.

In one aspect, the present application provides an agent capable of enhancing an expression and/or function of Pdk3, for the use of rejuvenating an HSPC of a subject in need thereof.

In one aspect, the present application provides a rejuvenated HSPC, wherein an expression and/or function of Pdk3 has been enhanced in the HSPC.

In some embodiments, the subject is an aged subject.

In some embodiments, the HSPC is a bone marrow derived HSPC.

In some embodiments, the HSPC is an aged HSPC.

In some embodiments, the subject has been subjected to chemotherapy.

In some embodiments, the chemotherapy comprises 5-fluorouracil.

In some embodiments, the subject has been subjected to radiation.

In some embodiments, the radiation comprises radiotherapy.

In some embodiments, the subject has been subjected to bone marrow transplantation.

In one aspect, the present application provides a method for increasing HSPC number.

In some embodiments, the method comprises attenuating an expression and/or function of Sphk2 of the HSPC.

In some embodiments, the method comprises enhancing an expression and/or function of Pdk3 of the HSPC.

In one aspect, the present application provides use of an agent capable of attenuating an expression and/or function of Sphk2 in the preparation or manufacture of a composition for increasing HSPC number.

In one aspect, the present application provides an agent capable of attenuating an expression and/or function of Sphk2, for the use of increasing HSPC number.

In one aspect, the present application provides use of an agent capable of enhancing an expression and/or function of Pdk3 in the preparation or manufacture of a composition for increasing HSPC number.

In one aspect, the present application provides an agent capable of enhancing an expression and/or function of Pdk3, for the use of increasing HSPC number.

In one aspect, the present application provides a method for expanding HSPC.

In some embodiments, the method comprises attenuating an expression and/or function of Sphk2 of the HSPC.

In some embodiments, the method comprises enhancing an expression and/or function of Pdk3 of the HSPC.

In one aspect, the present application provides use of an agent capable of attenuating an expression and/or function of Sphk2 in the preparation or manufacture of a composition for expanding HSPC.

In one aspect, the present application provides an agent capable of attenuating an expression and/or function of Sphk2, for the use of expanding HSPC.

In one aspect, the present application provides use of an agent capable of enhancing an expression and/or function of Pdk3 in the preparation or manufacture of a composition for expanding HSPC.

In one aspect, the present application provides an agent capable of enhancing an expression and/or function of Pdk3, for the use of expanding HSPC.

In one aspect, the present application provides a method for promoting a self-renewal activity of an HSPC.

In some embodiments, the method comprises attenuating an expression and/or function of Sphk2 of the HSPC.

In some embodiments, the method comprises enhancing an expression and/or function of Pdk3 of the HSPC.

In one aspect, the present application provides use of an agent capable of attenuating an expression and/or function of Sphk2 in the preparation or manufacture of a composition for promoting a self-renewal activity of an HSPC.

In one aspect, the present application provides an agent capable of attenuating an expression and/or function of Sphk2, for the use of promoting a self-renewal activity of an HSPC.

In one aspect, the present application provides use of an agent capable of enhancing an expression and/or function of Pdk3 in the preparation or manufacture of a composition for promoting a self-renewal activity of an HSPC.

In one aspect, the present application provides an agent capable of enhancing an expression and/or function of Pdk3, for the use of promoting a self-renewal activity of an HSPC.

In one aspect, the present application provides a method for increasing a regenerative potential of an HSPC.

In some embodiments, the method comprises attenuating an expression and/or function of Sphk2 of the HSPC.

In some embodiments, the method comprises enhancing an expression and/or function of Pdk3 of the HSPC.

In one aspect, the present application provides use of an agent capable of attenuating an expression and/or function of Sphk2 in the preparation or manufacture of a composition for increasing a regenerative potential of an HSPC.

In one aspect, the present application provides an agent capable of attenuating an expression and/or function of Sphk2, for the use of increasing a regenerative potential of an HSPC.

In one aspect, the present application provides use of an agent capable of enhancing an expression and/or function of Pdk3 in the preparation or manufacture of a composition for increasing a regenerative potential of an HSPC.

In one aspect, the present application provides an agent capable of enhancing an expression and/or function of Pdk3, for the use of increasing a regenerative potential of an HSPC.

In one aspect, the present application provides a method for improving a hematopoietic function of an HSPC.

In some embodiments, the method comprises attenuating an expression and/or function of Sphk2 of the HSPC.

In some embodiments, the method comprises enhancing an expression and/or function of Pdk3 of the HSPC.

In one aspect, the present application provides use of an agent capable of attenuating an expression and/or function of Sphk2 in the preparation or manufacture of a composition for improving a hematopoietic function of an HSPC.

In one aspect, the present application provides an agent capable of attenuating an expression and/or function of Sphk2, for the use of improving a hematopoietic function of an HSPC.

In one aspect, the present application provides use of an agent capable of enhancing an expression and/or function of Pdk3 in the preparation or manufacture of a composition for improving a hematopoietic function of an HSPC.

In one aspect, the present application provides an agent capable of enhancing an expression and/or function of Pdk3, for the use of improving a hematopoietic function of an HSPC.

In one aspect, the present application provides a method for maintaining and/or increasing quiescence of an HSPC.

In some embodiments, the method comprises attenuating an expression and/or function of Sphk2 of the HSPC.

In some embodiments, the method comprises enhancing an expression and/or function of Pdk3 of the HSPC.

In one aspect, the present application provides use of an agent capable of attenuating an expression and/or function of Sphk2 in the preparation or manufacture of a composition for maintaining and/or increasing quiescence of an HSPC.

In one aspect, the present application provides an agent capable of attenuating an expression and/or function of Sphk2, for the use of maintaining and/or increasing quiescence of an HSPC.

In one aspect, the present application provides use of an agent capable of enhancing an expression and/or function of Pdk3 in the preparation or manufacture of a composition for maintaining and/or increasing quiescence of an HSPC.

In one aspect, the present application provides an agent capable of enhancing an expression and/or function of Pdk3, for the use of maintaining and/or increasing quiescence of an HSPC.

In one aspect, the present application provides a method for rejuvenating an aged HSPC.

In some embodiments, the method comprises attenuating an expression and/or function of Sphk2 of the aged HSPC.

In some embodiments, the method comprises enhancing an expression and/or function of Pdk3 of the aged HSPC.

In one aspect, the present application provides use of an agent capable of attenuating an expression and/or function of Sphk2 in the preparation or manufacture of a composition for rejuvenating an aged HSPC.

In one aspect, the present application provides an agent capable of attenuating an expression and/or function of Sphk2, for the use of rejuvenating an aged HSPC.

In one aspect, the present application provides use of an agent capable of enhancing an expression and/or function of Pdk3 in the preparation or manufacture of a composition for rejuvenating an aged HSPC.

In one aspect, the present application provides an agent capable of enhancing an expression and/or function of Pdk3, for the use of rejuvenating an aged HSPC.

In some embodiments, the aged HSPC is obtained from an aged subject.

In one aspect, the present application provides a method for one or more of the following:

1) increasing the number and/or percentage of $CD41^-$ HSPC;
2) increasing the number and/or percentage of $CD150^{low}$ HSPC;
3) reducing DNA damage rate in an HSPC and/or a subject;
4) reducing reactive oxygen species (ROS) level in an HSPC and/or a subject;
5) enhancing lymphopoiesis in a subject;
6) reducing myeloid skewing in a subject;
7) restoring, in an HSPC, an expression level of an HSC aging gene, a lymphoid-lineage gene, a myeloid-lineage gene and/or a megakaryocyte/platelet gene toward that of a young HSPC;
8) increasing colony-forming progenitor frequency in bone marrow cells of a subject;
9) reducing glucose uptake of an HSPC;
10) increasing pyruvate in an HSPC;
11) increasing lactate in an HSPC;
12) increasing intracellular glycolytic lactate dehydrogenase (LDH) activity of an HSPC;
13) increasing glycolysis of an HSPC;
14) reducing oxygen consumption rate (OCR) of an HSPC;
15) reducing mitochondrial oxygen consumption of an HSPC;
16) reducing ATP production of an HSPC;
17) suppressing mitochondrial oxidative phosphorylation in an HSPC;
18) increasing LDH activity in an HSPC;
19) accelerating NADH consumption in an HSPC; and
20) ameliorating oxidative stress of an HSPC.

In some embodiments, the method comprises attenuating an expression and/or function of Sphk2 of the HSPC.

In some embodiments, the method comprises attenuating an expression and/or function of Sphk2 in the subject.

In some embodiments, the method comprises administering an HSPC with attenuated expression and/or function of Sphk2 to the subject.

In some embodiments, the method comprises administering an HSPC derived from a donor with attenuated expression and/or function of Sphk2 to the subject.

In some embodiments, the method comprises enhancing an expression and/or function of Pdk3 of the HSPC.

In some embodiments, the method comprises enhancing an expression and/or function of Pdk3 in the subject.

In some embodiments, the method comprises administering an HSPC with enhanced expression and/or function of Pdk3 to the subject.

In some embodiments, the method comprises administering an HSPC derived from a donor with enhanced expression and/or function of Pdk3 to the subject.

In one aspect, the present application provides use of an agent capable of attenuating an expression and/or function of Sphk2 in the preparation or manufacture of a composition, wherein the composition is for one or more of the following:

1) increasing the number and/or percentage of $CD41^-$ HSPC;

2) increasing the number and/or percentage of $CD150^{low}$ HSPC;
3) reducing DNA damage rate in an HSPC and/or a subject;
4) reducing reactive oxygen species (ROS) level in an HSPC and/or a subject;
5) enhancing lymphopoiesis in a subject;
6) reducing myeloid skewing in a subject;
7) restoring, in an HSPC, an expression level of an HSC aging gene, a lymphoid-lineage gene, a myeloid-lineage gene and/or a megakaryocyte/platelet gene toward that of a young HSPC;
8) increasing colony-forming progenitor frequency in bone marrow cells of a subject;
9) reducing glucose uptake of an HSPC;
10) increasing pyruvate in an HSPC;
11) increasing lactate in an HSPC;
12) increasing intracellular glycolytic lactate dehydrogenase (LDH) activity of an HSPC;
13) increasing glycolysis of an HSPC;
14) reducing oxygen consumption rate (OCR) of an HSPC;
15) reducing mitochondrial oxygen consumption of an HSPC;
16) reducing ATP production of an HSPC;
17) suppressing mitochondrial oxidative phosphorylation in an HSPC;
18) increasing LDH activity in an HSPC;
19) accelerating NADH consumption in an HSPC; and
20) ameliorating oxidative stress of an HSPC.

In one aspect, the present application provides an agent capable of attenuating an expression and/or function of Sphk2, for the use of one or more of the following:

1) increasing the number and/or percentage of $CD41^{-}$ HSPC;
2) increasing the number and/or percentage of $CD150^{low}$ HSPC;
3) reducing DNA damage rate in an HSPC and/or a subject;
4) reducing reactive oxygen species (ROS) level in an HSPC and/or a subject;
5) enhancing lymphopoiesis in a subject;
6) reducing myeloid skewing in a subject;
7) restoring, in an HSPC, an expression level of an HSC aging gene, a lymphoid-lineage gene, a myeloid-lineage gene and/or a megakaryocyte/platelet gene toward that of a young HSPC;
8) increasing colony-forming progenitor frequency in bone marrow cells of a subject;
9) reducing glucose uptake of an HSPC;
10) increasing pyruvate in an HSPC;
11) increasing lactate in an HSPC;
12) increasing intracellular glycolytic lactate dehydrogenase (LDH) activity of an HSPC;
13) increasing glycolysis of an HSPC;
14) reducing oxygen consumption rate (OCR) of an HSPC;
15) reducing mitochondrial oxygen consumption of an HSPC;
16) reducing ATP production of an HSPC;
17) suppressing mitochondrial oxidative phosphorylation in an HSPC;
18) increasing LDH activity in an HSPC;
19) accelerating NADH consumption in an HSPC; and
20) ameliorating oxidative stress of an HSPC.

In another aspect, the present application provides use of an HSPC in the preparation or manufacture of a composition, wherein an expression and/or function of Sphk2 of the HSPC is attenuated, and wherein the composition is for one or more of the following:

1) enhancing lymphopoiesis in a subject;
2) reducing myeloid skewing in a subject; and
3) increasing colony-forming progenitor frequency in bone marrow cells of a subject.

In one aspect, the present application provides use of an HSPC in the preparation or manufacture of a composition, wherein the HSPC is derived from a donor having attenuated expression and/or function of Sphk2, and wherein the composition is for one or more of the following:

1) enhancing lymphopoiesis in a subject;
2) reducing myeloid skewing in a subject; and
3) increasing colony-forming progenitor frequency in bone marrow cells of a subject.

In one aspect, the present application provides an HSPC having attenuated expression and/or function of Sphk2, for the use of one or more of the following:

1) enhancing lymphopoiesis in a subject;
2) reducing myeloid skewing in a subject; and
3) increasing colony-forming progenitor frequency in bone marrow cells of a subject.

In one aspect, the present application provides an HSPC derived from a donor having attenuated expression and/or function of Sphk2, for the use of one or more of the following:

1) enhancing lymphopoiesis in a subject;
2) reducing myeloid skewing in a subject; and
3) increasing colony-forming progenitor frequency in bone marrow cells of a subject.

In one aspect, the present application provides use of an agent capable of enhancing an expression and/or function of Pdk3 in the preparation or manufacture of a composition, wherein the composition is for one or more of the following:

1) increasing the number and/or percentage of $CD41^{-}$ HSPC;
2) increasing the number and/or percentage of $CD150^{low}$ HSPC;
3) reducing DNA damage rate in an HSPC and/or a subject;
4) reducing reactive oxygen species (ROS) level in an HSPC and/or a subject;
5) enhancing lymphopoiesis in a subject;
6) reducing myeloid skewing in a subject;
7) restoring, in an HSPC, an expression level of an HSC aging gene, a lymphoid-lineage gene, a myeloid-lineage gene and/or a megakaryocyte/platelet gene toward that of a young HSPC;
8) increasing colony-forming progenitor frequency in bone marrow cells of a subject;
9) reducing glucose uptake of an HSPC;
10) increasing pyruvate in an HSPC;
11) increasing lactate in an HSPC;
12) increasing intracellular glycolytic lactate dehydrogenase (LDH) activity of an HSPC;
13) increasing glycolysis of an HSPC;
14) reducing oxygen consumption rate (OCR) of an HSPC;
15) reducing mitochondrial oxygen consumption of an HSPC;
16) reducing ATP production of an HSPC;
17) suppressing mitochondrial oxidative phosphorylation in an HSPC;
18) increasing LDH activity in an HSPC;
19) accelerating NADH consumption in an HSPC; and
20) ameliorating oxidative stress of an HSPC.

In one aspect, the present application provides an agent capable of enhancing an expression and/or function of Pdk3, for the use of one or more of the following:

1) increasing the number and/or percentage of $CD41^-$ HSPC;
2) increasing the number and/or percentage of $CD150^{low}$ HSPC;
3) reducing DNA damage rate in an HSPC and/or a subject;
4) reducing reactive oxygen species (ROS) level in an HSPC and/or a subject;
5) enhancing lymphopoiesis in a subject;
6) reducing myeloid skewing in a subject;
7) restoring, in an HSPC, an expression level of an HSC aging gene, a lymphoid-lineage gene, a myeloid-lineage gene and/or a megakaryocyte/platelet gene toward that of a young HSPC;
8) increasing colony-forming progenitor frequency in bone marrow cells of a subject;
9) reducing glucose uptake of an HSPC;
10) increasing pyruvate in an HSPC;
11) increasing lactate in an HSPC;
12) increasing intracellular glycolytic lactate dehydrogenase (LDH) activity of an HSPC;
13) increasing glycolysis of an HSPC;
14) reducing oxygen consumption rate (OCR) of an HSPC;
15) reducing mitochondrial oxygen consumption of an HSPC;
16) reducing ATP production of an HSPC;
17) suppressing mitochondrial oxidative phosphorylation in an HSPC;
18) increasing LDH activity in an HSPC;
19) accelerating NADH consumption in an HSPC; and
20) ameliorating oxidative stress of an HSPC.

In another aspect, the present application provides use of an HSPC in the preparation or manufacture of a composition, wherein an expression and/or function of Pdk3 of the HSPC is enhanced, and wherein the composition is for one or more of the following:

1) enhancing lymphopoiesis in a subject;
2) reducing myeloid skewing in a subject; and
3) increasing colony-forming progenitor frequency in bone marrow cells of a subject.

In one aspect, the present application provides use of an HSPC in the preparation or manufacture of a composition, wherein the HSPC is derived from a donor having enhanced expression and/or function of Pdk3, and wherein the composition is for one or more of the following:

1) enhancing lymphopoiesis in a subject;
2) reducing myeloid skewing in a subject; and
3) increasing colony-forming progenitor frequency in bone marrow cells of a subject.

In one aspect, the present application provides an HSPC having enhanced expression and/or function of Pdk3, for the use of one or more of the following:

1) enhancing lymphopoiesis in a subject;
2) reducing myeloid skewing in a subject; and
3) increasing colony-forming progenitor frequency in bone marrow cells of a subject.

In one aspect, the present application provides an HSPC derived from a donor having enhanced expression and/or function of Pdk3, for the use of one or more of the following:

1) enhancing lymphopoiesis in a subject;
2) reducing myeloid skewing in a subject; and
3) increasing colony-forming progenitor frequency in bone marrow cells of a subject.

In some embodiments, the lymphopoiesis comprises T cell generation and/or B cell generation.

In some embodiments, a method of the present application is an in vitro method.

In some embodiments, a method of the present application is an ex vivo method.

In one aspect, the present application provides an HSPC, which is obtained from or by a method according to the present disclosure.

In one aspect, the present application provides an isolated HSPC.

In some embodiments, an expression and/or function of Sphk2 of the HSPC is attenuated.

In some embodiments, an expression and/or function of Pdk3 of the HSPC is enhanced.

In some embodiments, the HSPC is a rejuvenated HSPC, such as a rejuvenated aged HSPC.

In some embodiments, the HSPC has been modified to attenuate the expression and/or function of Sphk2 therein.

In some embodiments, the HSPC has been modified to enhance the expression and/or function of Pdk3 therein.

In one aspect, the present application provides a pharmaceutical composition, comprising an HSPC according to the present application. The pharmaceutical composition optionally comprises a pharmaceutically acceptable carrier.

In some embodiments of any aspect of the present application, the expression and/or function of the Pdk3 is enhanced at least partially by enriching H3K9 acetylation in a promoter region of the Pdk3 gene.

In some embodiments of any aspect of the present application, the expression and/or function of the Sphk2 is attenuated by inhibiting an expression and/or function of the Sphk2 gene, and/or inhibiting an expression and/or function of the Sphk2 protein.

In some embodiments of any aspect of the present application, the expression and/or function of the Sphk2 is attenuated with a Sphk2 inhibitor.

In some embodiments, the Sphk2 inhibitor is a small molecule inhibitor.

In some embodiments, the Sphk2 inhibitor comprises a compound of formula (I) or a pharmaceutically acceptable salt thereof:

(I)

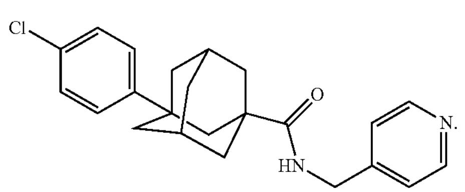

In some embodiments, the Sphk2 inhibitor comprises a compound of formula (II) or a pharmaceutically acceptable salt thereof:

(II)

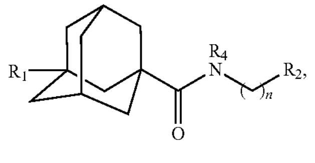

wherein:

$R_1$ is phenyl, or a phenyl substituted with a halogen;

$R_2$ is aryl, heteroaryl, or a substituted aryl or heteroaryl;

$R_4$ is H or alkyl; and n is an integer of at least 1.

In some embodiments of any aspect of the present application, the HSPC comprises a hematopoietic stem cell (HSC), a hematopoietic progenitor cell (HPC), a long-term HSC (LT-HSC), a short-term HSC (ST-HSC), a multipotent progenitor cell (MPP), and/or a CD150 HSC.

In one aspect, the present application provides a method for screening a candidate agent for preventing, treating and/or alleviating a disease or disorder related to hematopoietic dysfunction and/or hematopoietic injury.

In some embodiments, the method comprises determining an ability of the candidate agent in attenuating an expression and/or function of Sphk2.

In some embodiments, the method comprises determining an ability of the candidate agent in enhancing an expression and/or function of Pdk3.

In one aspect, the present application provides a method for screening a candidate agent for rejuvenating an HSPC.

In some embodiments, the method comprises determining an ability of the candidate agent in attenuating an expression and/or function of Sphk2.

In some embodiments, the method comprises determining an ability of the candidate agent in enhancing an expression and/or function of Pdk3.

In one aspect, the present application provides a system for screening a candidate agent for preventing, treating and/or alleviating a disease or disorder related to hematopoietic dysfunction and/or hematopoietic injury.

In some embodiments, the system comprises an agent capable of detecting and/or revealing an attenuation of an expression and/or function of Sphk2.

In some embodiments, the system comprises an agent capable of detecting and/or revealing an enhancement of an expression and/or function of Pdk3.

In one aspect, the present application provides a system for screening a candidate agent for rejuvenating an HSPC.

In some embodiments, the system comprises an agent capable of detecting and/or revealing an attenuation of an expression and/or function of Sphk2.

In some embodiments, the system comprises an agent capable of detecting and/or revealing an enhancement of an expression and/or function of Pdk3.

In one aspect, the present application provides use of an agent capable of detecting and/or revealing an attenuation of an expression and/or function of Sphk2 in the preparation or manufacture of a composition or system for screening a candidate agent for preventing, treating and/or alleviating a disease or disorder related to hematopoietic dysfunction and/or hematopoietic injury.

In one aspect, the present application provides use of an agent capable of detecting and/or revealing an attenuation of an expression and/or function of Sphk2 in the preparation or manufacture of a composition or system for screening a candidate agent for rejuvenating an HSPC.

In one aspect, the present application provides use of an agent capable of detecting and/or revealing an enhancement of an expression and/or function of Pdk3 in the preparation or manufacture of a composition or system for screening a candidate agent for preventing, treating and/or alleviating a disease or disorder related to hematopoietic dysfunction and/or hematopoietic injury.

In one aspect, the present application provides use of an agent capable of detecting and/or revealing an enhancement of an expression and/or function of Pdk3 in the preparation or manufacture of a composition or system for screening a candidate agent for rejuvenating an HSPC.

BRIEF DESCRIPTION OF DRAWINGS

FIG. 7 illustrates that Sphk2 inhibition increases HSPC pool and promotes HSPC quiescence. The absolute number of HSPCs (LT-HSC, ST-HSC, MPP and CD150HSC) in the bone marrow (a) and cell cycle analysis of CD150 HSCs (b) in bone marrow from Vav-Cre; SphK2$^{flox/flox}$ mice. (a, $Cre^-$ n=6 mice, $Cre^+$ n=8; b, $Cre^-$ n=6 mice, $Cre^+$ n=4). Data represent mean±s.d. Two-tailed Student's t-tests were used to assess statistical significance. *$P<0.05$, $P<0.01$, *$P<0.001$.

FIG. 8 illustrates representative image and quantification of sorted CD150 HSCs immunostained with Sphk2, from Sphk2Δ/Δ or control mice (n=25 cells from 3 mice).

FIG. 9 illustrates representative image and quantification of sorted CD150 HSCs immunostained with S1P, from Sphk2Δ/Δ or control mice (n=25 cells from 3 mice).

DETAILED DESCRIPTION

Figure 1:
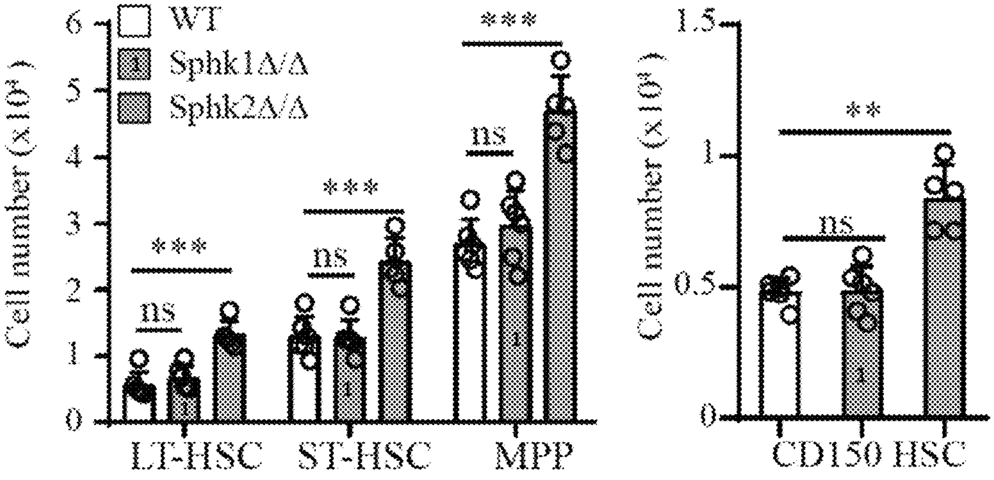
FIG. 1 illustrates the absolute number of HSPCs (LT-HSC, ST-HSC, MPP and CD150HSC) in the bone marrow from Sphk1Δ/Δ (n=6 mice), Sphk2Δ/Δ (n=5 mice) or control mice (WT) (n=6 mice).

In general, deletion of Sphk2 gene (mouse NCBI accession number: NP_001166032, human Genbank Gene ID: 56848) is believed to result in slow growth, apoptosis and weakened tumor-forming ability in various tumor cells. By using Sphk2 gene knockout mouse models, the present inventor first found that Sphk2 gene knockout enhanced the self-renewal ability of hematopoietic stem cells and increased the number thereof, which was manifested in an increase of the number and function of hematopoietic stem cells in mice. It was also found in the present application that after the stimulation by radiation and chemotherapeutic drugs, the post-injury repair of hematopoietic system in Sphk2 gene knockout mice was significantly accelerated, and the survival period of the mice was significantly prolonged under multiple chemotherapy stimulations, due to increased hematopoietic stem cell number and function. This suggests that Sphk2 gene is an effective therapeutic target for targeting hematopoietic stem cells to treat hematopoietic dysfunction diseases.

It was also found by the present inventor that hematopoietic stem cells from Sphk2 gene knockout mice gave accelerated hematopoietic reconstitution post-bone marrow transplantation, which was manifested in acceleration in the recovery of hematopoietic stem cell pool and platelets and blood immune cells after bone marrow transplantation. This indicates that Sphk2 gene is an effective therapeutic target for targeting hematopoietic stem cells to treat hematopoietic dysfunction diseases after bone marrow transplantation.

ABC294640, also known as 3-(4-chloro-phenyl)-adamantane-1-carboxylic acid (pyridin-4-ylmethyl)-amide, has a structure as shown in formula (I). ABC294640 has been reported to be an inhibitor of sphingosine kinase 2 (Sphk2) (see WO2006138660A2) and can reduce the production of sphingosine-1-phosphate (S1P). S1P is a second messenger of eukaryotic organisms, which can exert a variety of important physiological functions and can promote the growth of cancer tissues and the occurrence of pathological inflammations.

(I)

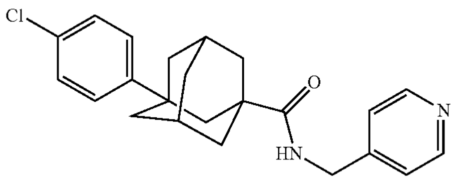

The present inventor has demonstrated for the first time use of Sphk2 inhibitor ABC294640 for the treatment of hematopoietic dysfunction diseases. The inventor found that intraperitoneal injection of ABC294640 in mice could significantly increase the number and function of hematopoietic stem cells, showing a therapeutic effect on primary hematopoietic dysfunction. Moreover, ABC294640 could effectively promote the recovery of hematopoietic stem cell pool, platelets and white blood cells in mice after stimulation of the chemotherapeutic drug 5-fluorouracil and radiation-induced injury, and had remarkable improving effects on the hemogram, e.g., recovery of white blood cells and platelets, after being injured and stimulated; and the survival period of the mice injected with ABC294640 was significantly prolonged after multiple high-dose chemotherapy stimulations, indicating that ABC294640 has therapeutic effect on the decrease in survival rate caused by severe damages to the blood system.

The present application has also demonstrated for the first time use of Sphk2 inhibitor (e.g., ABC294640) in the treatment of hematopoietic dysfunction diseases after bone marrow transplantation. The present inventor found that after hematopoietic stem cell bone marrow transplantation, Sphk2 inhibitors (e.g. with intraperitoneal injection of ABC294640 in mice) could significantly increase the number of hematopoietic stem cells, and significantly accelerate the recovery of platelets and blood immune cells, and had remarkable improving effect on hemogram, e.g., the recovery of white blood cells and platelets, after hematopoietic stem cell bone marrow transplantation.

The present application has explored new medicinal value of Sphk2 inhibitor (such as ABC294640, a small molecule compound), i.e., Sphk2 inhibitors (such as ABC294640) are of therapeutic significance when used for treatment primary hematopoietic dysfunction, hematopoietic dysfunction caused by chemical drugs or radiation-induced injuries, and hemopoietic dysfunction after hematopoietic stem cell bone marrow transplantation.

The present inventor has demonstrated for the first time that Sphk2 inhibitors (e.g., ABC294640, its functional derivatives and analogs) are effective in expanding hematopoietic stem cell number and promoting hematopoietic stem cell function for primary hematopoietic dysfunction diseases or post-injury repair of the blood system after environmental radiation, chemo- or radio-therapy and bone marrow transplantation.

The present application shows that the number of HSPCs (e.g., hematopoietic stem cells) increased significantly (e.g., among bone marrow cells) when the expression and/or functions of Sphk2 is attenuated (e.g. as in Sphk2 gene knockout mice).

The present application also shows that the number of HSPCs (e.g., hematopoietic stem cells) was significantly increased after chemotherapy-induced injury when the expression and/or functions of Sphk2 is attenuated (e.g. as in Sphk2 gene knockout mice). The use of a Sphk2 inhibitor (e.g., ABC294640, its functional derivatives and analogs) resulted in a remarkable increase in the number of HSPCs (e.g., hematopoietic stem cells) after chemotherapy.

The present application also shows that a Sphk2 inhibitor (e.g., ABC294640, its functional derivatives and analogs) remarkably promoted the post-injury repair of HSPCs (e.g., hematopoietic stem cells). The Sphk2 inhibitor (e.g., ABC294640, its functional derivatives and analogs) significantly accelerated recovery of white blood cells after the stimulation of the chemotherapeutic drug (e.g. 5-fluorouracil). The Sphk2 inhibitor (e.g., ABC294640, its functional derivatives and analogs) significantly accelerated recovery of platelets after the stimulation of the chemotherapeutic drug (e.g. 5-fluorouracil). The Sphk2 inhibitor (e.g., ABC294640, its functional derivatives and analogs) significantly accelerated recovery of white blood cells after the stimulation of radiation. The Sphk2 inhibitor (e.g., ABC294640, its functional derivatives and analogs) significantly accelerated recovery of platelets after the stimulation of radiation. The administration of a Sphk2 inhibitor (e.g., ABC294640, its functional derivatives and analogs) after bone marrow transplantation resulted in a remarkable increase in the number of HSPCs (e.g., hematopoietic stem cells). The Sphk2 inhibitor (e.g., ABC294640, its functional derivatives and analogs) significantly accelerated the recovery of white blood cells after bone marrow transplantation.

The present application also shows that a Sphk2 inhibitor (e.g., ABC294640, its functional derivatives and analogs) significantly accelerated the recovery of platelets after bone marrow transplantation.

The present application shows that attenuating the expression and/or function of Sphk2 (e.g., with Sphk2 gene knockout) led to an enhancement of the function of HSPCs (e.g., hematopoietic stem cells). Sphk2 attenuated HSPCs (e.g., hematopoietic stem cells) provided significantly higher reconstitution. Sphk2 attenuated HSPCs (e.g., hematopoietic stem cells) were able to provide multi-hematopoietic lineage and more donor derived hematopoietic stem cells.

Further, Sphk2 inhibitors (e.g., ABC294640, its functional derivatives and analogs) resulted in increased hematopoietic stem cell number and improved function.

The present application shows that the number/percentage of $CD41^-$HSCs increased significantly by attenuating Sphk2 and/or upregulating Pdk3.

In addition, the number/percentage of $CD150^{low}$HSCs increased significantly by attenuating Sphk2 and/or upregulating Pdk3.

Also, by attenuating Sphk2 and/or upregulating Pdk3 in aged CD150 HSCs, the ROS levels was reduced.

Further, by attenuating Sphk2 and/or upregulating Pdk3, lymphopoiesis (both B and T cells in primary transplantation, and B cells in secondary transplantation) was improved, and myeloid skewing was reduced, e.g., after HSPC transplantation.

In addition, by attenuating Sphk2 and/or upregulating Pdk3, the expression of HSC aging genes, lymphoid-lineage genes, myeloid-lineage genes and/or megakaryocyte/platelet genes was restored towards the level in young HSCs (yHSCs).

Further, by attenuating Sphk2 and/or upregulating Pdk3, one or more of the followings was observed: increased colony-forming progenitor frequency in bone marrow cells; reduced glucose uptake by the HSPCs; increased pyruvate and lactate in the HSPCs; increased intracellular glycolytic LDH activity; increased glycolysis; reduced oxygen consumption rate (OCR); reduced mitochondrial oxygen consumption; reduced ATP production; increased $NAD^+$/NADH ratio; suppressed mitochondrial oxidative phosphorylation (OXPHOS); increased LDH activity; accelerated consumption of NADH; ameliorated oxidative stress; reduced ROS levels.

The present application demonstrated for the first time that pyruvate dehydrogenase kinase (Pdk) 3 was upregulated after attenuating Sphk2. It was also found that H3K9 acetylation was enriched in the promoter region of Pdk3 after attenuation of Sphk2.

Definitions

As used herein, the term "subject" generally refers to an individual. The subject may include, for example, domesticated animals, such as cats and dogs, livestock (e.g., cattle, horses, pigs, sheep, and goats), laboratory animals (e.g., mice, rabbits, rats, and guinea pigs), mammals, non-human mammals, primates, non-human primates, rodents, birds, reptiles, amphibians, fish, and any other animal. The subject may also comprise a mammal, such as a primate or a human.

As used herein, the term "alkyl" generally refers to a group and as a structural element of other groups, e.g., a substituted alkyl, it can be either straight-chained or branched. For example, alkyl includes methyl, ethyl, propyl, isopropyl, butyl, isobutyl.

As used herein, the term "aryl" generally refers to a monocyclic or fused bicyclic aromatic ring assembly containing six to ten ring carbon atoms. For example, aryl may be phenyl or naphthyl.

As used herein, the term "heteroaryl" generally refers to an aryl where one or more of the ring members are a heteroatom or moiety selected from —O—, —N=, —NR—, —C(O)—, —S—, —S(O)— or —$S(O)_2$—, wherein R may be a hydrogen, C1-C4 alkyl or a nitrogen protecting group.

As used herein, the term "cycloalkyl" generally refers to a saturated or partially unsaturated, monocyclic, fused bicyclic or bridged polycyclic ring assembly containing the number of ring atoms as indicated.

As used herein, the term "halogen" generally refers to chloro or fluoro, but may also be bromo or iodo.

As used herein, the term "hematopoietic stem cells" or "HSCs" generally refers to immature hematopoietic cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). HSCs are interchangeably described as stem cells throughout the specification. Such cells may include $CD34^+$ cells. $CD34^+$ cells are immature cells that express the CD34 cell surface marker. $CD34^+$ cells are believed to include a subpopulation of cells with the stem cell properties defined above. Such cells may include $CD150^+$ cells. $CD150^+$ cells are immature cells that express the CD150 cell surface marker. The $CD150^+$ cells may have long-term, multilineage-reconstituting ability. HSCs may also include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage and/or lymphoid tissue-specific macrophage cell lineage. In addition, HSCs may also include long term HSC (LT-HSC) and short term HSC (ST-HSC). ST-HSCs are more active and more proliferative than LT-HSCs. However, LT-HSC have unlimited self-renewal ability (i.e., they survive throughout adulthood), whereas ST-HSC have limited self-renewal ability (i.e., they survive for only a limited period of time). Any of these HSCs can be used in any of the methods described herein. Hematopoietic stem cells may be obtained from blood products. A blood product includes a product obtained from the body or an organ of the body containing cells of hematopoietic origin. Such sources include un-fractionated bone marrow, umbilical cord, peripheral blood, liver, thymus, lymph and spleen. All of the aforementioned crude or un-fractionated blood products can be enriched for cells having hematopoietic stem cell characteristics.

As used herein, the term "treating" or "treatment" generally refers to alleviating or abating a disease, a disorder and/or at least one of its attendant symptoms.

As used herein, the term "expansion" or "expanding" when used in connection with a cell or cells, generally refers to an increase in the number of a characteristic cell type, or cell types, from an initial cell population of cells, which may or may not be identical. The initial cells used for expansion may not be the same as the cells generated from expansion.

As used herein, the term "hematopoietic stem cell and/or progenitor cell" or "HSPC" generally refers to a hematopoietic stem cell and/or a hematopoietic progenitor cell. In some cases, the terms "HSPC" "HSC" may be used interchangeably. The HSPC of the present application may comprise a hematopoietic stem cell (HSC), a hematopoietic progenitor cell (HPC), a long-term HSC (LT-HSC), a short-term HSC (ST-HSC), a multipotent progenitor cell (MPP), and/or a $CD150^+$ HSC.

As used herein, the term "primary" when used in connection with a disease or disorder, generally refers to a disease or disorder arising spontaneously and not associated with or caused by a previous disease or injury.

As used herein, the term "enhancing hematopoietic recovery", "promoting hematopoietic recovery", or "increasing hematopoietic recovery" generally refers to an increase in the hematopoiesis detected in a subject caused by a treatment compared to the hematopoiesis in the subject before the treatment or in an otherwise identical but untreated subject.

As used herein, the term "quiescence" or "quiescent" when used in connection with an HSC, generally refers to the HSC being in a state of reversible growth arrest, for prolonged periods of time. It may represent a state of poised potential and active restraint.

As used herein, the term "isolated" when used in connection with a cell (such as an HSC), generally refers to a cell or cells that has been removed from an organism or population of cells in which it was originally found, or a descendant of such a cell. Optionally the cell has been cultured in vitro, e.g., in the presence of other cells and/or an appropriate culture medium.

As used herein, the term "small molecule" generally refers to a low molecular weight (e.g., lower than about 900 Dalton) compound (such as an organic compound).

As used herein, the term "Pdk3" generally refers to the gene or protein of pyruvate dehydrogenase lipoamide kinase isozyme 3, also known as CMTX6, or GS1-358P8.4. It codes for an isozyme of pyruvate dehydrogenase kinase. In the present application, the term Pdk3 also encompasses a functional fragment or variant of Pdk3. The Pdk3 may be a human Pdk3 (NCBI gene ID: 5165), or a functional ortholog/homolog thereof, such as a protein with an amino acid sequence that is at least 50% (e.g., at least 60%, at least 70%, at least 80%, at least 90%, at least 95%, at least 96%, at least 97%, at least 98%, at least 99%) to human Pdk3.

As used herein, the term "Sphk2" generally refers to the gene or protein of sphingosine kinase 2, also known as SPK-2, SK 2, SK-2 or SPK 2. It encodes for a sphingosine kinase isozyme that catalyzes the phosphorylation of sphingosine into sphingosine 1-phosphate. In the present application, the term Sphk2 also encompasses a functional fragment or variant of Sphk2. The Sphk2 may be a human Sphk2 (NCBI gene ID: 56848), or a functional ortholog/homolog thereof, such as a protein with an amino acid sequence that is at least 50% (e.g., at least 60%, at least 70%, at least 80%, at least 90%, at least 95%, at least 96%, at least 97%, at least 98%, at least 99%) to human Sphk2.

As used herein, the term "rejuvenating", "rejuvenated" or "rejuvenation" generally refers to restoring to a state, an appearance and/or a function of a corresponding younger individual. It may also refer to restoring to a state, an appearance and/or a function of the same individual at an earlier time point.

As used herein, the term "aged" generally refers to being old, being of advanced age, and/or having one or more characteristics of an individual of an advanced age.

As used herein, the term "promoter region" generally refers to a sequence of nucleotides that promotes transcription of an associated gene. For example, it may be a a site on a DNA molecule at which an RNA polymerase binds and initiates transcription. It may also refer to a gene sequence that activates transcription. As used herein, the term "promoter region of the Pdk3 gene" may refer to a sequence of nucleotides that promotes transcription of the Pdk3 gene.

Methods and Compositions for Disease Prevention and/or Treatment

In one aspect, the present application provides methods for preventing, treating and/or alleviating a disease or disorder related to hematopoietic dysfunction and/or hematopoietic injury in a subject in need thereof.

The method may increase hematopoietic cell (e.g., HSPCs, or HSCs) expansion, reduce DNA damage, reduce reactive oxygen species (ROS) level, enhance lymphopoiesis, reduce myeloid skewing, and/or increase colony-forming progenitor frequency in bone marrow cells in the subject.

The method may comprise attenuating an expression and/or function of Sphk2 in the subject. For example, the method may comprise attenuating an expression and/or function of the Sphk2 in the bone marrow of the subject. In some cases, the method may comprise attenuating an expression and/or function of the Sphk2 in one or more HSPCs in the subject.

Alternatively, or in addition, the method may comprise enhancing an expression and/or function of Pdk3 in the subject. For example, the method may comprise enhancing an expression and/or function of Pdk3 in the bone marrow of the subject. For example, the method may comprise enhancing an expression and/or function of Pdk3 in one or more HSPCs in the subject.

The method of the present application may alternatively or additionally comprise administering to the subject one or more HSPCs.

In another aspect, the present application provides a pharmaceutical composition or a medicament for preventing, treating and/or alleviating a disease or disorder related to hematopoietic dysfunction and/or hematopoietic injury in a subject in need thereof.

The pharmaceutical composition or medicament may increase hematopoietic cell (e.g., HSPCs, or HSCs) expansion, reduce DNA damage, reduce reactive oxygen species (ROS) level, enhance lymphopoiesis, reduce myeloid skewing, and/or increase colony-forming progenitor frequency in bone marrow cells in the subject.

The pharmaceutical composition or medicament may comprise an agent capable of attenuating an expression and/or function of Sphk2.

Alternatively, or additionally, the pharmaceutical composition or medicament may comprise an agent capable of enhancing an expression and/or function of Pdk3.

In some cases, the pharmaceutical composition or medicament may comprise one or more HSPCs according to the present application.

The disease or disorder may comprise poor hemogram index, reduction of immune cells, reduction of white blood cells, reduction of platelets, and/or a bone marrow failure syndrome. The disease or disorder may be primary, or may be related to, induced by, and/or caused by an injury, such as a radiation-induced injury, or a therapy (e.g., chemotherapy or radiotherapy) induced injury. As an example, the chemotherapy may comprise 5-fluorouracil. However, it may be any therapy that might lead to a hematopoietic disorder, injury and/or dysfunction.

Methods and Compositions for Promoting Hematopoietic Recovery after Bone Marrow Transplantation The present application also provides a method for promoting hematopoietic recovery after bone marrow transplantation in a subject in need thereof.

The method may comprise attenuating an expression and/or function of Sphk2 in the subject. The expression and/or function of Sphk2 in the subject may be attenuated in the bone marrow. In some cases, the expression and/or function of Sphk2 in the subject may be attenuated in the HSPCs in the subject. In some cases, the method may comprise attenuating the expression and/or function of Sphk2 in the bone marrow being transplanted, such as in one or more HSPCs of the bone marrow being transplanted.

In some cases, the expression and/or function of Sphk2 in the subject may be attenuated after the bone marrow transplantation.

In some cases, the subject may be administered with one or more HSPCs with attenuated expression and/or function of Sphk2. For example, the bone marrow that has been transplanted may comprise one or more HSPCs with attenuated expression and/or function of Sphk2.

In some cases, the bone marrow that has been transplanted may be derived from a donor that has attenuated expression and/or function of Sphk2.

The method may alternatively, or additionally, comprise enhancing an expression and/or function of Pdk3 in the subject. The expression and/or function of Pdk3 in the subject may be enhanced in the bone marrow. In some cases, the expression and/or function of Pdk3 in the subject may be enhanced in the HSPCs in the subject. In some cases, the method may comprise enhancing an expression and/or function of Pdk3 in the bone marrow being transplanted, such as in one or more HSPCs of the bone marrow being transplanted.

In some cases, the expression and/or function of Pdk3 in the subject may be enhanced after the bone marrow transplantation.

In some cases, the subject may be administered with one or more HSPCs with enhanced expression and/or function of Pdk3. For example, the bone marrow that has been transplanted may comprise one or more HSPCs with enhanced expression and/or function of Pdk3.

In some cases, the bone marrow that has been transplanted may be derived from a donor that has enhanced expression and/or function of Pdk3.

In another aspect, the present application provides a composition for promoting hematopoietic recovery after bone marrow transplantation in a subject in need thereof. In some cases, the composition may be administered to the subject after the bone marrow transplantation.

The composition may comprise an agent capable of attenuating an expression and/or function of Sphk2.

Alternatively, or additionally, the composition may comprise an agent capable of enhancing an expression and/or function of Pdk3.

In some cases, the composition may comprise one or more HSPCs, as described according to any aspect of the present application.

The hematopoietic recovery may comprise a recovery of white blood cell number, a recovery of platelet number, a recovery from hematopoietic dysfunction, an expansion of HSPC number, an improvement of a hematopoietic function of an HSPC, an enhancement of blood cell generation by an HSPC, an increase of platelet number, and/or an increase of blood immune cell number, e.g., after bone marrow transplantation.

Methods and Compositions for Rejuvenating HSPCs

In another aspect, the present application provides a method for rejuvenating an HSPC of a subject in need thereof.

The method may comprise attenuating an expression and/or function of Sphk2 in the HSPC to be rejuvenated. For example, the method may comprise attenuating an expression and/or function of the Sphk2 in the subject (the subject from which the HSPC is derived), e.g., in the bone marrow of the subject. In some cases, the method may comprise attenuating an expression and/or function of the Sphk2 in one or more HSPCs in the subject.

Alternatively, or in addition, the method may comprise enhancing an expression and/or function of Pdk3 in the HSPC to be rejuvenated. For example, the method may comprise enhancing an expression and/or function of Pdk3 in the subject (the subject from which the HSPC is derived), e.g., in the bone marrow of the subject. In some cases, the method may comprise enhancing an expression and/or function of Pdk3 in one or more HSPCs in the subject.

In another aspect, the present application provides a composition for rejuvenating an HSPC of a subject in need thereof.

The composition may comprise an agent capable of attenuating an expression and/or function of Sphk2.

Alternatively, or additionally, the composition may comprise an agent capable of enhancing an expression and/or function of Pdk3.

Rejuvenation of an HSPC may be determined by comparing one or more genetic and/or functional feature of the treated HSPC with that of a corresponding untreated HSPC (e.g., an HSPC obtained from the same aged subject, except that it has not been treated or rejuvenated according to the present application). Rejuvenation of an HSPC may also be determined by comparing one or more genetic and/or functional feature of the treated HSPC according to the present application with that of a corresponding younger HSPC (e.g., an untreated HSPC taken from a younger individual, or an untreated HSPC taken for the same individual of a smaller age).

For example, hematopoietic functions of an aged HSPC (e.g., a HSPC taken from an aged individual or subject) may be improved. The multilineage potential of an HSPC may be maintained during aging. The number of HSPCs may be increased in aged subjects or individuals. The quiescence of aged HSPCs may be preserved, for example, the percentage of G0-phase fraction of HSPCs may be increased, e.g., by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds, at least about 6 folds, at least about 7 folds, at least about 8 folds, at least about 9 folds, at least about 10 folds or more.

The frequency of lymphocytes in aged individuals may be notably increased compared to corresponding untreated individuals (e.g., individuals that otherwise are of the same genetic composition).

The frequency of myeloid cells in aged individuals may be notably decreased compared to corresponding untreated individuals (e.g., individuals that otherwise are of the same genetic composition).

CD41-HSPCs may be increased, e.g., by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds, at least about 6 folds (such as at least about 6.5 folds), at least about 7 folds, at least about 8 folds, at least about 9 folds, at least about 10 folds or more.

$CD150^{low}$HSPCs may be increased, e.g., by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds (such as at least about 5.5 folds), at least about 6 folds, at least about 7 folds, at least about 8 folds, at least about 9 folds, at least about 10 folds or more.

DNA damage rate in aged CD150 HSPCs may be reduced.

ROS levels in aged CD150 HSCs may be markedly reduced compared to corresponding untreated individuals (e.g., individuals that otherwise are of the same genetic composition), e.g., reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds, at least about 6 folds, at least about 7 folds, at least about 8 folds, at least about 9 folds, at least about 10 folds or more.

Reconstitution in subjects transplanted with total bone marrow cells from aged subjects may be increased comparing to the corresponding control. For example, with an increase of reconstitution of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds, at least about 6 folds, at least about 7 folds, at least about 8 folds, at least about 9 folds, at least about 10 folds or more.

HSC aging genes, lymphoid-lineage genes, myeloid-lineage genes and/or megakaryocyte/platelet genes in an aged HSPC may be restored toward levels of those in a younger HSPC.

Lymphopoiesis may be increased and myeloid skewing may be suppressed in the peripheral blood.

Colony-forming progenitor frequency may be significantly higher in bone marrow cells from the Sphk2 attenuated mice than the corresponding control.

Methods and Compositions for Expanding/Enhancing HSPCs

In another aspect, the present application provides a method for one or more of the followings: increasing HSPC cell number; expanding HSPCs; promoting self-renewal of HSPCs; increasing a regenerative potential of HSPCs; improving a hematopoietic function of HSPCs; rejuvenating an HSPC (such as an aged HSPC); maintaining and/or increasing quiescence of HSPCs; increasing the number and/or percentage of $CD41^-$ HSPC; increasing the number and/or percentage of $CD150^{low}$ HSPC; reducing DNA damage rate in an HSPC; reducing reactive oxygen species (ROS) level in an HSPC; restoring, in an HSPC, an expression level of an HSC aging gene, a lymphoid-lineage gene, a myeloid-lineage gene and/or a megakaryocyte/platelet gene toward that of a young HSPC; reducing glucose uptake of an HSPC; increasing pyruvate in an HSPC; increasing lactate in an HSPC; increasing intracellular glycolytic lactate dehydrogenase (LDH) activity of an HSPC; increasing glycolysis of an HSPC; reducing oxygen consumption rate (OCR) of an HSPC; reducing mitochondrial oxygen consumption of an HSPC; reducing ATP production of an HSPC; suppressing mitochondrial oxidative phosphorylation in an HSPC; increasing LDH activity in an HSPC; accelerating NADH consumption in an HSPC; and ameliorating oxidative stress of an HSPC.

The method may comprise attenuating an expression and/or function of Sphk2 of the HSPCs.

In some cases, the method may comprise enhancing an expression and/or function of Pdk3 of the HSPCs.

The method may be an in vitro method. The method may also be an ex vivo method. In some cases, the method is an ex vivo method.

In another aspect, the present application provides a composition for one or more of the followings: increasing HSPC cell number; expanding HSPCs; promoting self-renewal of HSPCs; increasing a regenerative potential of HSPCs; improving a hematopoietic function of HSPCs; rejuvenating an HSPC (such as an aged HSPC); maintaining and/or increasing quiescence of HSPCs; increasing the number and/or percentage of $CD41^-$ HSPC; increasing the number and/or percentage of $CD150^{low}$ HSPC; reducing DNA damage rate in an HSPC; reducing reactive oxygen species (ROS) level in an HSPC; restoring, in an HSPC, an expression level of an HSC aging gene, a lymphoid-lineage gene, a myeloid-lineage gene and/or a megakaryocyte/platelet gene toward that of a young HSPC; reducing glucose uptake of an HSPC; increasing pyruvate in an HSPC; increasing lactate in an HSPC; increasing intracellular glycolytic lactate dehydrogenase (LDH) activity of an HSPC; increasing glycolysis of an HSPC; reducing oxygen consumption rate (OCR) of an HSPC; reducing mitochondrial oxygen consumption of an HSPC; reducing ATP production of an HSPC; suppressing mitochondrial oxidative phosphorylation in an HSPC; increasing LDH activity in an HSPC; accelerating NADH consumption in an HSPC; and ameliorating oxidative stress of an HSPC.

The composition may comprise an agent capable of attenuating an expression and/or function of Sphk2.

Alternatively, or additionally, the composition may comprise an agent capable of enhancing an expression and/or function of Pdk3.

The aged HSPC may be obtained or isolated from an aged subject or individual, such as an aged human being.

An increase in the number of HSPCs may refer to an increase of at least one HSPC, about at least a 10% increase, about at least a 20% increase, about at least a 30% increase, about at least a 40% increase, about at least a 50% increase, about at least a 60% increase, about at least a 70% increase, about at least a 80% increase, about at least a 90% increase, about at least a 100% increase, about at least a 1.5 fold increase, about at least a 2 fold increase, about at least a 2.5 fold increase, about at least a 3 fold increase, about at least a 3.5 fold increase, about at least a 4 fold increase, about at least a 4.5 fold increase, or greater. The increase of HSPCs may be measured indirectly by counting the number of cells positive for certain characteristic markers.

In some cases, an increase of the number of LT-HSCs are achieved with the methods or compositions of the present application. For example, the LT-HSCs may be detected as $CD34^-Flk^-Lin^-Sca1^+c\text{-}KIT^+$. The number of LT-HSCs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold, by at least about 2 fold (such as at least about 2-3 fold, such as at least about 2-2.5 fold), by at least about 2.5 fold, by at least about 3 fold, by at least about 3.5 fold, by at least about 4 fold, by at least about 4.5 fold, or greater.

In some cases, an increase of the number of ST-HSCs are achieved with the methods or compositions of the present application. For example, the ST-HSCs may be detected as $CD34^-Flk^+Lin^-Sca1^+c\text{-}KIT^+$. The number of ST-HSCs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold (such as at least about 1-2 fold, such as at least about 1-1.5 fold, such as about at least about 1.9 fold), by at least about 2 fold, by at least about 2.5 fold, by at least about 3 fold, by at least about 3.5 fold, by at least about 4 fold, by at least about 4.5 fold, or greater.

In some cases, an increase of the number of multipotent progenitor cells (MPPs) are achieved with the methods or compositions of the present application. For example, the MPPs may be detected as $CD34^+Flk^+Lin^-Sca1^+c\text{-}KIT^+$. The number of MPPs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold (such as at least about 1-2 fold, such as at least about 1-1.5 fold, such as about at least about 1.7 fold), by at least about 2 fold, by at least about 2.5 fold, by at least about 3 fold, by at least about 3.5 fold, by at least about 4 fold, by at least about 4.5 fold, or greater.

In some cases, an increase of the number of $CD150^+$HSCs are achieved with the methods or compositions of the present application. For example, the $CD150^+$HSCs may be detected as $CD150^+CD48^-Lin^-Sca1^+c\text{-}KIT^+$. The number of CD150' HSCs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold, by at least about 2 fold (such as at least about 2-3 fold, such as at least about 2-2.5 fold), by at least about 2.5 fold, by at least about 3 fold, by at least about 3.5 fold, by at least about 4 fold, by at least about 4.5 fold, or greater.

The method of the present application may comprise administering an agent attenuating the expression and/or function of Sphk2 (e.g., an inhibitor of Sphk2) to the HSPC, for example, by contacting such an agent with a starting cell population (e.g., an unattenuated population of cells) comprising HSPCs.

In some cases, the method of the present application may comprise administering an agent enhancing the expression and/or function of Pdk3 (e.g., an activator of Pdk3, or a transgene encoding Pdk3) to or into the HSPC, for example, by introducing such an agent into a starting cell population comprising HSPCs, or by contacting such an agent with a starting cell population comprising HSPCs.

The population of the HSPCs treated according to the present application may be administered to a subject. In some cases, the subject may be the same subject from which the untreated population of HSPCs was derived.

The method of the present application may comprise: (a) providing a starting cell population comprising HSPCs and (b) culturing said starting cell population in vitro or ex vivo in presence of an agent capable of attenuating the expression and/or activity of Sphk2.

In some cases, the method of the present application may comprise: (a) providing a starting cell population comprising HSPCs and (b) culturing said starting cell population in vitro or ex vivo in presence of an agent capable of enhancing the expression and/or function of Pdk3.

The cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers.

The starting cell population may be derived from bone marrow of a subject and/or a donor. The expansion or culturing of HSPCs may be carried out in a basal medium, which is supplemented with the mixtures of cytokines and growth factors.

The starting cell population may be cultured during a time sufficient to reach an absolute number of HSCs of at least $10^4$, $10^5$, $10^6$, $10^7$, $10^8$, $10^9$ or more cells. In some embodiments, the starting cell population may be cultured during a time sufficient for a 10 to 50000 fold expansion of the HSPCs, for example between 100 and 10000 fold expansion. The cell population obtained after the attenuation may be used without further purification or may be subjected to further purification or selection steps. The cell population may then be washed to remove the attenuating agent and/or any other components of the cell culture and resuspended in an appropriate cell suspension medium for short term use or in a long-term storage medium, for example a medium suitable for cryopreservation.

The starting cells may be, for example, from a bone marrow donor or an individual with or at risk for depleted or limited blood cell levels. The subject may be a bone marrow donor prior to bone marrow harvesting or a bone marrow donor after bone marrow harvesting.

HSPC manipulation may be used as a supplemental treatment to chemotherapy or radiation therapy. For example, HSPCs may be isolated from a subject that will undergo chemotherapy, and after the therapy the cells are returned. Thus, the subject is a subject undergoing or expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy.

HSPCs or blood cells prepared by the methods described herein may be administered to such subjects in need of additional blood cells.

HSPCs and Pharmaceutical Compositions

According to any aspect of the present application, the HSPC may be a bone marrow derived HSPC.

In one aspect, the present application provides a rejuvenated HSPC, wherein an expression and/or function of Sphk2 has been attenuated in the HSPC.

In one aspect, the present application provides a rejuvenated HSPC, wherein an expression and/or function of Pdk3 has been enhanced in the HSPC.

In some embodiments, the HSPC is an aged HSPC, or a rejuvenated aged HSPC.

In an aspect, the present application provides an HSPC obtained, prepared, manipulated and/or treated by a method according to any aspect of the present application.

The HSPC may be an isolated HSPC, or a population of isolated HSPCs.

In some cases, the HSPC may have an attenuated expression and/or function of Sphk2. For example, the HSPC may be isolated or derived from a donor having attenuated expression and/or functions of Sphk2. As an example, the expression and/or function of Sphk2 of the donor may be attenuated, and then, one or more HSPCs may be obtained or isolated from such a donor, and provided/administered to the subject.

In some cases, the HSPC may have an enhanced expression and/or function of Pdk3. For example, the HSPC may be isolated or derived from a donor having an enhanced expression and/or function of Pdk3. As an example, the expression and/or function of Pdk3 of the donor may be enhanced, and then, one or more HSPCs may be isolated or obtained from such a donor, and provided/administered to the subject.

In some cases, the HSPC may be a rejuvenated HSPC, such as an aged HSPC that has been rejuvenated according to the present application.

The HSPC may comprise a hematopoietic stem cell (HSC), a hematopoietic progenitor cell (HPC), a long-term HSC (LT-HSC), a short-term HSC (ST-HSC), a multipotent progenitor cell (MPP), and/or a CD150 HSC.

In some cases, the biomarker of a hematopoietic stem cell (HSC) may comprise $CD34^+$, $CD38^-$. $CD45RA^-$, $CD90^+$, and/or $CD49f^+$.

In some cases, the biomarker of a multipotent progenitor cell (MPP) may comprise $CD34^+$, $CD38^-$, $CD45RA^-$, $CD90^+$, and/or $CD49f^-$. In some embodiments, the HSPCs of the present application may be resuspended in a pharmaceutically acceptable medium suitable for administration to a mammalian host, thereby providing a pharmaceutical composition.

The present application also provides a pharmaceutical composition comprising the HSPCs or HSPC population according to the present application, and optionally a pharmaceutically acceptable carrier.

The present application also provides use of the HSPCs or the pharmaceutical composition according to the present application in the manufacture of a medicament for preventing, treating and/or alleviating a disease or disorder related to hematopoietic dysfunction and/or hematopoietic injury in a subject in need thereof, and/or for promoting hematopoietic recovery after bone marrow transplantation in a subject in need thereof.

The pharmaceutical composition may contain a total amount of cells of at least $10^4$, at least $10^5$, at least $10^6$, at least $10^7$, at least $10^8$, at least $10^9$, or more cells, with between about 20-100%, for example between about 40-80% of total cells being HSPC cells.

The pharmaceutically acceptable carrier may comprise a material that is not biologically or otherwise undesirable, i.e., the material may be administered to a subject or cell, without causing undesirable biological effects or interacting in a deleterious manner with the other components of the pharmaceutical composition in which it is contained. The carrier or excipient is selected to minimize degradation of the active ingredient and to minimize adverse side effects in the subject or cell.

The Subjects

According to the present application, the subject may, for example, be a bone marrow donor or an individual with or at risk for depleted or limited blood cell levels. In some cases, the subject may be a bone marrow donor prior to bone marrow harvesting or a bone marrow donor after bone marrow harvesting.

In some cases, the subject may be a recipient of a bone marrow transplant. The subject may have limited bone marrow reserve such as elderly subjects or subjects previously exposed to an immune depleting treatment or myeloablative treatment such as chemotherapy, radiotherapy, and/or radiation from the environment.

The subject may have a decreased blood cell level or is at risk for developing a decreased blood cell level as compared to a control blood cell level. The control blood cell level may refer to an average level of blood cells in a subject prior to or in the substantial absence of an event that changes blood cell levels in the subject. An event that changes blood cell levels in a subject includes, for example, anemia, trauma, chemotherapy, bone marrow transplant, radiation therapy and/or radiation in the environment. For example, the subject may have anemia or blood loss due to, for example, trauma.

The subject may have depleted bone marrow related to, for example, congenital, genetic or acquired syndrome characterized by bone marrow loss or depleted bone marrow. Thus, the subject may be a subject in need of hematopoiesis. For example, the subject may be a bone marrow donor or is a subject with or at risk for depleted bone marrow.

The expression and/or function of Sphk2 may be attenuated, for example, before, at the same time, or after chemotherapy, radiation therapy or a bone marrow transplantation.

The expression and/or function of Pdk3 may be enhanced, for example, before, at the same time, or after chemotherapy, radiation therapy or a bone marrow transplantation.

In some embodiments, the subject is an aged subject.

In some embodiments, the subject has been subjected to chemotherapy.

In some embodiments, the chemotherapy comprises 5-fluorouracil.

In some embodiments, the subject has been subjected to radiation.

In some embodiments, the radiation comprises radiotherapy.

In some embodiments, the subject has been subjected to bone marrow transplantation.

The method and/or composition of the present application may be used as a supplemental treatment or therapy to chemotherapy and/or radiation therapy. For example, the subject may be a subject that has been subjected to, is undergoing or is expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy. Therefore, the methods of the present application may be applied to such subjects. In some cases, the subject has received bone marrow transplantation.

Methods and Systems of Candidate Agent Screening

In another aspect, the present application provides a method and/or a system for screening a candidate agent that may be used to prepare a composition (such as a pharmaceutical composition or a medicament).

The composition may be used for preventing, treating and/or alleviating the disease or disorder related to hematopoietic dysfunction and/or hematopoietic injury, according to the present application.

In some cases, the composition may be used for rejuvenating an HSPC (e.g., an aged HSPC).

The method may comprise determining/evaluating an ability of the candidate agent in attenuating an expression and/or function of Sphk2.

Alternatively, or additionally, the method may comprise determining/evaluating an ability of the candidate agent in enhancing an expression and/or function of Pdk3.

In some embodiments, the method comprises: 1) administering a candidate agent to a cell and/or an organism expressing Sphk2 (e.g., ex vivo, or in vitro); 2) evaluating an effect of said candidate agent on the expression and/or activity of the Sphk2; and 3) identifying the candidate agent attenuating the expression and/or activity of the Sphk2 as an agent that may be used for preparing the composition.

In some embodiments, the method comprises: 1) administering a candidate agent to a cell and/or an organism (e.g., ex vivo, or in vitro); 2) evaluating an effect of said candidate agent on an expression and/or activity of Pdk3 in the cell and/or organism; and 3) identifying the candidate agent enhancing the expression and/or activity of the Pdk3 as an agent that may be used for preparing the composition of the present disclosure.

The system may comprise an agent capable of detecting and/or revealing an attenuation of an expression and/or function of Sphk2, e.g., an antibody specifically binding to Sphk2 protein, a probe specifically recognizing Sphk2, a substrate of Sphk2, and/or one or more nucleic acid primers capable of specifically amplifying Sphk2.

Alternatively, or additionally, the system may comprise an agent capable of detecting and/or revealing an enhancement of an expression and/or function of Pdk3, e.g., an antibody specifically binding to Pdk3 protein, a probe specifically recognizing Pdk3, a substrate of Pdk3, and/or one or more nucleic acid primers capable of specifically amplifying Pdk3.

Attenuation of Sphk2

The attenuation may be revealed or characterized by a reduced level (e.g., a reduction of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds, at least about 6 folds, at least about 7 folds, at least about 8 folds, at least about 9 folds, at least about 10 folds or more) of Sphk2 expression and/or function, for example, as a result of an intervention or manipulation.

According to any aspect of the present application, the expression and/or function of the Sphk2 may be attenuated by inhibiting an expression and/or function of the Sphk2 gene, and/or inhibiting an expression and/or function of the Sphk2 protein.

In some cases, the expression and/or function of Sphk2 may be attenuated genetically, e.g., by knocking out or knocking down the Sphk2 gene. Alternatively or additionally, the expression and/or function of Sphk2 may be attenuated with an inhibitor of Sphk2.

For example, the attenuation may be achieved with a small interference RNA (siRNA) molecule capable of down-regulating the expression of Sphk2, an antisense oligonucleotide capable of down-regulating the expression of Sphk2, an antibody capable of inhibiting the activity of Sphk2, and/or a small molecule inhibitor of Sphk2.

Design of antisense oligonucleotides which can be used to efficiently inhibit the Sphk2 protein expression must be effected in a way that such oligonucleotides specifically binds the designated mRNA within cells in a way which inhibits translation thereof. Sequence suitable for use in design and synthesis of antisense oligonucleotides which specifically bind to Sphk2 mRNA, genomic DNA and/or its promoter or other control sequences are available in published sequence of Sphk2, in particular human Sphk2. In addition, algorithms for identifying sequences with the highest predicted binding affinity for their target mRNA based on thermodynamic cycle that accounts for the energetics of structural alterations in both the target mRNA and the oligonucleotides are also available.

For example, the attenuation may be achieved with crispr-cas9 mediated gene editing to repress, block or disrupt Sphk2 gene expression.

In some cases, the expression and/or function of the Sphk2 may be attenuated with a Sphk2 inhibitor. The Sphk2 inhibitor may be a small molecule inhibitor.

In some embodiments, the Sphk2 inhibitor may be as described in WO2006138660A2, which is incorporated herein by reference in its entirety.

In some embodiments, the Sphk2 inhibitor is 3-(4-chlorophenyl)-N-(pyridinyl-4-ylmethyl) adamantane-1-carboxamide, which is also known as ABC294640, or a pharmaceutically acceptable salt thereof.

In some embodiments, the Sphk2 inhibitor comprises a compound of formula (I) or a pharmaceutically acceptable salt thereof:

(I)

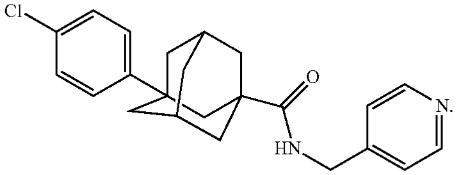

In some embodiments, the Sphk2 inhibitor comprises a compound of formula (II) or a pharmaceutically acceptable salt thereof:

(II)

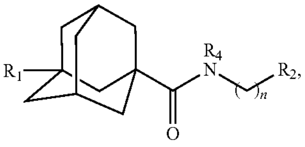

wherein:

$R_1$ is phenyl, or a phenyl substituted with a halogen;

$R_2$ is aryl, heteroaryl, or a substituted aryl or heteroaryl, such as a 4-pyridine;

$R_4$ is H or alkyl; and n is an integer of at least 1.

In some embodiments, the Sphk2 inhibitor comprises a compound of formula (II) or a pharmaceutically acceptable salt thereof:

(II)

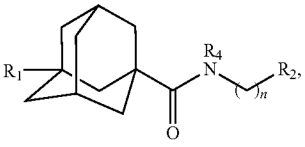

wherein:

$R_1$ is phenyl, 4-chlorophenyl or 4-fluorophenyl;

$R_2$ is 4-pyridyl, optionally substituted;

$R_4$ is H or alkyl; and n is 1 or 2.

In some embodiments, the Sphk2 inhibitor comprises a compound of formula (III) or a pharmaceutically acceptable salt thereof:

(III)

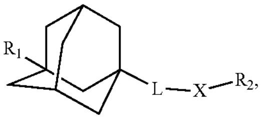

wherein:

L is a bond or an optionally substituted alkyl;

X is —C(O)N($R_4$)—;

$R_1$ is aryl (e.g., phenyl), heteroaryl, substituted aryl or substituted heteroaryl, in some cases, $R_1$ is aryl (e.g., phenyl) or heteroaryl substituted with a halogen (such as Cl), in some cases, $R_1$ is phenyl, 4-chlorophenyl or 4-fluorophenyl;

$R_2$ is aryl, -alkylaryl, heteroaryl, -alkyl-heteroaryl, substituted aryl, substituted -alkylaryl, substituted heteroaryl, or substituted -alkyl-heteroaryl; and $R_4$ is H or alkyl, such as ($C_1$-$C_6$) alkyl.

In some embodiments of the compounds of structural formula (III) as described above, $R_1$ is optionally substituted aryl, for example, phenyl. In some embodiments, the phenyl is unsubstituted. In other embodiments, the phenyl is substituted with a halogen (e.g., monohalo-substituted at the 4-position). For example, the halogen substituent may be Cl or F.

In some embodiments of the compounds of structural formula (III) as described above, $R_2$ is aryl or -alkylaryl.

In some embodiments of the compounds of structural formula (III) as described above, $R_2$ is heteroaryl or -alkylheteroaryl. In some cases, the alkyl is a methyl. In some cases, the heteroaryl is a pyridine. In some cases, $R_2$ is a -methyl-pyridine.

Enhancement of Pdk3

The enhancement may be revealed or characterized by an increased level (e.g., an increase of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 1 fold, at least about 1.5 folds, at least about 2 folds, at least about 2.5 folds, at least about 3 folds, at least about 4 folds, at least about 5 folds, at least about 6 folds, at least about 7 folds, at least about 8 folds, at least about 9 folds, at least about 10 folds or more) of Sphk2 expression and/or function, for example, as a result of an intervention or manipulation.

In some cases, the enhanced expression and/or function of Pdk3 may be directly or indirectly caused by an attenuated expression and/or function of Sphk2.

In some embodiments of any aspect of the present application, the expression and/or function of the Pdk3 is enhanced at least partially by enriching H3K9 acetylation in a promoter region of the Pdk3 gene.

In some cases, enhancement of Pdk3 expression and/or function may be achieved by increasing Pdk3 gene transcriptional activity. e.g., the Pdk3 gene activation can be achieved by small molecules or biological activators hereof.

In some cases, enhancement of Pdk3 expression and/or function may be achieved by e.g., overexpressing Pdk3 or a functional fragment thereof.

In some cases, enhancement of Pdk3 expression and/or function may be achieved by e.g., providing Pdk3 protein or a functional fragment thereof.

The technical solutions of the present application will be further illustrated in connection with the examples.

EXAMPLES

Materials and Methods

Animals

B6N.129S6-Sphk1tm1Rlp/J (Sphk1Δ/Δ) and B6N.129S6-Sphk2tm1Rlp/J (Sphk2Δ/Δ) mice were obtained from the Jackson Laboratory. To achieve tissue-specific deletion of Sphk2, the $Sphk2^{flox/flox}$ mice were crossed with Vav-Cre transgenic mice. $Sphk2^{flox/flox}$ mice was constructed by Cyagen Biosciences Inc. Briefly, linearized targeting vector was electroporated into embryonic stem (ES) cells and positive clones were identified by Southern blotting and injected into C57BL/6 blastocysts followed by chimera production to obtain germline transmission. The Frt-flanked Neo cassette was subsequently removed by mating with Flpe mice. 2-month-old mice or more than 20-month old for aging we used as indicated. 5 FU (Sigma-Aldrich) was injected once or once a week for survival curve as indicated in the tail vein at 150 μg/g body weight. Sphk2 inhibitor ABC294640 (Target Molecule Corp T6750) and PDK inhibitor Sodium dichloroacetate (DCA) (Selleck Chemicals S8615) were intraperitoneal injected at 25 mg/kg. All mouse strains used had a C57BL/6J genetic background. Animals were randomly included in the experiments according to genotyping results as a mix of male and female. All animal experiments were performed according to protocols approved by the institutional animal care and use committee.

Flow Cytometry

For phenotype analysis and hematopoietic purification, hematopoietic cells were harvested from bone marrow (femur and tibia). For cell surface phenotyping, a lineage cocktail (Lin, phycoerythrin (PE)-Cy5) was used, including anti-CD3 (145-2C11), anti-CD4 (RM4-5), anti-CD8 (53-6.7), anti-Mac-1 (M1/70), anti-Gr1 (RB6-8C5), anti-B220 (RA3-6B2), anti-IgM (11/41) and anti-TER119 (TER-119) (100 ng antibody cocktail per million bone marrow cells, Biolegend). Monoclonal antibodies to SCA1 (D7, Biolegend), c-KIT (2B8, Biolegend), FLK2 (A2F10, Biolegend), CD34 (RAM34, eBioscience), CD48 (HM48-1, Biolegend), CD41 (MWReg30, eBioscience), CD150 (TC15-12F12.2, BioLegend), CD16/32 (93, Biolegend), IL-7R (A7R34, Biolegend) (all used as 50 ng per million bone marrow cells) were also used where indicated.

For phenotype analysis of human cord blood HSCs (CB-HSCs, $CD34^+$CD38-CD45RA-$CD49f^+$), cell surface phenotyping, anti-hCD34 (581), anti-hCD38 (HIT2), anti-hCD45RA (HI100) and anti-hCD49f (GOH3) (100 ng antibody cocktail per million cord blood cells, Biolegend) were used.

For lineage analysis of peripheral blood, monoclonal antibodies to CD45.1 (A20, eBioscience), CD45.2 (104, Biolegend), CD3, B220, Mac-1 and Gr1 were used.

Or, in example 14, for lineage analysis of peripheral blood, monoclonal antibodies to anti-hCD45 (HI-30, eBioscience), anti-mCD45 (30-F11, Biolegend), anti-hCD33 (human myeloid cells) (WM53, eBioscience), anti-hCD19 (human B cells) (HIB19, eBioscience), anti-hCD3 (human T cells) (UCHT1, eBioscience) were used.

For cell cycle, DNA damage, the cells were fixed, permeabilized and stained by anti-Ki67 (16A8, Biolegend).

7-aminoactinomycin D (7-AAD) (A1310, Life technologies) was used to exclude dead cells.

The cells were further incubated with 0.1 ug/uL DAPI (1306, Thermo Scientific) for 30 min at room temperature. For apoptosis and ROS analysis, the cells were stained by AnnexinV or DCFDA (D6883, Sigma-Aldrich).

Cell sorting and analysis were performed using an Attune NxT analyzer (Thermo Fisher Scientific) or InFlux Cell Sorter (BD Biosciences). Data analysis was performed using FlowJo software.

Transplantation $2.0\times10^5$ CD45.2 bone marrow cells and $2.0\times10^5$ CD45.1 rescue bone marrow cells were transplanted into lethally irradiated CD45.1 recipients. Adult recipient mice (CD45.1) were irradiated with an Orthovoltage X-ray source delivering approximately in two equal doses of 4.5 Gy at least 3 hours apart. For secondary or tertiary transplantation, bone marrow cells from each recipient were injected into one or two irradiated new recipient mouse ($1\times10^6$ per recipient, depending on the number of recipients) during each round of transplantation.

Repopulation Assay

Every 4 weeks after transplantation, peripheral blood was collected from the submandibular vein. Hematopoietic repopulation was measured from donor-derived blood cells (CD45.2) or human-derived blood cells (human CD45).

Colony Assays

Bone marrow cells were diluted to the indicated concentration in PBS and were seeded into methylcellulose medium M3434 (StemCell Technologies) for CFU-GM, CFU-GEMM, and BFU-E colony formation assays according to the manufacturer's Immunostaining Purified HSCs were fixed by 4% paraformaldehyde (PFA) for 30 min. Anti-Sphk2 (rabbit, 1:100, 17096-1-1AP, Proteintech) or anti-phospho-PDHE1-A type I (Ser293) (rabbit, 1:50, ABS204, Merck Millipore) or anti-S1P antibodies (mouse, 1:50, Z-P300, Lpath, Incorporated)[37] were used. For S1P staining, HSCs were further treated with 1 mM EDTA pH8 for 8 hours as previous described[38]. Secondary staining was done with donkey anti-rabbit AF488 (1:500, A21206, Thermo Scientific) and donkey anti-mouse AF488 (1:300, A21202, Thermo Scientific). For high-resolution three-dimensional images, z-stack collected images from Nikon C2plus, or Nikon AIR N-SIM/N-STORM microscopy were analyzed with Imaris software (Bitplane) and ImageJ (National Institutes of Health).

Western Blotting

The same number of cells from each population to be analyzed were sorted into PBS with 2% FBS. The cells then were washed with PBS and Lysised by RIPA. Equal amounts of protein extracts were fractionated by 12.5% SDS-PAGE and transferred to a PVDF membrane (IPVH00010, Merck Millipore). After blocked with 5% non-fat milk in Tris-buffered saline with Tween-20 (TBST, pH 7.6) for 1 h at room temperature, the membranes were incubated with primary antibodies anti-phospho-PDHE1-A type I (Ser293) (rabbit, 1:1000, ABS204, Merck Millipore), anti-Sphk2 (rabbit, 1:1000, 17096, Proteintech), anti-PDK3 (rabbit, 1:1000, 4970s, Proteintech), or anti-βactin (rabbit, 1:1000, 2118, Cell Signaling Technology), or with primary antibodies anti-PDK3 (rabbit, 1:1000, 12215, Proteintech), anti-β-actin (rabbit, 1:1000, 4970s, Cell Signaling Technology), overnight at 4° C. and then incubated with secondary antibodies (rabbit, 1:10,000, W401B, Promega) for 1 h at room temperature, which was detected by exposure to x-ray film, or by digital imaging with a charge-coupled device camera system (Odyssey Fc). The images shown are representative of images from at least three experiments.

Knock-Down of Pdk3 in HSCs

The siRNAs (GGACCTGCATCATGAACAATG, SEQ ID NO. 1) against mouse Pdk3 were cloned into lentivirus pLKO.1-puro vector to infect bone marrow cells. The infected bone marrow cells were further treated by puromycin (A1113803, Thermo Fisher) at 0.85 μg/ml for 7 days.

PDK3 Overexpression and Transplantation

PDK3 was cloned into Psico-EFα-IRES2-EGFP. PDK3 overexpression and control lentivirus were prepared by HEK293T transfected by Psico-EFα-IRES2-EGFP together with pSPAX2, pM2.G packaging vectors. Bone marrow cells were infected with PDK3 overexpression or control lentivirus and further selected by 0.85 μg $ml^{-1}$ puromycin (A1113803, Thermo Fisher). After culture for 7 days, 10,000 PDK3 overexpression or control HSCs were purified and transplanted into lethally irradiated CD45.1 recipient mice together with $2\times10^5$ CD45.1 competitor cells. Adult recipient mice (CD45.1) were irradiated with an Orthovoltage X-ray source delivering approximately in two equal doses of 4.5 Gy at least 3 hours apart. No mice were excluded unless they died during the 16-week-observations. All animal experiments were performed according to protocols approved by the institutional animal care and use committee.

Low Input RNA Seq

Low input RNA seq was performed according to published scRNA seq protocols with modifications (Tang, 2009; Tang, 2010). FACS-sorted 1000 cells (2-3 ⌊L) were transferred into 25 ⌊l cell lysis buffer prepared as follows: 0.9×PCR buffer II, 1.35 mM MgCl2, 0.45% NP40, 4.5 mM DTT, 0.36 U ⌊l-1 RNase inhibitor (ThermoFisher, EN0581), 12.5 nM UP1 primer, 0.045 mM dNTP), following reverse transcription with RT mix prepared as follows: 14.4 U ⌊l-1 Superscript III reverse transcriptase (Invitrogen, 18080-044), 0.48 U l-1 RNase inhibitor, 0.07 U ⌊l-1 T4 gene 32 protein (NEB, #M0300L) as previously described (Tang, 2010). cDNA purified with AMPure XP beads (Beckman Coulter, A63881) was used to perform poly A tailling, then one round PCR enrichment with 13 cycles of amplification as described (Tang, 2010). Enriched cDNA was quantified using Qubit dsDNA HS Assay Kit after purification. TruePrep™ DNA library Prep Kit V2 (Vazyme, TD503) was used to prepare RNA seq library following the manufacturer's protocol. Libraries were sequenced as pair-end 150 bp using HiSeq X10. Three independent biological replicates were included for each type.

RNA-Seq Data Processing

RNA-seq reads were aligned to mouse genome mm10 and gene annotation from the Ensembl database. For read alignment and expression quantification, low quality reads were removed and the adaptor sequences were trimed by Trim Galore (v0.6.2). Then, the remaining pair-end reads were mapped to the reference genome by STAR version 2.6.1d with ENCODE options. The uniquely mapped reads were counted by HTSeq version 0.10.0, and normalized by trimmed mean of M values (TMM), and transformed to reads per kilobases per million reads (RPKM) by edgeR version 3.24.3. Low abundant genes were removed with an expression cutoff of RPKM≥1 in at least one sample. The different express genes were detected by edgeR. Genes were considered differentially expressed when the overall p value<0.05 and fold change is above 2.0.

ChIP-Seq Data Processing

Chip-seq reads were aligned to mm10 genome by Bowtie2 (v2.3.4.3) after low quality reads removed and adaptor sequences trimed by Trim Galore (v0.6.2). To examine the reproducibility of the Chip-seq experiments, the Pearson correlation of H3K9ac signals around gene transcription start sites (TSS)±5 Kb regions between replicates were calculated and scatter plots were generated by deepTools, and two biological replicates in each sample were pooled for subsequent analysis. To visualize the tracks around interesting genes in Intergrative Genome Visualization (IGV), we normalized each merged alignment bam file to the GRCm38 genome size and converted them to bigwig format. To generate H3K9ac ChIP-seq heatmap around genomic regions, we calculated scores per 10-bp bin in the continuous TSS±5 Kb regions of RefSeq genes (mm10) using deepTools. H3K9ac peaks in each merged sample were called by MACS2 (v2.1.2) with default parameters except "-g mm -p 0.001 --keep-dup all". Normalized mean concentration (Conc) was calculated by DiffBind and peaks were annotated by ChIPseeker. Differentially Enriched Peaks were selected among peaks annotated as promoters and up-regulated peaks were selected if Conc (KO)—Conc (WT)≥1, and down-regulated peaks were selected if Conc (WT)—Conc (KO)≥1. Heatmap of differentially enriched peaks were generated in R.

Stem Cell Culture and Transplantation

Human cord blood cells ($2\times10^5$) were cultured in 96-round-well plate with Stem Span media (9650, Stem Cell Technologies) supplemented with SCF (10 ng per ml), TPO (20 ng per ml) for two weeks. The culture media was supplemented with vehicle or ABC294640 (1 μM, Target Molecule Corp T6750). After culture for two weeks, the culture product was transplanted into irradiated (2Gy) 6-12 weeks old NSG mice via the tail. No mice were excluded unless they died during the 16-week-observations. All animal experiments were performed according to protocols approved by the institutional animal care and use committee.

Statistical Analyses

Data are expressed as means±s.d. For all experiments except determination of survival, data were analyzed by Student's t test, and differences were considered statistically significant if $P<0.05$. The survival of the two groups were analyzed using a log-rank test, and differences were considered statistically significant if $P<0.05$. Differences were considered statistically significant if $P<0.05$. * $P<0.05$,  $P<0.01$, * $P<0.001$.

Example 1

Both Sphk1 and Sphk2 knockout mice were employed in this example. As shown in FIG. 1, there was an increase in the number of long-term HSCs (LT-HSCs, $CD34^-Flk^-Lin^-Sca1^+c\text{-}KIT^+$, about 2.3-fold), short-term HSCs (ST-HSCs, $CD34^-Flk^+Lin^-Sca1^+c\text{-}KIT^+$, about 1.9-fold), multipotent progenitor cells (MPPs, $CD34^+Flk^+Lin^-Sca1^+c\text{-}KIT^+$, about 1.7-fold) and CD150 HSCs ($CD150^+CD48^-Lin^-Sca1^+c\text{-}KIT^+$, about 2.5-fold) in Sphk2 deficient mice but not in Sphk1 deficient mice.

Figure 2:
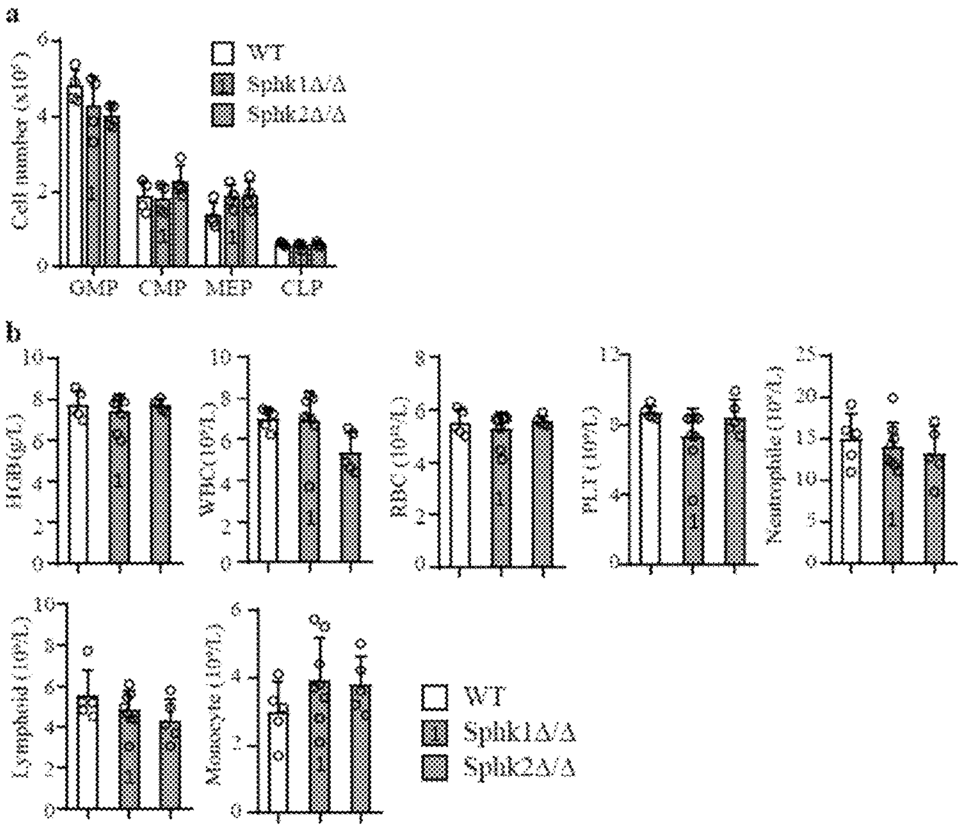
FIG. 2 illustrates that Sphk2 attenuation does not affect progenitor and mature blood cell numbers. (a) the absolute number of progenitors (GMP, CMP, MEP, CLP) in the bone marrow from Sphk1Δ/Δ, Sphk2Δ/Δ or control mice (n=4 mice per group). (b) The HGB, WBC, RBC, PLT, neutrophil, lymphoid and monocytes in peripheral blood from Sphk1Δ/Δ (n=8 mice), Sphk2Δ/Δ (n=5 mice) or control mice (n=5 mice). granulocyte-macrophage progenitor (GMP), common myeloid progenitor (CMP), megakaryocyte-erythroid progenitor (MEP), common lymphoid progenitor (CLP). hemoglobin (HGB), White blood cells (WBC), Platelets (PLT). Data represent mean±s.d.
Figure 3:
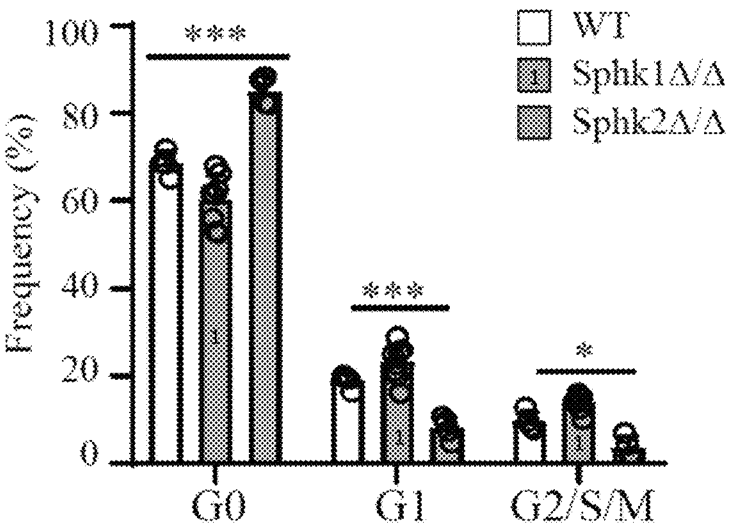
FIG. 3 illustrates the cell cycle analysis of CD150 HSCs in bone marrow from Sphk1Δ/Δ (n=4 mice), Sphk2Δ/Δ (n=8 mice) or control mice (WT) (n=4 mice).

As shown in FIG. 2, Hematopoietic cell pool expansion was restricted to HSPCs and was not evidenced in other progenitor populations in bone marrow and mature blood cells including platelet number in peripheral blood. The increased HSC numbers in Sphk2 deficient mice was not due to HSC activation because cell cycle analysis of CD150 HSCs revealed an increase in G0-phase fraction (from 68.4% to 84.9%) and concomitant decrease in the G1-phase fraction (from 18.7% to 8.1%) and the G2/S/M-phase fraction (from 9.6% to 3.6%) in Sphk2 deficient mice but not in Sphk1 deficient mice compared to control (FIG. 3).

Figure 4:
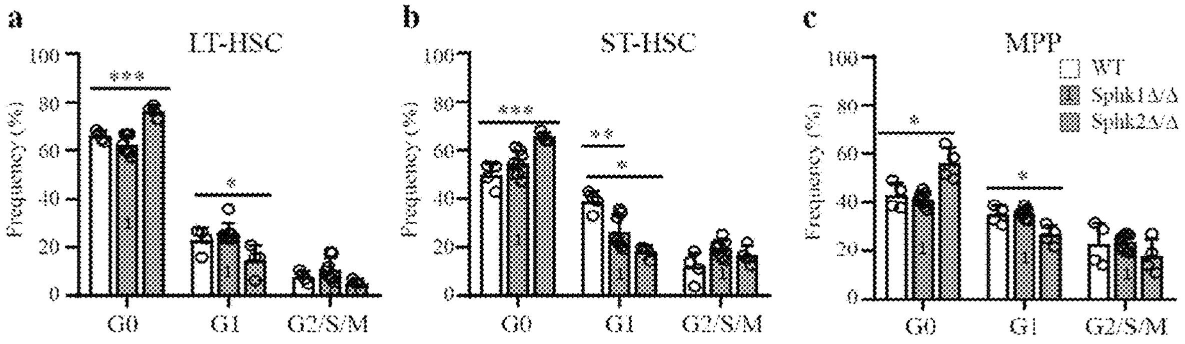
FIG. 4 illustrates cell cycle analysis of LT-HSC, ST-HSC and MPP in the bone marrow from Sphk1Δ/Δ (n=8 mice), Sphk2Δ/Δ (n=4 mice) or control mice (WT) (n=4 mice). Data represent mean±s.d. Two-tailed Student's t-tests were used to assess statistical significance. *$P<0.05$, $P<0.01$, *$P<0.001$.
Figure 5:
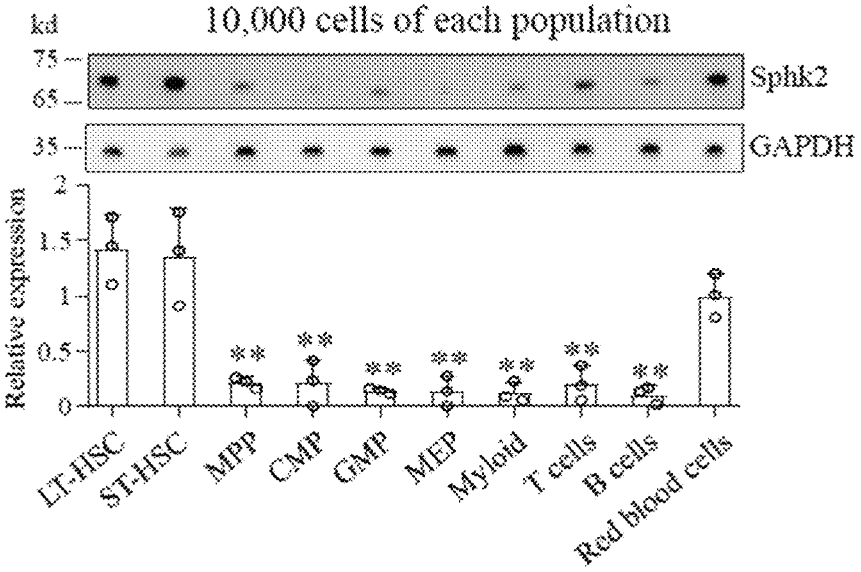
FIG. 5 illustrates Western blot analyses and quantification of relative Sphk2 protein expression of 10,000 cells from each hematopoietic-cell population from wide type C57BL/6J mice (n=3 mice).
Figure 6:
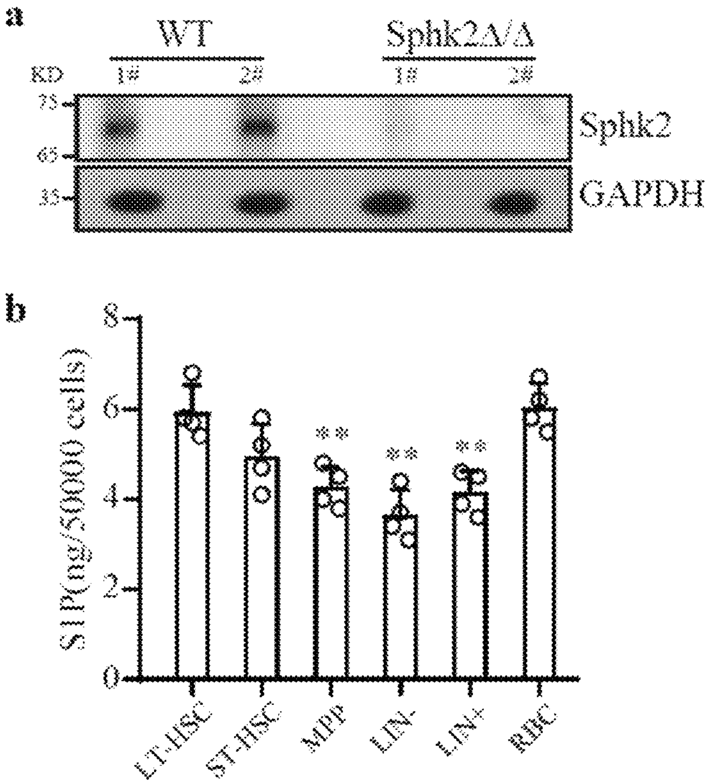
FIG. 6 illustrates that HSCs express Sphk2 and generate high level S1P. (a) Western blot analyses of Sphk2 protein expression in 10,000 HSCs from Sphk2Δ/Δ or WT control mice. 1 #, 2 # indicated two individual mice. (b) S1P levels as determined by targeted metabolomics assay in HSCs and red blood cells from C57 mice (n=4 mice). Data represent mean±s.d. Two-tailed Student's t-tests were used to assess statistical significance. **$P<0.01$.

The increase of G0-phase faction was also observed in LT-HSCs, ST-HSCs and MPPs in Sphk2 deficient mice (FIG. 4). Interestingly, it was found that HSCs had the highest expression level of Sphk2 among hematopoietic cells. Sphk2 protein level in HSCs was even higher than in red blood cells, which are one of the main S1P producers (FIG. 5 and FIG. 6).

The increase of HSC numbers and HSC quiescence were similar in Vav-Cre; $Sphk2^{f/f}$ mice, which rules out the potential influence from non-hematopoietic tissues (FIG. 7).

It was also found that Sphk2 was more abundant in the nucleus than the cytoplasm in HSCs (FIG. 8). Sphk2 generated more nuclear S1P than Sphk1 in HSCs (70% and 30% reduction of nuclear S1P in Sphk2 deficient HSCs and Sphk1 deficient HSCs, respectively); however, Sphk1 generated more cytoplasmic S1P than Sphk2 in HSCs (79% and 34% reduction in Sphk1 deficient HSCs and Sphk2 deficient HSCs respectively) (FIG. 9), indicating that Sphk2 and S1P generated by Sphk2 might have a nuclear function, such as histone acetylation in HSCs.

Example 2

Figure 10:
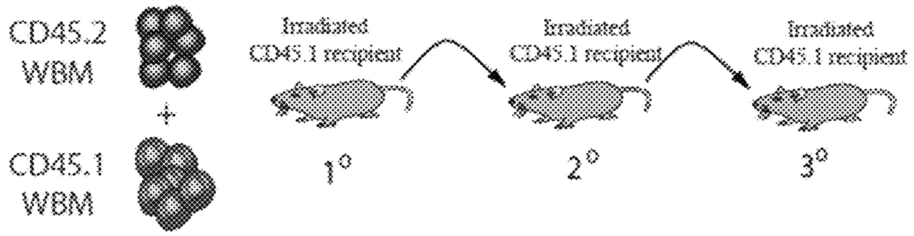
FIG. 10 illustrates a scheme for quantification of functional HSCs by transplantation assay. $2\times10^5$ bone marrow cells from Sphk1Δ/Δ, Sphk2Δ/Δ or control mice were transplanted into irritated mice along with $2\times10^5$ recipient bone marrow cells. $1\times10^6$ bone marrow cells from primary or secondary recipient mice were transplanted into irritated mice in secondary transplantation or tertiary transplantation respectively.
Figure 11:
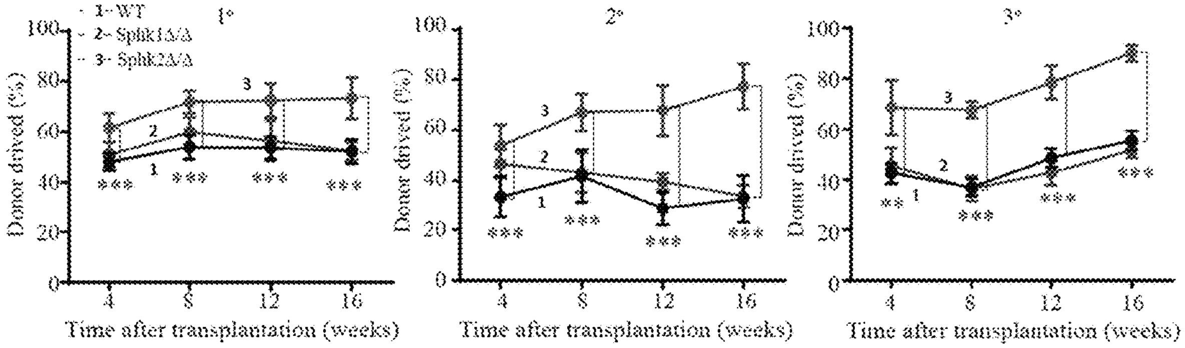
FIG. 11 illustrates PB analysis for total engrafted donor cells at the indicated number of weeks after transplantation (primary transplantation WT n=10 mice, Sphk1Δ/Δ n=10 mice, Sphk2Δ/Δ n=8 mice per group; secondary transplantation WT n=9 mice, Sphk1Δ/Δ n=7 mice, Sphk2Δ/Δ n=7 mice per group; tertiary transplantation WT n=7 mice, Sphk1Δ/Δ n=8 mice, Sphk2Δ/Δ n=6 mice per group).

$2\times10^5$ whole bone marrow cells from Sphk1 or Sphk2 deficient mice or from control donors were transplanted into irradiated wild-type recipients along with $2\times10^5$ recipient bone marrow cells (FIG. 10). The Sphk2 but not Sphk1 deficient bone marrow cells gave significantly higher levels of reconstitution ($CD45.2^+$cells) than control cells throughout the 16-weeks observation (1.4-fold increase at 16 weeks) (FIG. 11).

Figure 14:
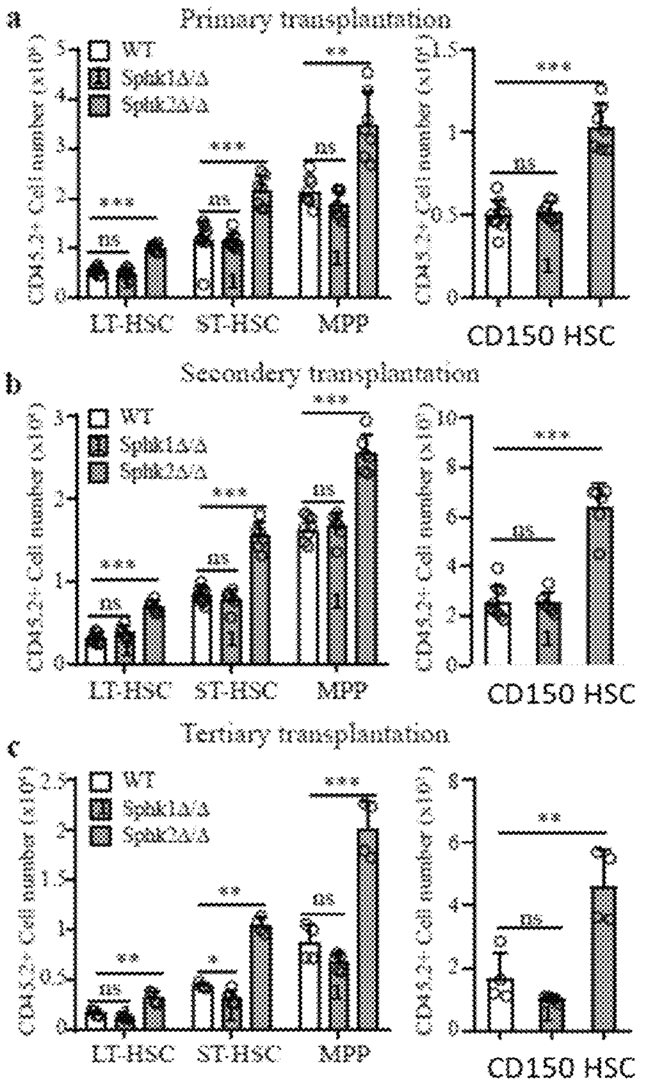
FIG. 14 illustrates that Sphk2 inhibition increases donor derived HSPC pool in recipients after bone marrow transplantation. The absolute numbers of donor derived HSPCs ($CD45.2^+$; LT-HSC, ST-HSC, MPP and CD150HSC) in the bone marrow were analyzed at 16 weeks after transplantation. (primary transplantation WT n=10 mice, Sphk1Δ/Δ n=10 mice, Sphk2Δ/Δ n=8 mice per group; secondary transplantation WT n=9 mice, Sphk1Δ/Δ n=7 mice, Sphk2Δ/Δ n=7 mice per group; tertiary transplantation WT n=7 mice, Sphk1Δ/Δ n=8 mice, Sphk2Δ/Δ n=6 mice per group). Data represent mean±s.d. Two-tailed Student's t-tests were used to assess statistical significance. *P<0.05, P<0.01, *P<0.001.
Figure 15:
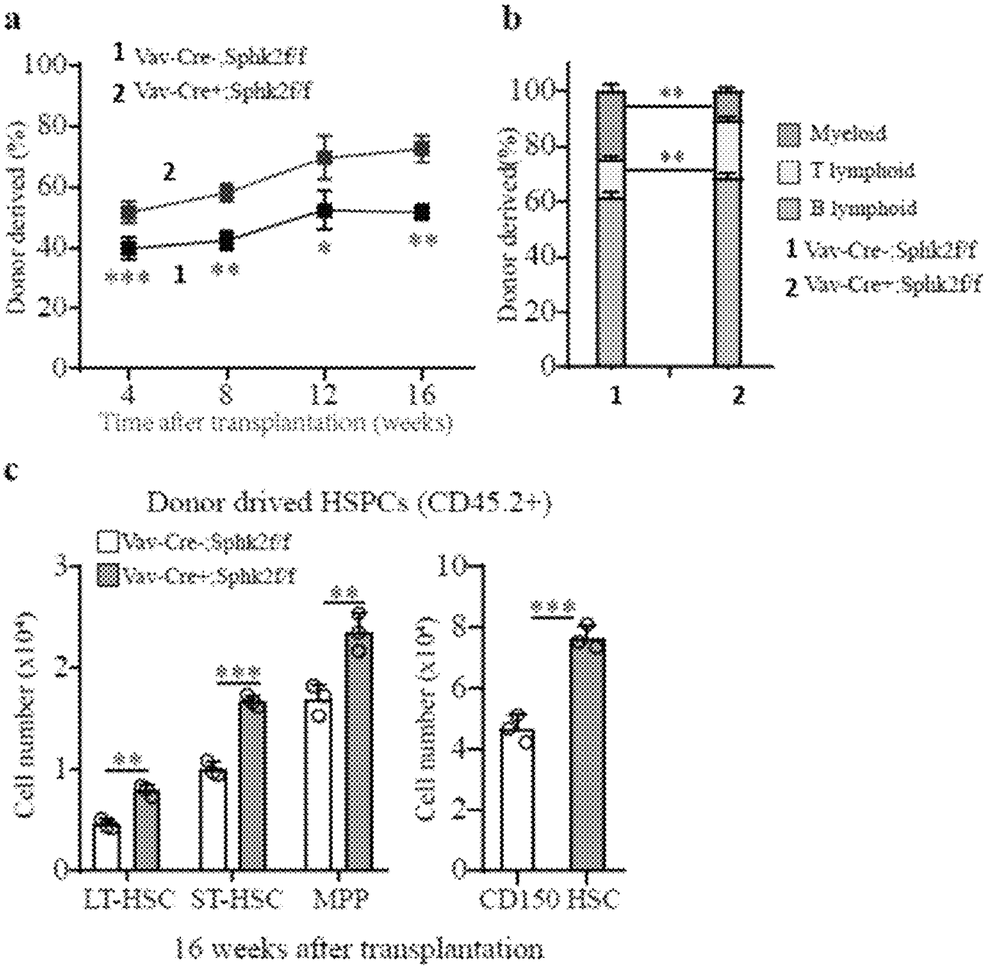
FIG. 15 illustrates that conditional deletion of Sphk2 in hematopoietic cells promotes HSC function. Quantification of functional HSCs by transplantation assay. $2\times10^5$ bone marrow cells from Vav-Cre; $Sphk2^{flox/flox}$ mice were transplanted into irritated mice along with $2\times10^2$ recipient bone marrow cells. (a, b) PB analysis for total engrafted donor cells at the indicated number of weeks after transplantation (a) and the percentage of donor-derived B, T and myeloid lineage cells at 16 weeks after transplantation (b) ($Cre^-$ n=6 mice, $Cre^+$ n=5 mice). (c) The absolute numbers of donor derived HSPCs ($CD45.2^+$; LT-HSC, ST-HSC, MPP and CD150HSC) in the bone marrow were analyzed at 16 weeks after transplantation. (n=3 mice). Data represent mean±s.d. Two-tailed Student's t-tests were used to assess statistical significance. *P<0.05, P<0.01, *P<0.001.

To assess the long-term self-renewal potential of HSPCs, $1\times10^6$ whole bone marrow cells from each recipient were serially transplanted into an irradiated mouse during each round of transplantation (FIG. 10). In secondary and tertiary recipient mice, significantly higher levels of reconstitution from the Sphk2 but not Sphk1 deficient bone marrow cells than from control donor cells were observed (2.4-fold and 1.6-fold increase at 16 weeks in secondary and tertiary transplantation, respectively) (FIG. 11). Sphk2 deficient donor cells gave more donor derived HSPCs in recipients during 3 rounds of transplantation observations (FIG. 14). Consistently, the increased HSC function was also evidenced in $Vav\text{-}Cre^+$; $Sphk2^{f/f}$ mice than $Vav\text{-}Cre^-$; $Sphk2^{f/f}$ littermates, which demonstrated that Sphk2 cell autonomously regulates HSC function (FIG. 15).

Figure 16:
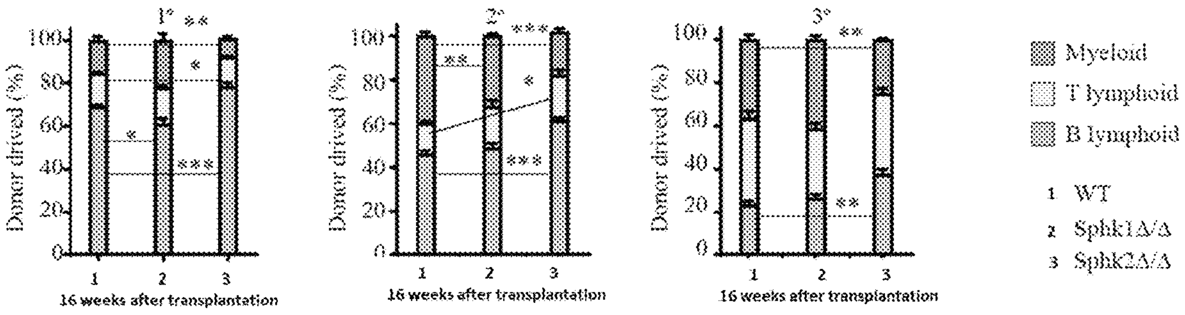
FIG. 16 illustrates the percentage of donor-derived B, T and myeloid lineage cells at 16 weeks after transplantation (primary transplantation WT n=10 mice, Sphk1Δ/Δ n=10 mice, Sphk2Δ/Δ n=8 mice per group; secondary transplantation WT n=9 mice, Sphk1Δ/Δ n=7 mice, Sphk2Δ/Δ n=7 mice per group; tertiary transplantation WT n=7 mice, Sphk1Δ/Δ n=8 mice, Sphk2Δ/Δ n=6 mice per group).
Figure 17:
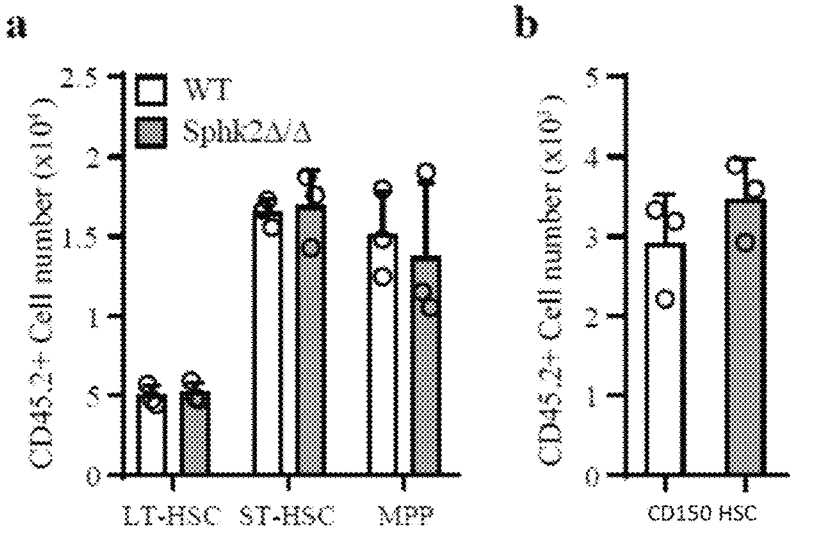
FIG. 17 illustrates that Sphk2 inhibition does not affect HSC homing. Quantification of HSC number homed to bone marrow after transplantation. $5\times10^6$ bone marrow cells from Sphk2Δ/Δ or littermates were transplanted into irritated mice. The absolute numbers of donor HSPCs ($CD45.2^+$; LT-HSC, ST-HSC, MPP and CD150HSC) in the recipient bone marrow were analyzed at 18 hours after transplantation. (n=3 mice). Data represent mean±s.d. Two-tailed Student's t-tests were used to assess statistical significance. *P<0.05, P<0.01, *P<0.001.

It has also been observed that Sphk2 deficient bone marrow cells gave more lymphoid cells than myeloid cells during serious transplantations (FIG. 16). Additionally, Sphk2 deletion did not affect HSC homing (FIG. 17), which also suggested that Sphk2 might have a S1P receptor independent function for HSC regulation.

Together, these results demonstrated that Sphk2 attenuation promotes HSPC expansion during homeostasis.

Example 3

Figure 18:
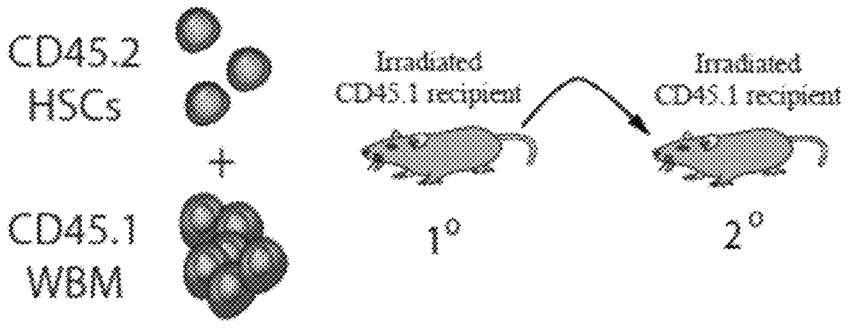
FIG. 18 illustrates a scheme for quantification of HSC self-renewal potential by transplantation assay. 100 purified CD150HSCs from Sphk2Δ/Δ or control mice were transplanted into irritated mice along with $2\times10^5$ recipient bone marrow cells. $1\times10^6$ bone marrow cells from primary recipient mice were transplanted into irritated mice in secondary transplantation.
Figure 19:
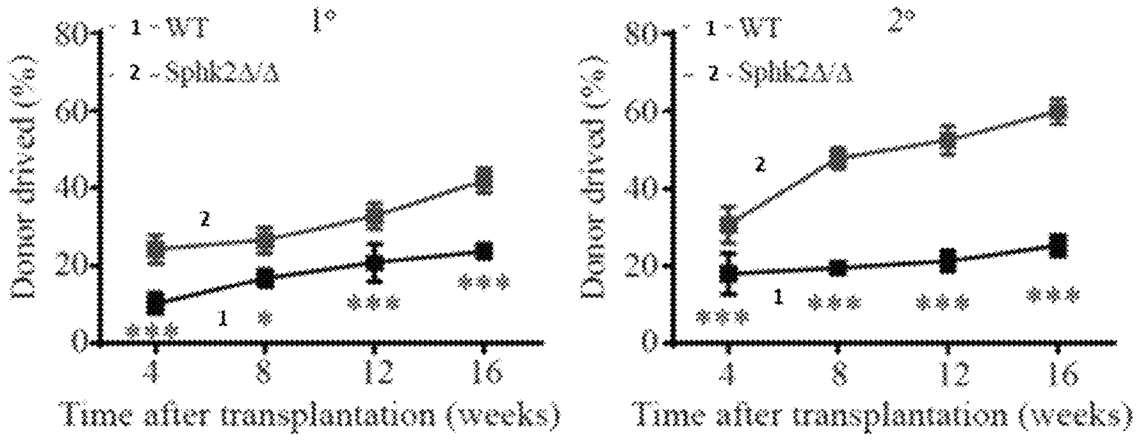
FIG. 19 illustrates PB analysis for total engrafted donor cells at the indicated number of weeks after transplantation (primary transplantation WT n=8 mice, Sphk2Δ/Δ n=6 mice per group; secondary transplantation WT n=8 mice, Sphk2Δ/Δ n=8 mice per group). 1° primary transplantation, 2° secondary transplantation. *P<0.05, P<0.01, *P<0.001.
Figure 21:
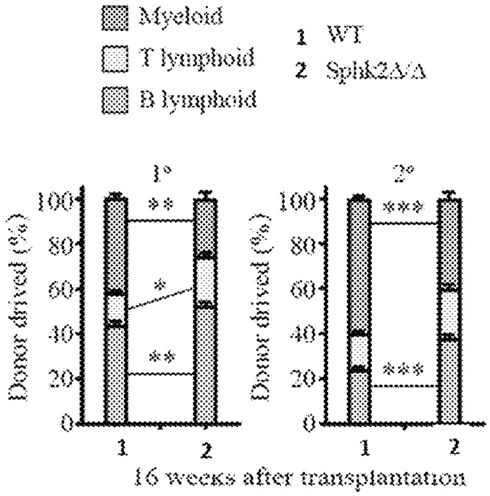
FIG. 21 illustrates the percentage of donor-derived B, T and myeloid lineage cells at 16 weeks after transplantation (primary transplantation WT n=8 mice, Sphk2Δ/Δ n=6 mice per group; secondary transplantation WT n=8 mice, Sphk2Δ/Δ n=8 mice per group). 1° primary transplantation, 2° secondary transplantation. *P<0.05, P<0.01, *P<0.001.
Figure 22:
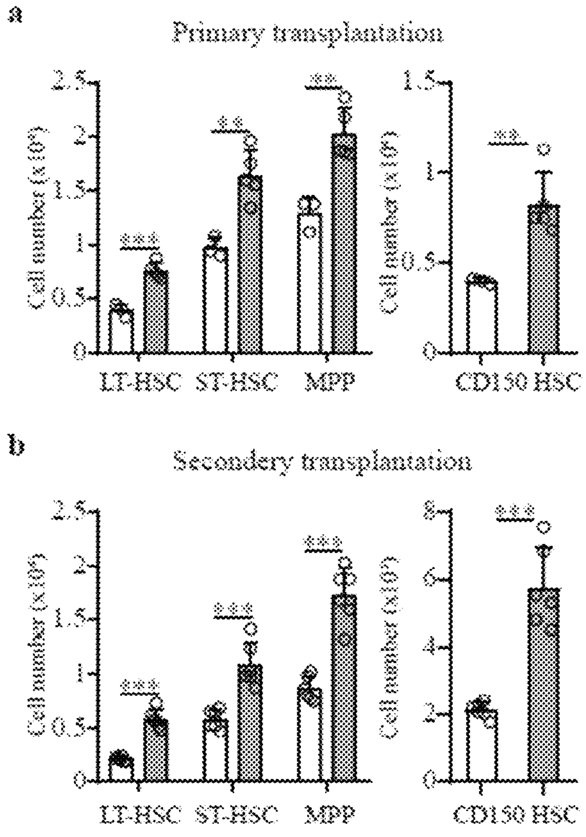
FIG. 22 illustrates that Sphk2 inhibition promotes HSC self-renewal and increases donor derived HSPC pool in transplantation model. The absolute numbers of donor derived HSPCs ($CD45.2^+$; LT-HSC, ST-HSC, MPP and CD150HSC) in the bone marrow were analyzed at 16 weeks after transplantation. (primary transplantation n=8 mice, secondary transplantation WT n=4 mice, Sphk2Δ/Δ n=6 mice per group). Data represent mean±s.d. Two-tailed Student's t-tests were used to assess statistical significance. *P<0.05, P<0.01, *P<0.001.

To analyze whether Sphk2 deficient HSPCs specifically have increased long-term self-renewal activity, 100 CD150 HSCs from Sphk2 deficient mice or control donor mice were transplanted into irradiated wide-type recipients along with $2\times10^5$ recipient bone marrow cells (FIG. 18). Consistently, Sphk2 deficient HSCs gave significantly higher levels of reconstitution ($CD45.2^+$ cells) than control cells through two rounds of 16-week observations (2.3-fold and 1.9-fold increase at 16 weeks in primary and secondary transplantation respectively) (FIG. 19). Sphk2 deficient HSCs more robustly reconstituted lymphoid than myeloid cells (FIG. 21) and generated more donor-derived HSPCs in recipients (FIG. 22).

Overall, these results strongly supported that attenuation of Sphk2 promotes HSPC number and function during homeostasis.

Example 4

Figure 23:
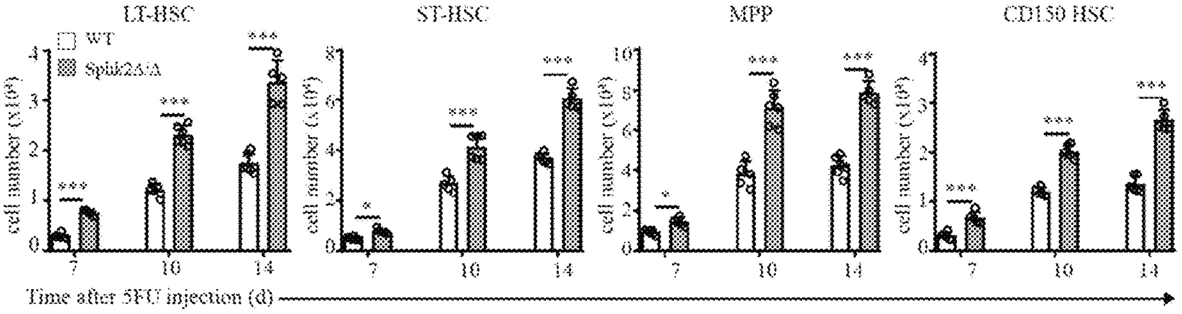
FIG. 23 illustrates HSPC (LT-HSC, ST-HSC, MPP, CD150HSC) numbers from Sphk2Δ/Δ or control mice at indicated time after 5 FU treatment. (d7 WT n=6 mice, Sphk2Δ/Δ n=5 mice; d10 WT n=5 mice, Sphk2Δ/Δ n=6 mice; d14 WT n=6 mice, Sphk2Δ/Δ n=5 mice).

To evaluate whether Sphk2 deficiency regulates the regenerative potential of HSPCs, response of mice to 5-fluorouracil (5 FU) was tested. The 5 FU ablates cycling cells and induces quiescent HSPCs to activate and repopulate the bone marrow. It was found that the increased HSPC pool was also maintained in Sphk2 deficient mice under 5 FU challenge (FIG. 23).

Figure 24:
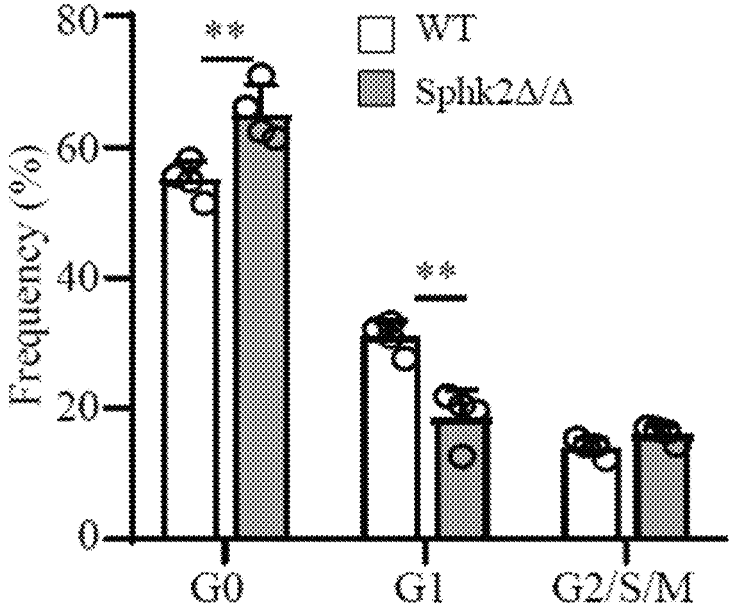
FIG. 24 illustrates cell cycle analysis of CD150HSCs from Sphk2Δ/Δ or control mice at day 7 after 5 FU treatment. (n=4 mice).
Figure 25:
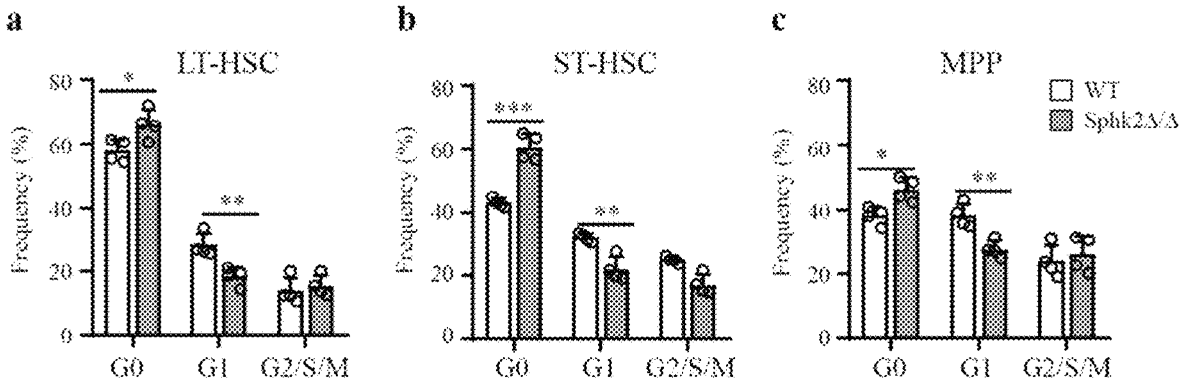
FIG. 25 illustrates that Sphk2 inhibition promotes HSC quiescence under chemotherapeutic stress. Cell cycle analysis of LT-HSC, ST-HSC and MPP in the bone marrow from Sphk2Δ/Δ or control mice (WT) at day 7 post 5 FU treatment (n=4 mice). Data represent mean±s.d. Two-tailed Student's t-tests were used to assess statistical significance. *P<0.05, P<0.01, *P<0.001.
Figure 26:
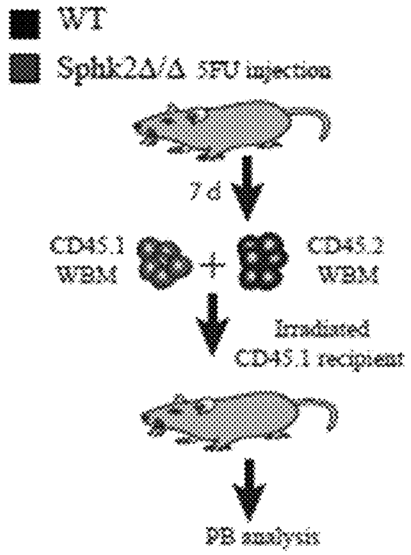
FIG. 26 illustrates a scheme for quantification of functional HSCs by transplantation assay. $2\times10^5$ bone marrow cells from Sphk2Δ/Δ or control mice at day 7 after 5 FU treatment were transplanted into irritated mice along with $2\times10^5$ recipient bone marrow cells.
Figure 27:
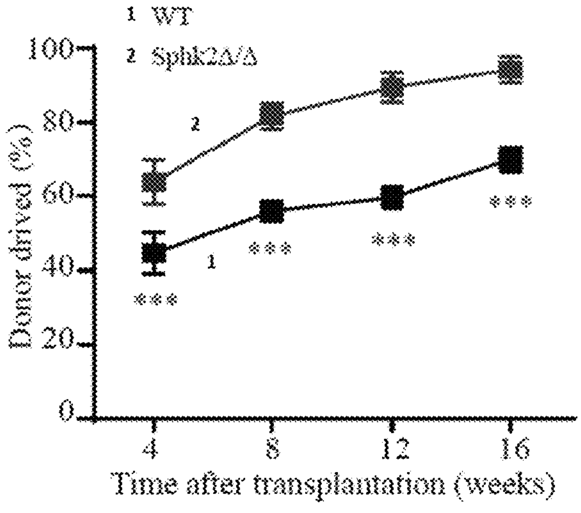
FIG. 27 illustrates PB analysis for total engrafted donor cells at the indicated number of weeks after transplantation (WT n=6 mice, Sphk1Δ/Δ n=7 mice group).
Figure 28:
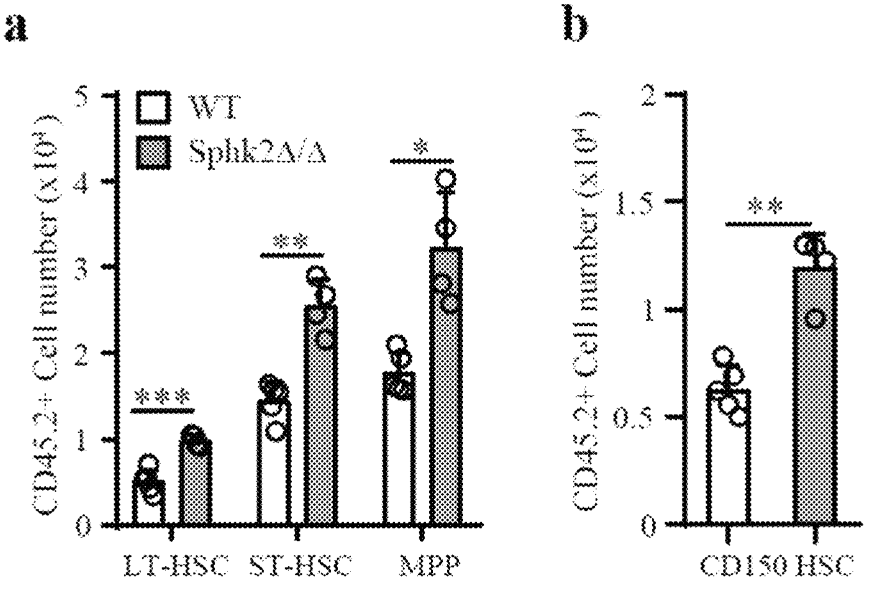
FIG. 28 illustrates that Sphk2 inhibition promotes HSC regeneration post chemotherapeutic stress. Quantification of functional HSC regeneration by transplantation assay. $2\times10^5$ bone marrow cells from Sphk2Δ/Δ or control mice at day 7 after 5 FU treatment were transplanted into irritated mice along with $2\times10^5$ recipient bone marrow cells. The absolute numbers of donor derived HSPCs ($CD45.2^+$; LT-HSC, ST-HSC, MPP and CD150HSC) in the bone marrow were analyzed at 16 weeks after transplantation. (WT n=5 mice, Sphk2Δ/Δ n=4 mice). Data represent mean±s.d. Two-tailed Student's t-tests were used to assess statistical significance. *P<0.05, P<0.01, *P<0.001.
Figure 29:
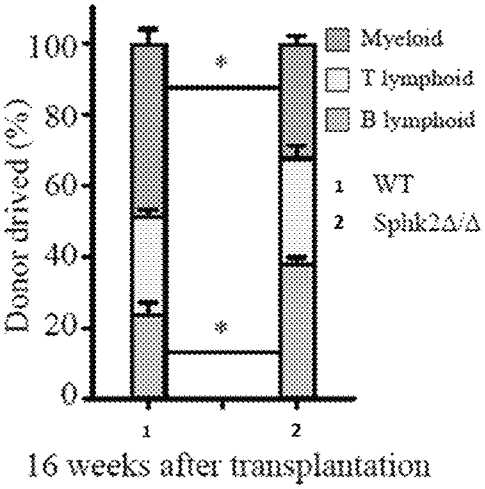
FIG. 29 illustrates the percentage of donor-derived B, T and myeloid lineage cells at 16 weeks after transplantation (e) (WT n=6 mice, Sphk1Δ/Δ n=7 mice group).

Cell cycle analysis revealed that Sphk2 deficient CD150 HSCs have increased G0-phase fraction (from 54.9% to 65.1%) and reduced G1-phase fraction (from 31.0% to 18.7%) (FIG. 24), which was also evidenced in LT-HSCs, ST-HSCs and MPPs (FIG. 25). To test whether Sphk2 deficient mice have improved HSC regenerative potential post-5 FU treatment, a competitive repopulation analysis was carried out and significantly higher reconstitution (CD45.2) and donor derived HSCs from Sphk2 deficient bone marrow cells than control donors was found (1.35-fold increase at 16 weeks; FIG. 26, FIG. 27; FIG. 28). It was also found that donor cells from Sphk2 deficient mice kept multilineage potential although more lymphocytes and less myeloid cells than control donors were present (FIG. 29).

Example 5

Figure 30:
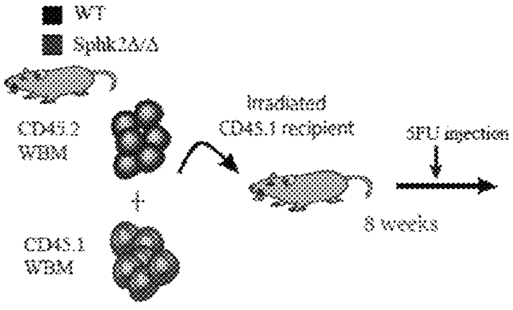
FIG. 30 illustrates a scheme for quantification of HSC function in response to chemotherapy by transplantation assay. $2\times10^5$ bone marrow cells from Sphk2Δ/Δ or control mice were transplanted into irritated mice along with $2\times10^5$ recipient bone marrow cells. Recipient mice were treated with 5 FU at 8 weeks after transplantation.
Figure 31:
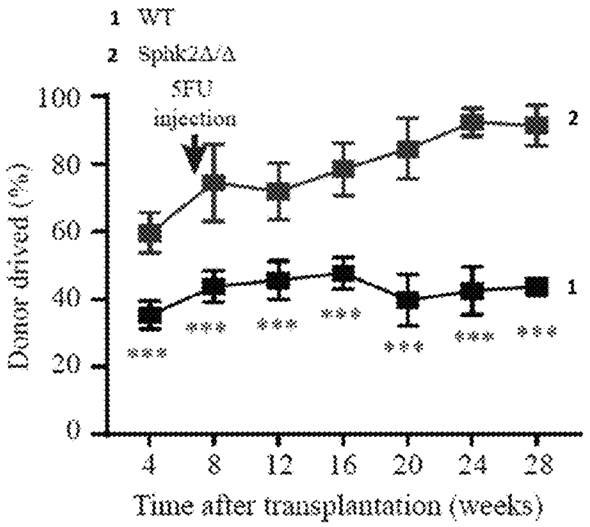
FIG. 31 illustrates PB analysis for total engrafted donor cells at the indicated number of weeks after transplantation (WT n=6 mice, Sphk2Δ/Δ n=10 mice group).
Figure 32:
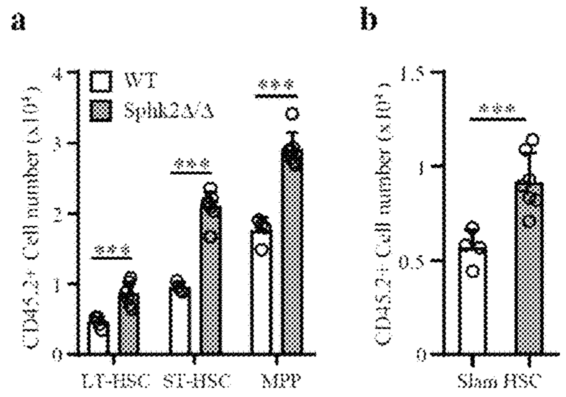
FIG. 32 illustrates that Sphk2 inhibition promotes HSC pool expansion in response to chemotherapeutic stress in recipients. Quantification of HSC function in response to chemotherapy by transplantation assay. $2\times10^5$ bone marrow cells from Sphk2Δ/Δ or control mice were transplanted into irritated mice along with $2\times10^5$ recipient bone marrow cells. Recipient mice were treated with 5 FU at 8 weeks after transplantation. The absolute numbers of donor derived HSPCs ($CD45.2^+$; LT-HSC, ST-HSC, MPP and CD150HSC) in the bone marrow were analyzed at 28 weeks after 5 FU treatment. (WT n=4 mice, Sphk2Δ/Δ n=7 mice). Data represent mean±s.d. Two-tailed Student's t-tests were used to assess statistical significance. *P<0.05, P<0.01, *P<0.001.
Figure 33:
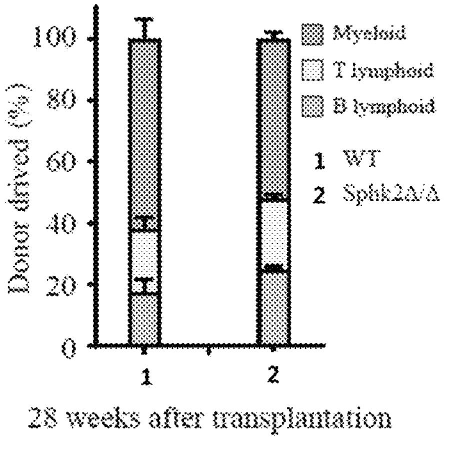
FIG. 33 illustrates the percentage of donor-derived B, T and myeloid lineage cells at 28 weeks after 5 FU treatment (h) (WT n=6 mice, Sphk2Δ/Δ n=10 mice group).

To assess whether Sphk2 deficient HSPCs have improved regenerative capacity, recipient mice were challenged with 5 FU at 8 weeks after transplantation with Sphk2 deficient bone marrow cells or control donor cells along with recipient bone marrow cells (FIG. 30). Consistently, Sphk2 deficient HSPCs gave higher reconstitution (2-fold increase at 28 weeks; FIG. 31), more donor derived HSCs (FIG. 32) and were capable of multilineage reconstitution (FIG. 33).

Figure 34:
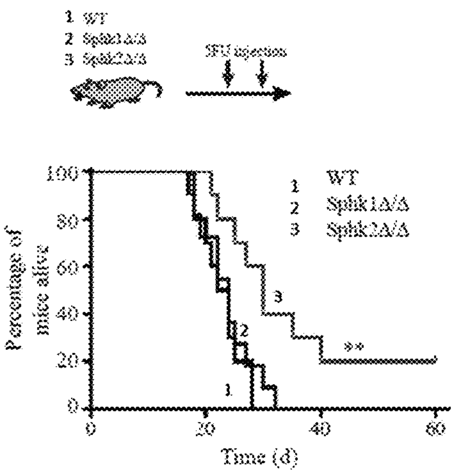
FIG. 34 illustrates survival of Sphk2Δ/Δ or control mice after serious 5 FU treatment every 7 day (WT and Sphk2 n=10 mice group, Sphk1 n=11 mice).

In addition, after multiple 5 FU challenges, Sphk2 deficient mice showed significantly greater survival than Sphk1 deficient mice or control mice (P=0.004; FIG. 34).

Figure 35:
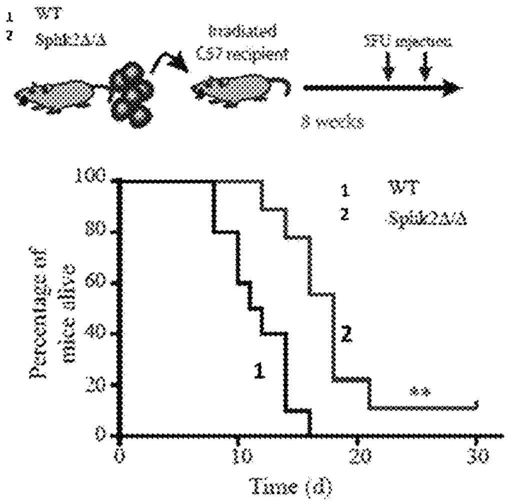
FIG. 35 illustrates survival of irradiated recipient mice received $1\times10^6$ bone marrow cells from Sphk2Δ/Δ or control mice and 5 FU treatment at 8 weeks after transplantation (WT n=6 mice, Sphk1Δ/Δ n=9 mice group).

To further test whether the increased survival is due to improved hematopoietic recovery, lethally irradiated widetype recipients were transplanted with Sphk2 deficient or control bone marrow cells and the recipients were further challenged with multiple 5 FU injections at 8 weeks after transplantation. Transplantation of Sphk2 deficient bone marrow cells significantly increased survival in wild-type recipients compared to control bone marrow cells (P=0.001; FIG. 35), further demonstrating improved hematopoietic recovery due to Sphk2 attenuation.

Together, these results demonstrated that attenuation of Sphk2 markedly promotes HSPC expansion and function during homeostasis and chemotherapy-induced injury.

Example 6

Figure 36:
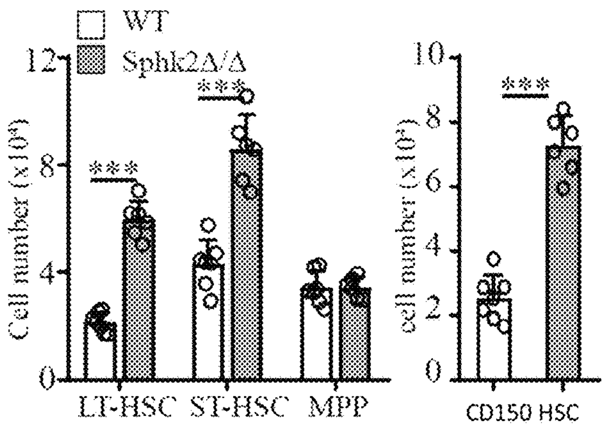
FIG. 36 illustrates HSPC (LT-HSC, ST-HSC, MPP, CD150HSC) numbers (WT n=7 mice, Sphk2Δ/Δ n=6 mice group) from Sphk2Δ/Δ or control mice at 26-month old.
Figure 37:
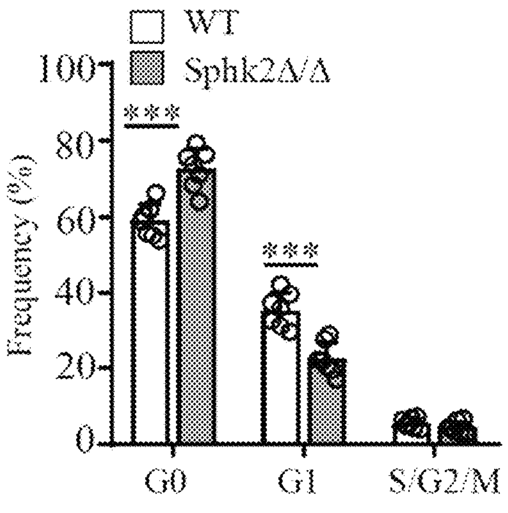
FIG. 37 illustrates cell cycle analysis of CD150HSCs (WT n=7 mice, Sphk2Δ/Δ n=7 mice group) from Sphk2Δ/Δ or control mice at 26-month old.

To examine the effect of Sphk2 attenuation during aging, 26-month old mice were analyzed. HSPC numbers were markedly increased in aged Sphk2 deficiency mice compared to littermate controls (FIG. 36). The quiescence of aged CD150 HSCs was preserved in Sphk2 deficient mice compared to littermates (G0-phase fraction, from 58.8% to 72.6%) (FIG. 37).

Figure 38:
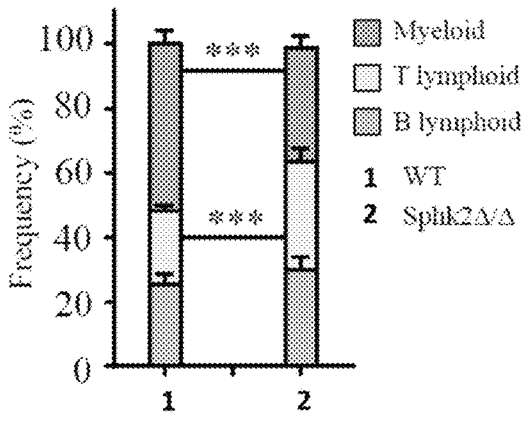
FIG. 38 illustrates PB analysis for the percentage of B, T and myeloid lineage cells from Sphk2Δ/Δ or control mice at 20-month old. (WT n=7 mice, Sphk2Δ/Δ n=7 mice group).

It was found that the frequency of lymphocytes in aged Sphk2 deficient mice was notably increased compared to their littermates, paralleled by a decreased myeloid cell frequency (FIG. 38), indicating an anti-aging effect of Sphk2 attenuation in hemopoietic system.

Figure 39:
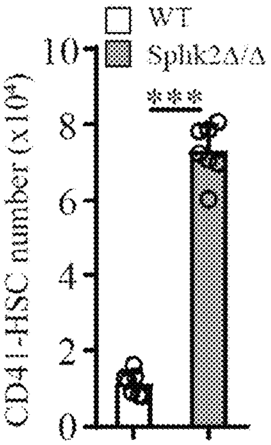
FIG. 39 illustrates the absolute number of $CD41^-$HSC ($CD41^-CD48^-CD150^+$LSK) from Sphk2Δ/Δ or control mice at 26-month old. (WT n=7 mice, Sphk2Δ/Δ n=7 mice group).
Figure 40:
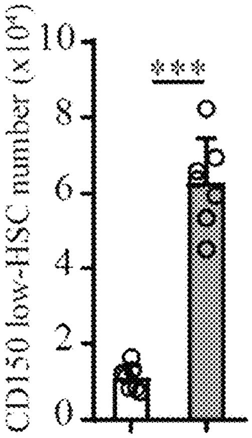
FIG. 40 illustrates $CD150^{low}$ HSC ($CD48^-CD150^{low}$LSK) from Sphk2Δ/Δ or control mice at 26-month old. (WT n=7 mice, Sphk2Δ/Δ n=7 mice group).

Indeed, expression of CD41 and CD150 on HSPCs increase with age, but a 6.4-fold increase of $CD41^-$HSCs (FIG. 39) and a 5.7-fold increase of $CD150^{low}$HSCs (FIG. 40) in Sphk2 deficient mice were found compared to littermates.

Figure 41:
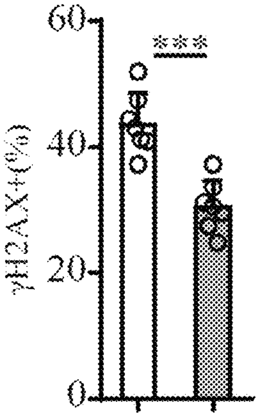
FIG. 41 illustrates the frequency of $\lambda H2AX^+$ cells (f; n=7) in CD150 HSCs from Sphk2Δ/Δ or control mice at 26-month old.
Figure 42:
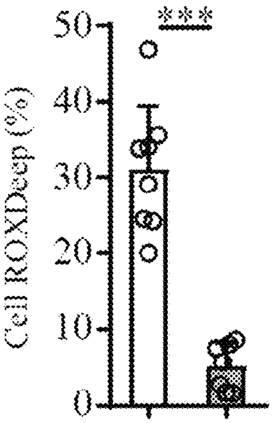
FIG. 42 illustrates the frequency of Cell ROXDeep ($ROS^{high}$) cells in CD150 HSCs from Sphk2Δ/Δ or control mice at 26-month old. (g; WT n=8 mice, Sphk2Δ/Δ n=7 mice group).

The DNA damage rate in aged CD150 HSCs from Sphk2 deficient mice was also reduced (FIG. 41). Notably, ROS levels in aged CD150 HSCs from Sphk2 deficient mice was markedly reduced compared to their littermates (82% reduction, FIG. 42).

These results indicate a functional recovery of aged HSCs in Sphk2 deficient mice.

Example 7

Figure 43:
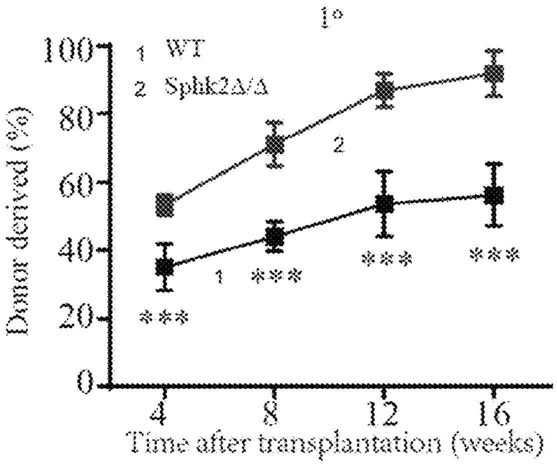
FIGS. 43-46 illustrate quantification of functional HSCs by transplantation assay. $2\times10^5$ bone marrow cells from Sphk2Δ/Δ or control mice at 26-month old were transplanted into irritated mice along with $2\times10^5$ recipient bone marrow cells. $1\times10^6$ bone marrow cells from primary recipient mice were transplanted into irritated mice in secondary transplantation. PB analysis for total engrafted donor cells at the indicated number of weeks after transplantation (FIG. 43, FIG. 44) and the percentage of donor-derived B, T and myeloid lineage cells at 16 weeks after transplantation (FIG. 45, FIG. 46) (primary transplantation n=8 mice, secondary transplantation WT n=4 mice, Sphk2Δ/Δ n=6 mice per group).
Figure 44:
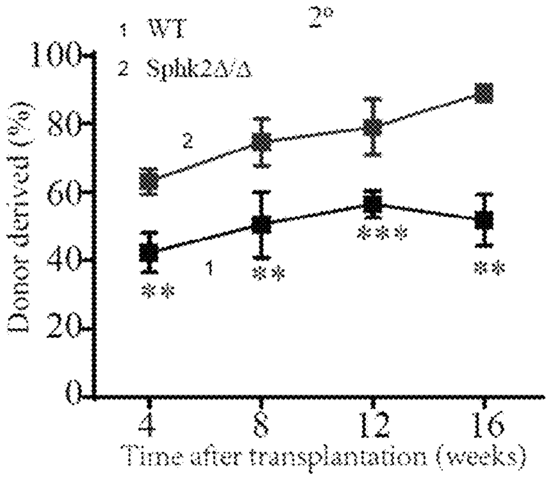
Figure 45:
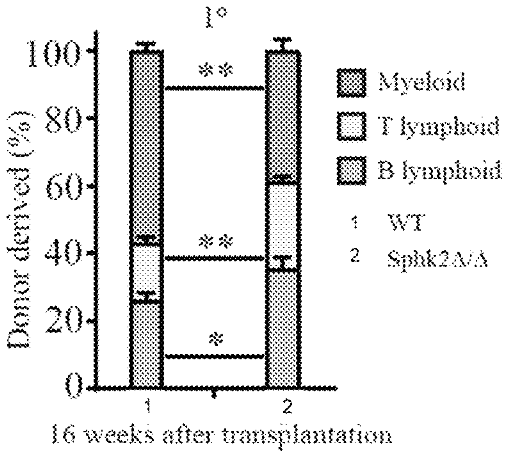
Figure 46:
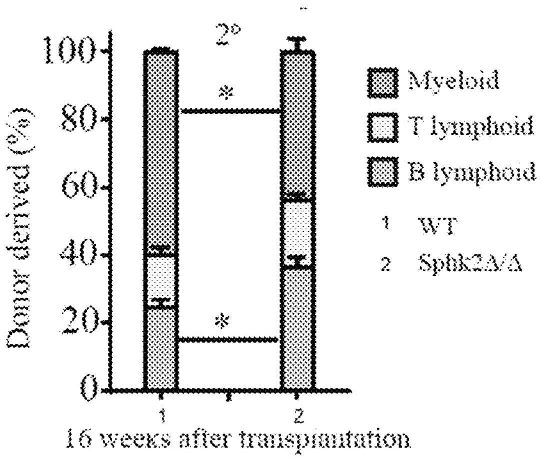

Next, a competitive repopulation analysis was performed to investigate the impact of Sphk2 deficiency on aged HSPC function. A significantly higher reconstitution was observed throughout the two rounds of 16-week observation of mice transplanted with total bone marrow cells from aged Sphk2 deficient mice than aged control littermates (1.6-fold and 1.7-fold increase at 16 weeks in primary and secondary transplantation respectively) (FIG. 43, FIG. 44). Mice transplanted with Sphk2 deficient cells showed an improved lymphopoiesis (both B and T cells in primary transplantation, and B cells in secondary transplantation), and a reduction in myeloid skewing (FIG. 45, FIG. 46).

These results demonstrated that aged HSPCs from Sphk2 deficient mice have improved stem cell function.

Example 8

Figure 47:
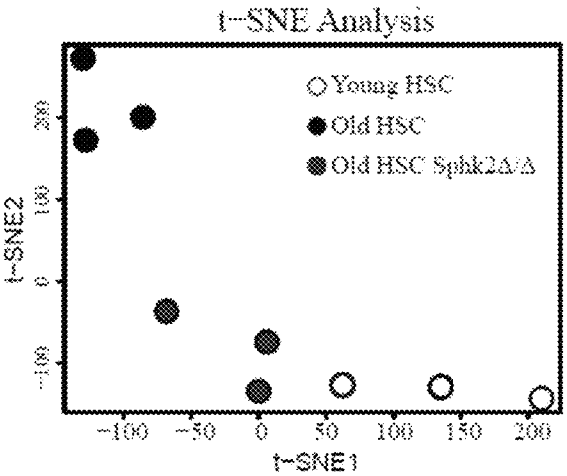
FIG. 47 illustrates t-SNE plot depicting distribution of young HSCs from WT mice (2-month old), HSCs from wide type control 26-month old mice (aged HSC) or Sphk2Δ/Δ 26-month old mice (aged HSC Sphk2 Δ/Δ) and following RNA-seq analysis.
Figure 48:
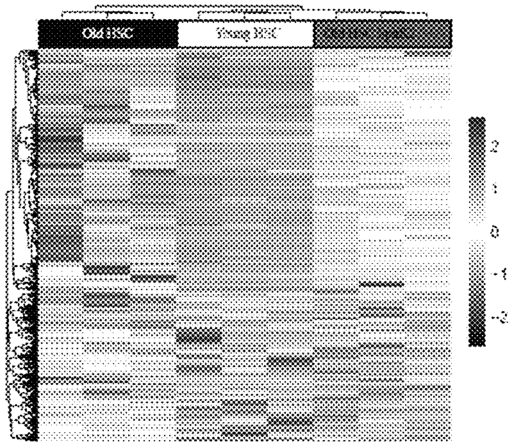
FIG. 48 illustrates unsupervised hierarchical clustering of top variable genes, comparing young HSCs, aged HSCs and aged HSC Sphk2 Δ/Δ. (n=3 samples from 6 mice per group).
Figure 49:
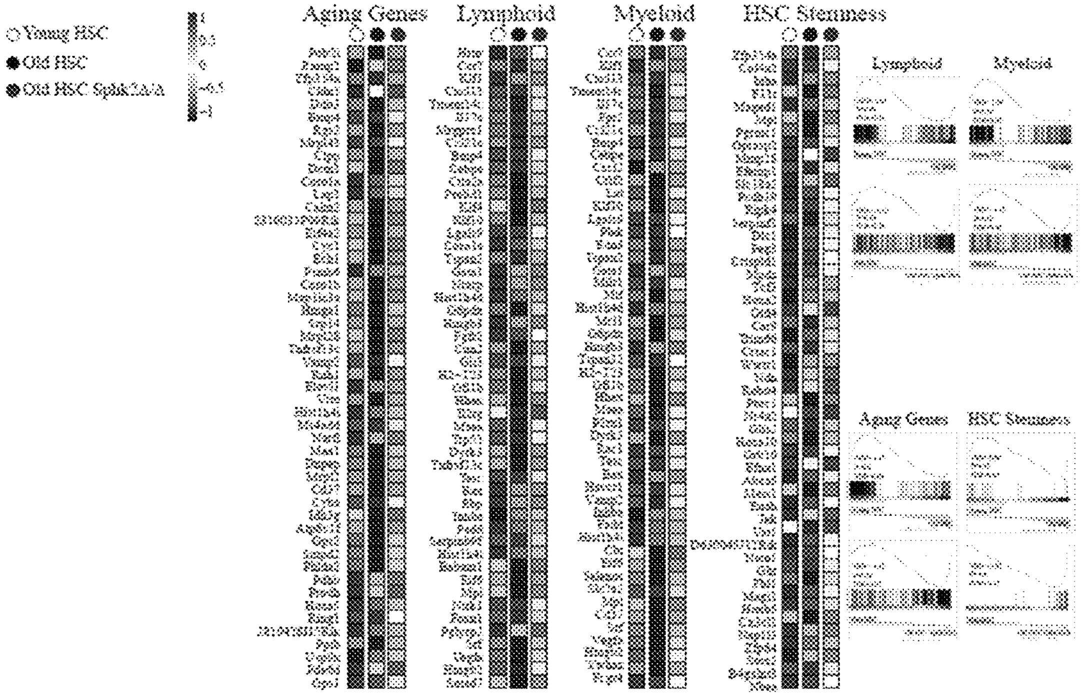
FIG. 49 illustrates heat map of mean gene expression levels and signature enrichment plots from GSEA using aging, lymphoid, myeloid and Mk/platelet gene sets in aged HSCs from WT control mice or Sphk2 Δ/Δ mice (26-month old), and young HSCs from WT mice (2-month old) as control. (n=3 samples from 6 mice per group). 1° primary transplantation, 2° secondary transplantation.
Figure 50:
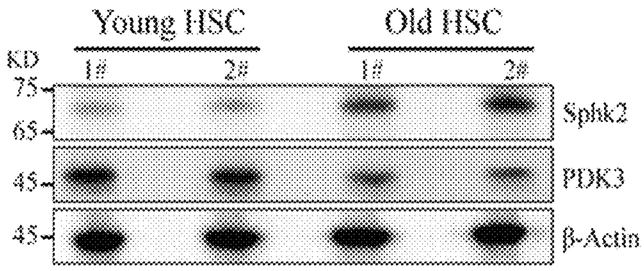
FIG. 50 illustrates that Sphk2 expression increases in old HSCs. Western blot analyses of Sphk2 and PDK3 expression in 10,000 young or old HSCs. β-Actin was used as a loading control. 1 # and 2 # indicated two individual mice.
Figure 88:
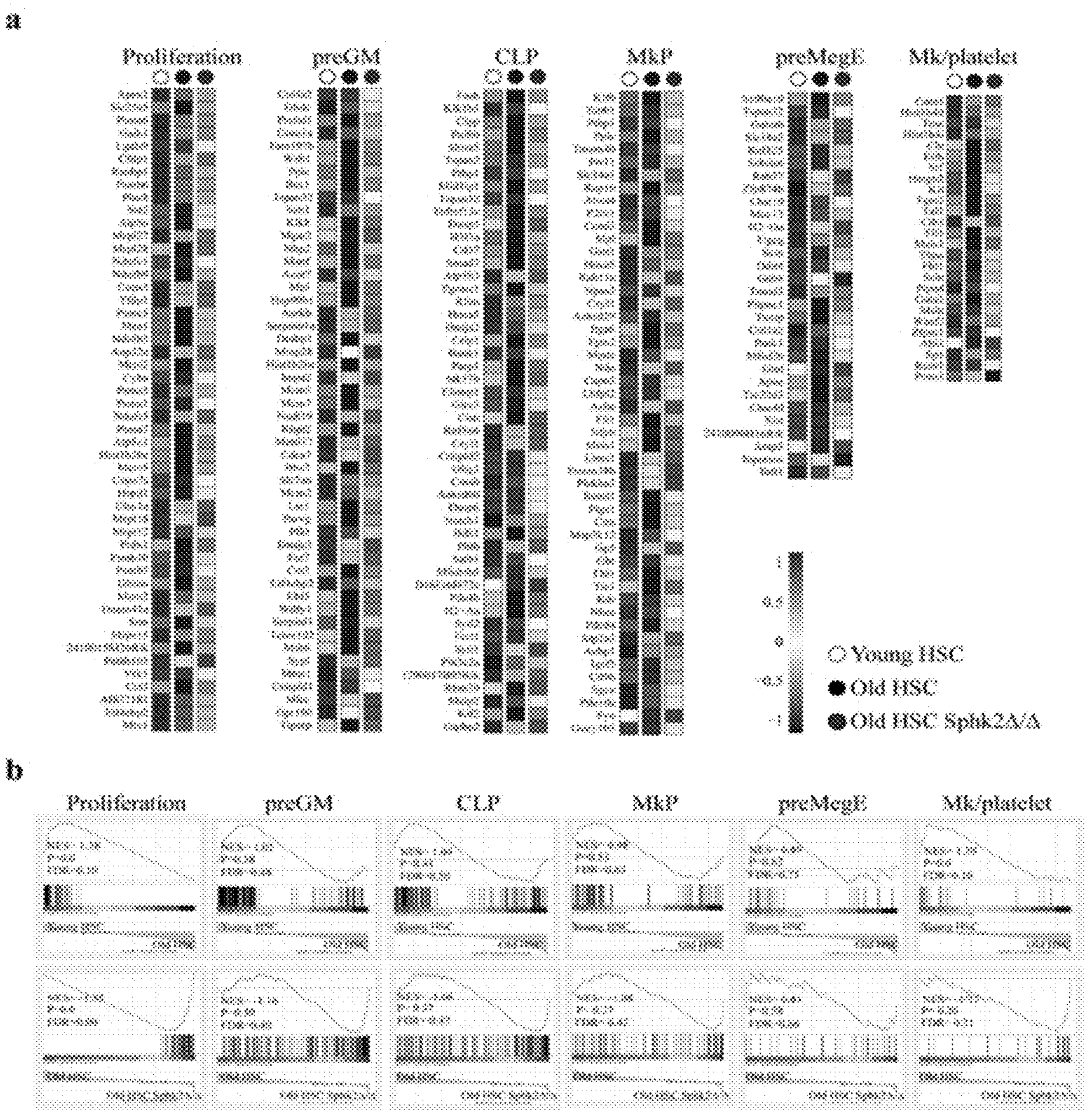
FIG. 88 shows Sphk2 inhibition rejuvenates old HSCs the array of genes involved in lineage differentiation. Heat map of mean gene expression levels and signature enrichment plots from GSEA using indicated gene were set in old HSCs from WT control mice or Sphk2 Δ/Δ mice (26 month old), and young HSCs from WT mice (2 month old) as control. (n=3 samples from 6 mice per group).

To further confirm that loss of Sphk2 rejuvenated aged HSPCs, the transcriptomes of HSPCs sorted from either young (yHSCs), aged HSCs (aHSCs) from control mice or aHSCs from aged Sphk2 deficient mice were analyzed. Using t-SNE analysis, it was found that aHSCs from Sphk2 deficient mice clustered separately from control aHSCs and instead clustered closer to yHSCs (FIG. 47). Unsupervised hierarchical clustering of top differentially expressed genes also revealed that the aHSC from aged Sphk2 deficient mice express signature genes became similar to that of yHSCs (FIG. 48). Furthermore, a remarkable restoration of HSPC aging genes, lymphoid-lineage genes, myeloid-lineage genes and megakaryocyte/platelet genes from Gene Ontology Resource was revealed in aHSCs from Sphk2 deficient mice toward levels in yHSCs. Notably, HSC Stemness genes, which were reduced in control aHSCs, was instead more similar to yHSCs in aHSCs from Sphk2-deficient mice (FIG. 49). This preservation of a young phenotype was also evidenced in other HSPC and progenitor signature genes (FIG. 88). And the results of the Western blot were shown that Sphk2 expression was increased in old HSCs (FIG. 50).

There results demonstrate that Sphk2 attenuation preserved or rejuvenated functional aHSCs both in functionality and molecular signature.

Example 9

Figure 51:
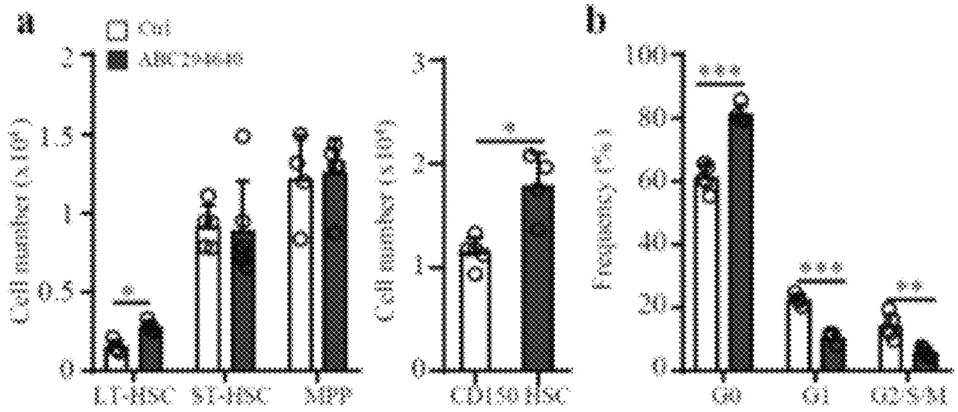
FIG. 51 illustrates that ABC294460 expands HSC pool and promotes HSC quiescence during hemostasis. (a) The absolute number of HSPCs (LT-HSC, ST-HSC, MPP and CD150HSC) in the bone marrow (a) and cell cycle analysis of CD150 HSCs (b) in bone marrow from from C57BL/6J mice after ABC294640 or vehicle control treatment (n=5 mice). Data represent mean±s.d. Two-tailed Student's t-tests were used to assess statistical significance. *P<0.05, P<0.01, *P<0.001.
Figure 52:
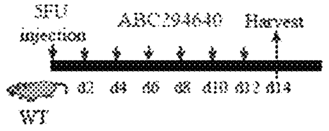
FIG. 52 shows a scheme for ABC294640 treatment to improve HSC regeneration after chemotherapeutic stress.
Figure 53:
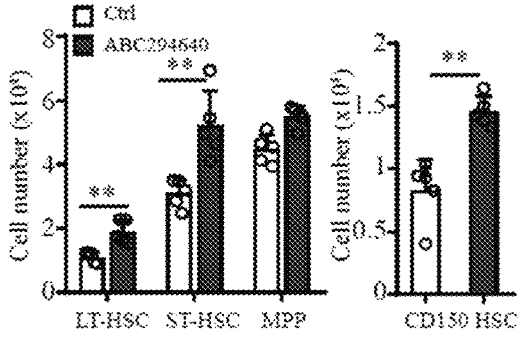
FIG. 53 shows HSPC (LT-HSC, ST-HSC, MPP, CD150HSC) numbers from C57BL/6J mice after 5 FU and ABC294640 or vehicle control treatment (n=5 mice).

ABC294640 was used as an example of Sphk2 inhibitors. Mice receiving ABC294640 treatment exhibited an expanded HSPC pool (2.1-fold increase for LT-HSCs and 1.7-fold increase for CD150 HSCs) and increased quiescence (FIG. 51) compared with control mice treated with vehicle alone. Next, the effect of ABC294640 on HSPC regenerative potential was evaluated by subjecting mice to 5 FU treatment and followed by ABC294640 or vehicle alone injections (FIG. 52). Mice treated with ABC294640 significantly increased HSPC pool size (2.2-fold, 1.6-fold, and 2.2-fold increase for LT-HSC, ST-HSC and CD150 HSC respectively; FIG. 53) compared to mice treated with vehicle at day 14 post 5 FU.

Figure 54:
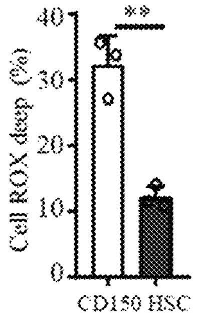
FIG. 54 shows the frequency of Cell ROXDeep ($ROS^{high}$) cells CD150HSCs from C57BL/6J mice after 5 FU and ABC294640 or vehicle control treatment (n=3 mice).

ABC294640 treatment also markedly reduced ROS level in CD150 HSCs from mice at day 14 after 5 FU treatment (FIG. 54), indicating that HSC function was preserved.

Figure 55:
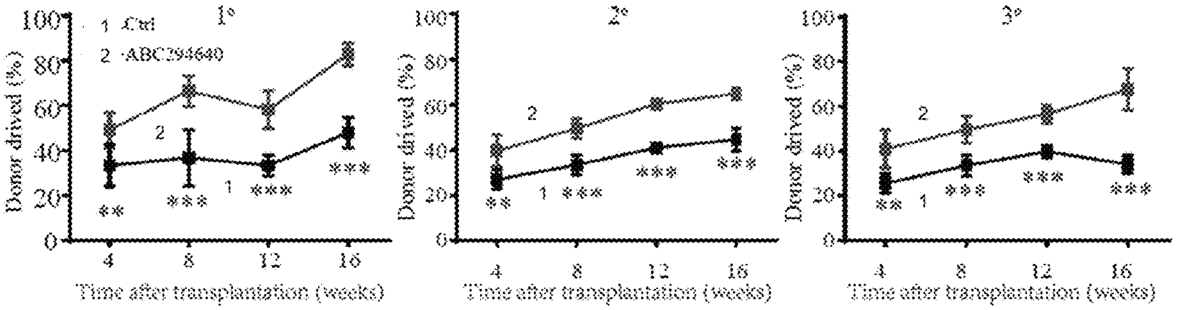
FIG. 55 shows quantification of functional HSCs by transplantation assay. $2\times10^5$ bone marrow cells from C57BL/6J mice after 5 FU and ABC294640 or vehicle control treatment were transplanted into irritated mice along with $2\times10^5$ recipient bone marrow cells. $1\times10^6$ bone marrow cells from primary or secondary recipient mice were transplanted into irritated mice in secondary or tertiary recipients respectively.
Figure 56:
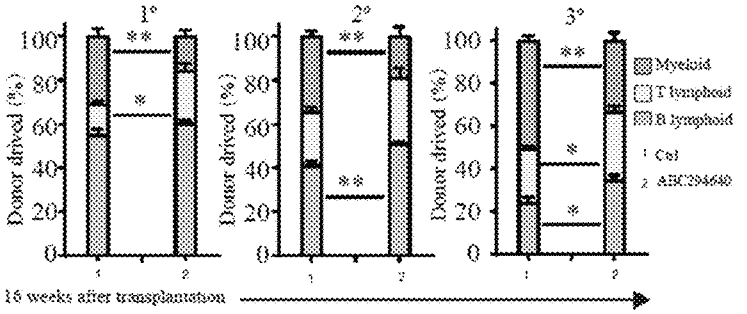
FIG. 56 shows PB analysis for total engrafted donor cells at the indicated number of weeks after transplantation and the percentage of donor-derived B, T and myeloid lineage cells at 16 weeks after transplantation (primary transplantation vehicle control n=7 mice ABC294640 n=8 mice, secondary transplantation n=5 mice, tertiary transplantation n=8 mice per group).
Figure 57:
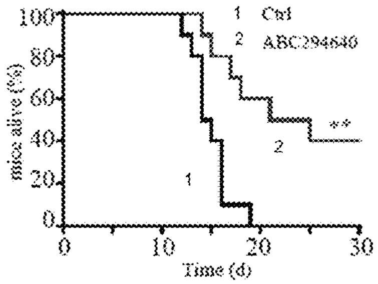
FIG. 57 shows survival of C57BL/6J mice after serious 5 FU treatment every 7 days and ABC294640 treatment every other day (n=10 mice group).

Next, competitive repopulation analyses were carried out to investigate whether ABC294640 treatment functionally promotes HSPC regeneration after chemotherapeutic stress. Mice receiving bone marrow cells after ABC294640 treatment gave significantly higher reconstitution through three rounds of 16-week observation period compared to mice receiving control vehicle treated bone marrow cells (1.7-fold, 1.5-fold and 1.9-fold increase at 16 weeks in primary, secondary and tertiary transplantation respectively; FIG. 55). Consistently, it was observed that pharmaceutical inhibition of Sphk2 also markedly promoted lymphopoiesis and suppressed myeloid skewing in recipients (FIG. 56). In agreement with the improved HSC regenerative potential, ABC294640 treated mice had notably increased survival after serial 5 FU challenges compared to control (FIG. 57).

Example 10

Figure 58:
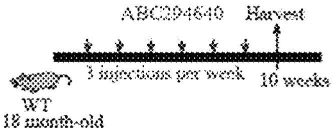
FIG. 58 shows a scheme for ABC294640 treatment to attenuate HSC aging.
Figure 59:
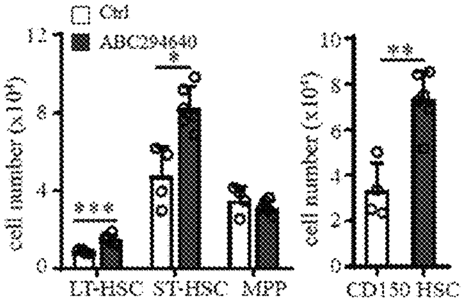
FIG. 59 shows HSPC (LT-HSC, ST-HSC, MPP, CD150HSC) numbers.
Figure 60:
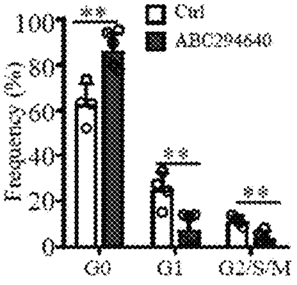
FIG. 60 shows cell cycle of analysis of CD150 HSCs.
Figure 61:
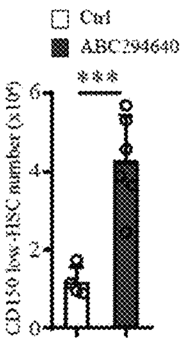
FIG. 61 shows cell number of $CD150^{low}$ HSC.
Figure 62:
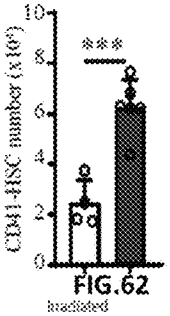
FIG. 62 shows $CD41^-$HSC number.

Next, the ability of ABC294640 to reverse HSPC aging was examined. 18-month old mice were subjected to ABC294640 or vehicle control treatment for 10 weeks (FIG. 58) and it was observed that ABC294640 treatment significantly expanded the HSPC pool (FIG. 59) and preserved CD150 HSC quiescence (FIG. 60). Notably, ABC294640 treatment markedly increased $CD150^{low}$HSC population (3.6-fold increase; FIG. 61) and $CD41^{-}$ HSC population (2.2-fold increase; FIG. 62), indicating that ABC294640 treatment functionally reversed HSPC aging.

Figure 63:
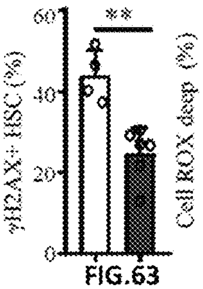
FIG. 63 shows the frequency of $\lambda H2AX^+$ cells in CD150 HSCs.
Figure 64:
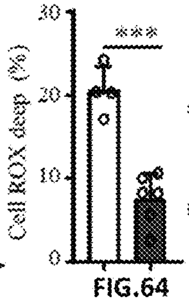
FIG. 64 shows the frequency of Cell ROXDeep ($ROS^{high}$) cells in CD150 HSCs.
Figure 65:
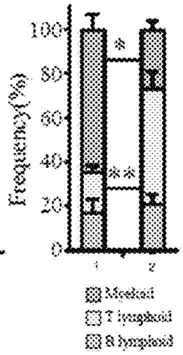
FIG. 65 shows PB analysis for the percentage of B, T and myeloid lineage cells.
Figure 66:
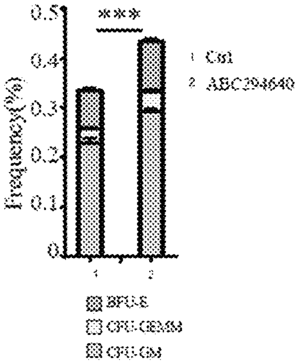
FIG. 66 shows the frequencies of myeloerythroid-colony-forming progenitors in bone marrow. Bone marrow and PB cells were from 19-month old C57BL/6J mice followed by ABC294640 or vehicle control treatment for 3 treatments per week for 3 months (vehicle n=4 mice, ABC294640 n=6 mice). BFU-E, erythroid burst forming unit; GEMM, granulocyte erythrocyte monocyte megakaryocyte; GM, granulocyte macrophage.

In agreement, ABC294640 treatment significantly reduced DNA damage (43.7% reduction; FIG. 63) and ROS level (63% reduction; FIG. 64) in CD150 HSPCs compared to vehicle. Further, ABC294640 treated mice had markedly increased lymphopoiesis and suppressed myeloid skewing in peripheral blood (FIG. 65), indicating that ABC294640 treatment could rejuvenate aged HSPCs. Indeed, colony-forming progenitor frequency was significantly higher in bone marrow cells from ABC294640 treated mice than vehicle treated controls (FIG. 66).

Example 11

Next, the ability of ABC294640 to improve hematopoietic reconstitution was examined.

Figure 67:
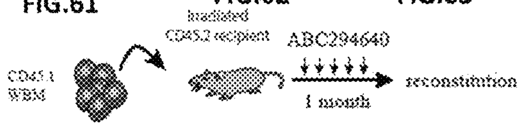
FIG. 67 shows scheme for ABC294640 treatment to improve hematopoietic reconstitution after bone marrow transplantation.
Figure 68:
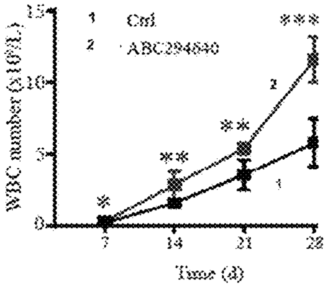
FIG. 68 shows the absolute number of white blood cells (WBC) in PB at indicated time after transplantation.
Figure 69:
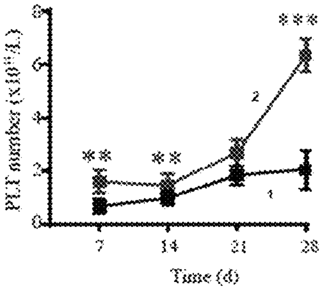
FIG. 69 shows the absolute number of platelets (PLT) in PB at indicated time after transplantation.
Figure 70:
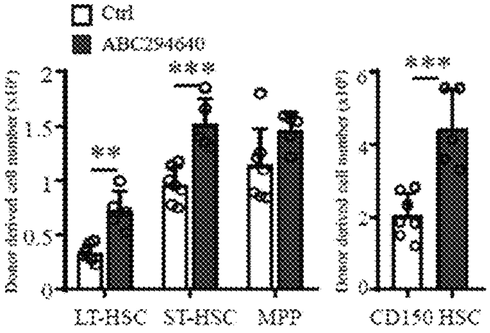
FIG. 70 shows the number of donor derived HSPC (LT-HSC, ST-HSC, MPP, CD150HSC) numbers in recipients at one month after transplantation.

$1\times10^6$ bone marrow cells were transplanted into lethally irradiated recipients, and the recipients were subjected to ABC294640 treatment or vehicle control (FIG. 67). Notably, improved reconstitution of white blood cells (1.9-fold increase at 28 days after transplantation; FIG. 68) and platelets (2.6-fold increase at 28 days after transplantation; FIG. 69) in recipients during the first month observation period were observed, due to improved recovery of donor derived HSC pool (2.2-fold, 1.6-fold and 2.2-fold increase for LT-HSC, ST-HSC and CD150 HSC, respectively; FIG. 70).

These results indicate that Sphk2 inhibitors (e.g. ABC294640) could improve HSPC functions.

Example 12

Figure 71:
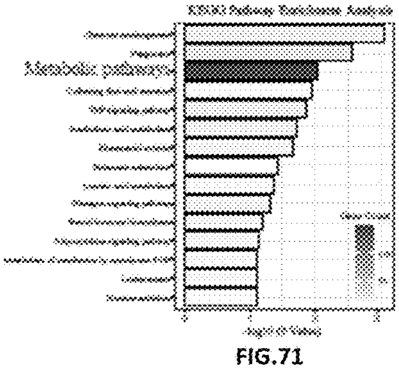
FIG. 71 shows enriched pathways of differentiation expressed genes in CD150 HSCs from Sphk2Δ/Δ or control littermates (n=3 samples from 6 mice per group). The enriched p value is derived from Fisher's exact test.
Figure 72:
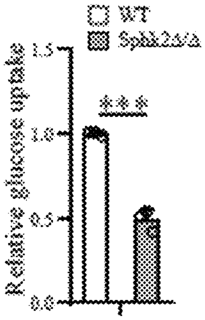
FIGS. 72-79 show relative glucose uptake (FIG. 72), relative intracellular pyruvate concentration (FIG. 73), lactate production (FIG. 74), LDH activity (FIG. 75), oxygen consumption rate (FIG. 76), intracellular ATP concentration (FIG. 77), intracellular NAD/NADH ratio (FIG. 78) and Cell ROXDeep ($ROS^{high}$) cells (FIG. 79) in HSCs from Sphk2Δ/Δ or control mice (Replicates are cells from WT n=7 mice, Sphk2Δ/Δ n=6 mice per experiment).
Figure 73:
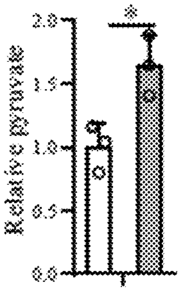
Figure 74:
Figure 75:
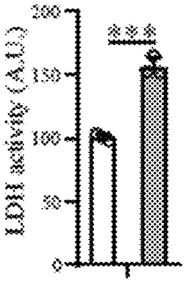
Figure 76:
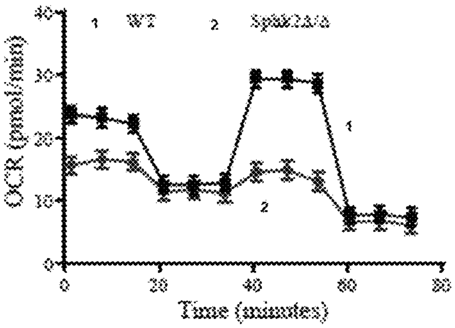
Figure 77:
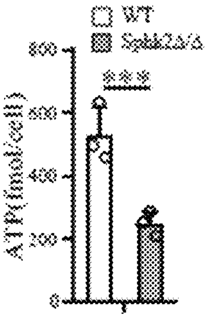
Figure 78:
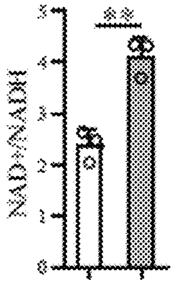

After analyzing the RNAseq data, it was found that carbon metabolic pathways are among the most significantly changed pathways in Sphk2 deficient HSPCs (FIG. 71). Sphk2 deficient HSCs had reduced glucose uptake (FIG. 72), but with increased pyruvate and lactate (FIG. 73 and FIG. 74) accompanied by increased intracellular glycolytic LDH activity (FIG. 75). Accordingly, Sphk2 deficient HSPCs had increased glycolysis than control HSCs. Further, it was found that Sphk2 deficient HSPCs had lower oxygen consumption rate (OCR), which was maintained by low mitochondrial oxygen consumption (FIG. 76). This resulted in less ATP production (FIG. 77) and higher $NAD^+$/NADH ratio (FIG. 78).

Figure 79:
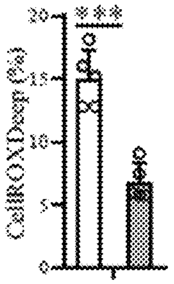

These results indicate that mitochondrial oxidative phosphorylation (OXPHOS) was suppressed in Sphk2 deficient HSCs. The increased LDH activity accelerated consumption of NADH, which would ameliorate oxidative stress. Indeed, it was found that the ROS level was dramatically reduced in Sphk2 deficient HSCs (54.5% reduction, FIG. 79).

Figure 81:
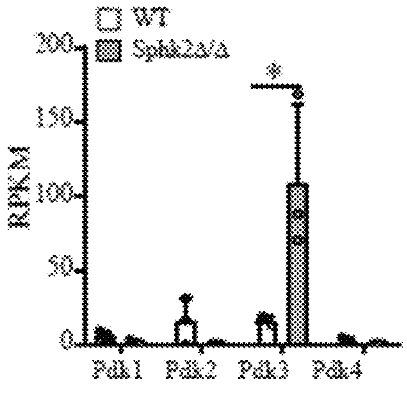
FIG. 81 shows RPKM (reads per kilobase million) of Pdk genes expression in HSCs from Sphk2Δ/Δ mice or control littermates (n=3 samples from 6 mice per group).

The RNAseq data further revealed that pyruvate dehydrogenase kinase (Pdk) 3 was dramatically upregulated in Sphk2 deficient HSCs. Within the 4 members of Pdk family, Pdk3 was selectively upregulated in Sphk2 deficient HSCs (FIG. 81).

Figure 82:
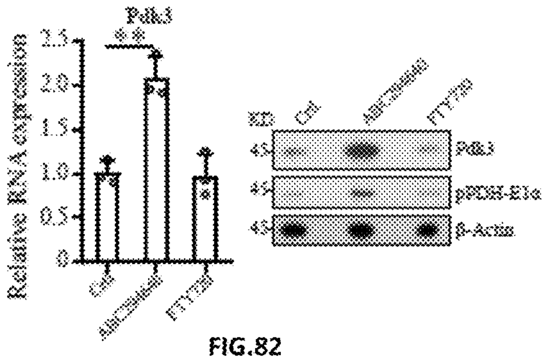
FIG. 82 shows Pdk3 mRNA levels in HSCs in the left panel, and immunoblotting for PDK3 and pPDH-E1α in HSCs in the right panel. β-actin was used as a loading control. HSCs from Sphk2Δ/Δ mice or WT littermates are treated with inhibitors as indicated.

Further, the Sphk2 inhibitor ABC294640 but not the S1P receptor inhibitor FTY720, could upregulate Pdk3 expression in HSPCs (FIG. 82), indicating that Sphk2 regulates Pdk3 expression independently of S1P's cell surface receptors.

Figure 83:
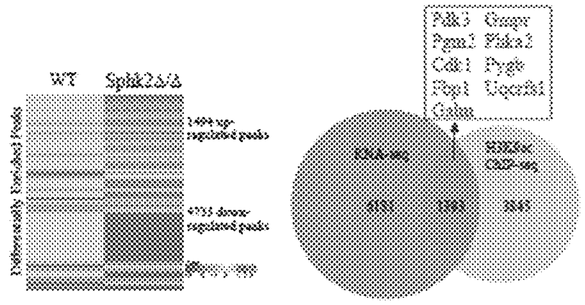
FIG. 83 is a heatmap showing average H3K9ac ChIP signals at differentially enriched peaks (DEPs).
Figure 84:
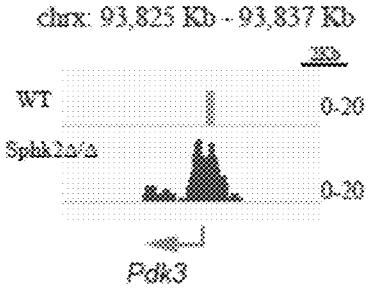
FIG. 84 shows that H3K9ac ChIP-seq tracks around Pdk3 promoter.

Further, H3K9 acetylation level was dramatically regulated in Sphk2 deficient HSCs, Notably, the H3K9 acetylation was markedly enriched in the promoter region of Pdk3 in Sphk2 deficient HSPCs, which is consistent with Pdk3 upregulation (FIG. 83 and FIG. 84).

Figure 85:
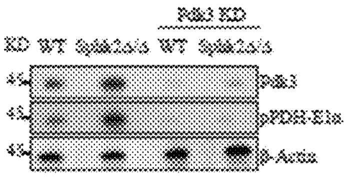
FIG. 85 shows immunoblotting for PDK3 and pPDH-E1α in HSCs.
Figure 86:
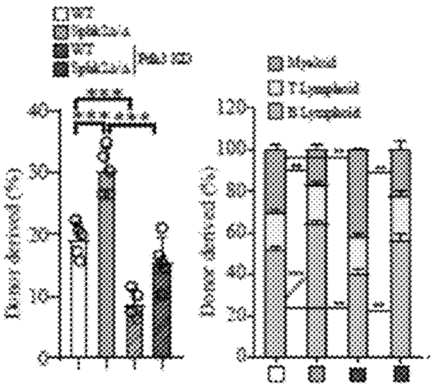
FIG. 86 shows the frequencies of myeloerythroid-colony-forming progenitors in HSCs. HSCs have received Pdk3 siRNA or control scramble siRNA. HSCs are from Sphk2Δ/Δ mice or control littermates as indicated (n=3 replicates from 4 mice).

Then, siRNA was used to knock-down Pdk3 in control and Sphk2 deficient HSCs. This resulted in reduced PDH-E1α phosphorylation (FIG. 85) and compromised HSPC activity in Sphk2 deficient HSCs (FIG. 86).

Figure 20:
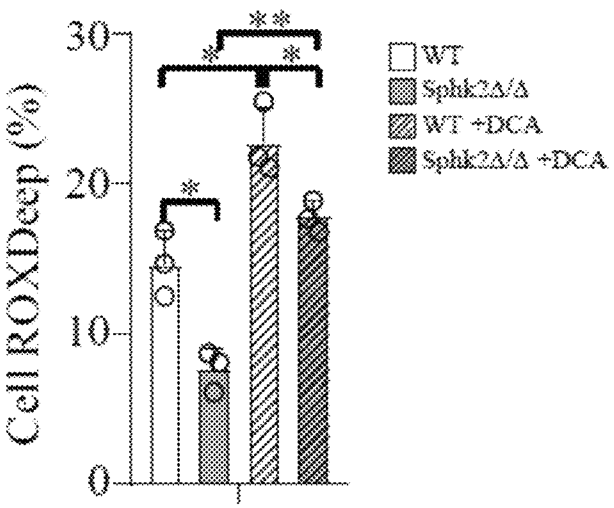
FIG. 20 illustrates the frequency of Cell ROXDeep ($ROS^{high}$) cells in CD150 HSCs.
Figure 80:
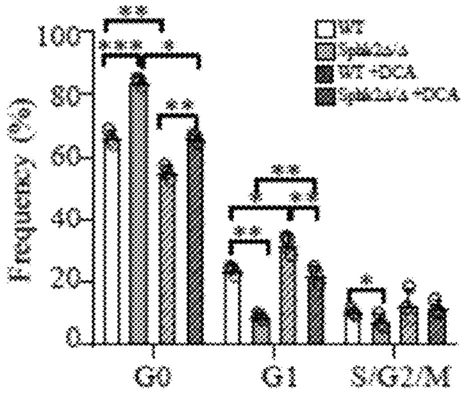
FIG. 80 shows cell cycle of analysis of CD150 HSCs.
Figure 87:
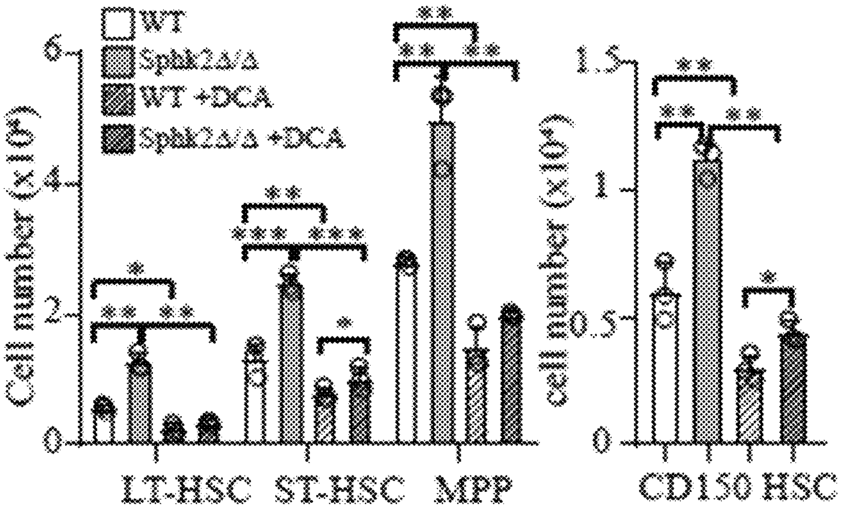
FIG. 87 shows HSPC (LT-HSC, ST-HSC, MPP, CD150HSC) numbers.

Then, the Pdk3 inhibitor dichloroacetate (DCA) was used to treat Sphk2 deficient and control mice for 14 days. DAC treatment resulted in reduced HSPC numbers (FIG. 87), compromised HSC quiescence (FIG. 80) and increased ROS levels (FIG. 20) in HSPCs from treated Sphk2 deficient mice than from vehicle treated littermates.

Figure 12:
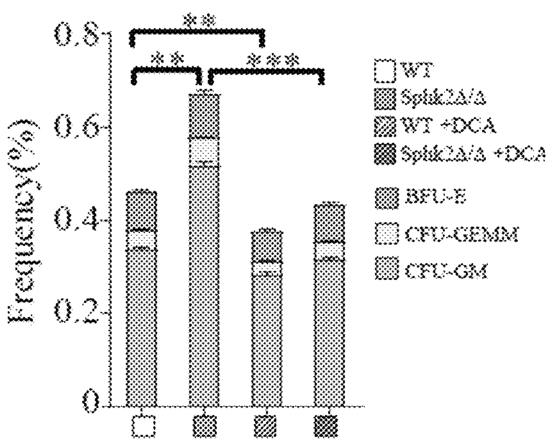
FIG. 12 illustrates the frequencies of myeloerythroid-colony-forming progenitors in bone marrow. Sphk2Δ/Δ mice or control littermates are treated with DAC for 3 weeks as indicated (n=3 mice).

Consequently, Pdk3 inhibition completely compromised the stem cell function increase in HSPCs from Sphk2 deficient mice (FIG. 12).

Figure 13:
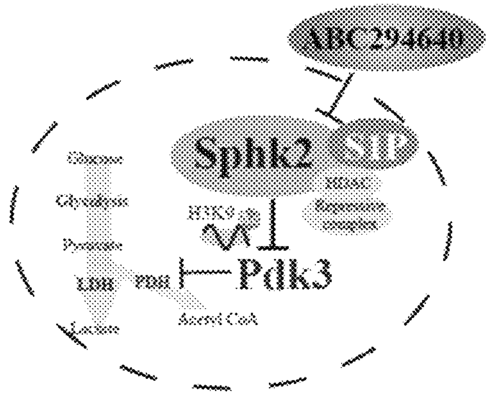
FIG. 13 is a scheme showing that Sphk2 upregulates Pdk3 expression and suppresses OXPHOS to protect HSCs from ROS generation.

These results indicate that increased HSPC function by Sphk2 attenuation is mediated by the upregulation of Pdk3, which reprogrammed the metabolic state and suppressed ROS level in HSPCs (FIG. 13).

Example 13 PDK3 Overexpression Promotes HSC Long-Term Function

Figure 89:
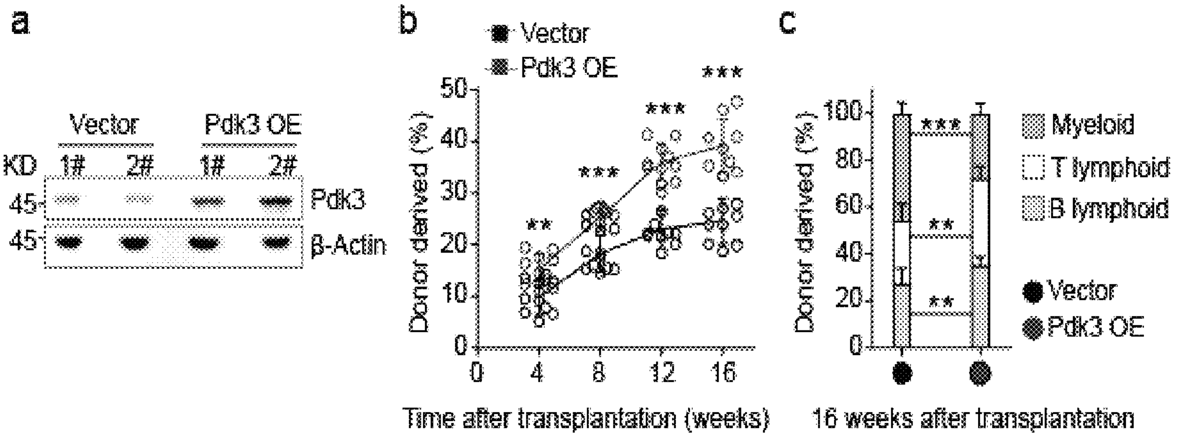
FIG. 89 shows PDK3 overexpression promotes HSC long-term function.

To investigate whether PDK3 overexpression in HSCs can stimulate HSC long-term function, retroviral system was employed to enhance the expression of PDK3 in HSCs (FIG. 89*a*), FIG. 89*a* represents western blot analyses of PDK3 protein in control HSCs and PDK3 overexpression HSCs, 1 #, and 2 # indicated two individual experiments). Next, PDK3 overexpressed HSCs and control HSCs were transplanted into lethally irradiated recipients with competitive bone marrow cells to evaluate the repopulation compacities of HSCs. Through the 16-week observation period, it was found that HSCs with enhanced PDK3 expression significantly gave high reconstitution (1.59-Fold increase at 16 weeks post transplantation) (FIG. 89*b*, FIG. 89*b* represents peripheral blood analysis for total engrafted donor cells at the indicated number of weeks after transplantation, n=10 mice each group. Data represent mean±s.d. Two-tailed Student's t-tests assessed statistical significance, $*P<0.05$, $P<0.01$, $*P<0.001$) and maintained the multilineage potential (FIG. 89*c*, FIG. 89*c* represents the percentage of donor-derived B, T and myeloid lineage cells at 16 weeks after transplantation, n=10 mice each group. Data represent mean±s.d. Two-tailed Student's t-tests assessed statistical significance, $*P<0.05$, $P<0.01$, $*P<0.001$).

Example 14 ABC294640 Promotes Human Cord Blood HSC Expansion

Figure 90:
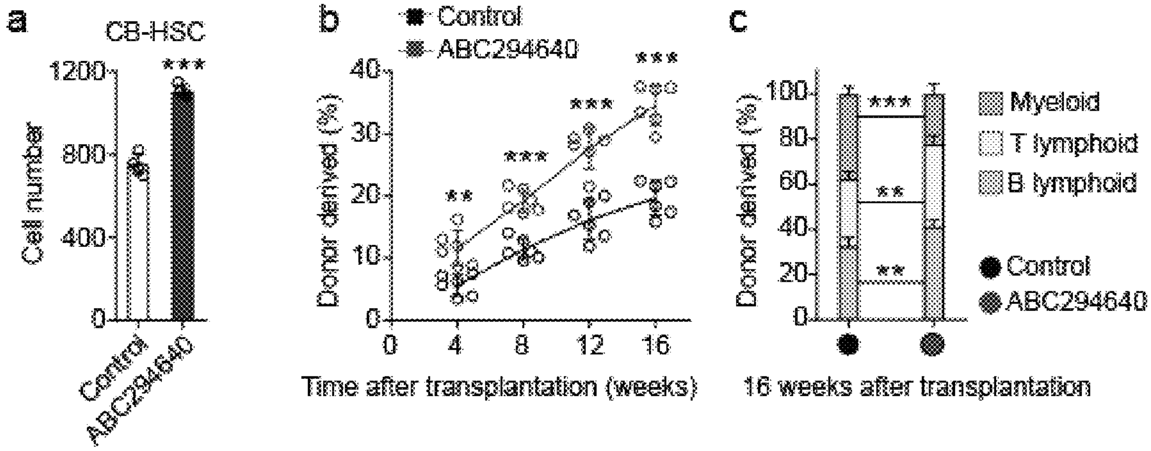
FIG. 90 shows Sphk2 inhibition promotes human cord blood HSC expansion.

To explore whether inhibition of Sphk2 by ABC294640 can expand human HSCs, total nuclear cells were subjected from human cord blood to ex vivo culture system with or without Sphk2 inhibitor ABC294640. After 2-week culture, it was found that ABC294640 treatment increased human HSC numbers (1.4 fold increase, FIG. 90*a*; FIG. 90*a* illustrates quantification of CB-HSCs with or without ABC294640 treatment, n=6 mice each group. Data represent mean±s.d. Two-tailed Student's t-tests assessed statistical significance, *P<0.05, P<0.01, *P<0.001). ABC294640 treated HSCs was further transplanted into immunodeficient NOD.Cg-Prkdcscid IL2rgtmWjl/SzJ (NSG) mice, and the reconstitution ability of human HSCs treatment by ABC294640 was evaluated. Through the 16-week observation period, it was found that ABC294640 treated HSCs significantly gave high reconstitution (1.76-Fold increase at 16 weeks post transplantation, FIG. 90*b*; FIG. 90*b* represents peripheral blood analysis for total engrafted donor cells at the indicated number of weeks after transplantation, n=6 mice each group. Data represent mean±s.d. Two-tailed Student's t-tests assessed statistical significance, *P<0.05, P<0.01, *P<0.001) with multi-lineage potential (FIG. 90*c*). More importantly, mice transplanted with ABC294640 treated HSCs presented improved lymphopoiesis (both B and T cells in recipients), and a reduction in myeloid skewing (FIG. 90*c*; FIG. 90*c* represents the percentage of donor-derived B, T and myeloid lineage cells at 16 weeks after transplantation, n=6 mice each group. Data represent mean±s.d. Two-tailed Student's t-tests assessed statistical significance, *P<0.05, P<0.01, *P<0.001). Aged HSCs, in the recipients, had reduced repopulation capacity and compromised lymphopoiesis. Inhibition of Sphk2 by ABC294640 significantly improved HSC repopulation capacity and increased lymphopoiesis (both B and T cells in recipients). Therefore, the above data supported that inhibition of Sphk2 prevents aging in human HSCs.

"comprise," "have," "include," and "contain," are intended to mean an open term (i.e., meaning "including, but not limited to"). Unless otherwise defined in the context, recitation of ranges of values as used herein are merely intended to serve as a shorthand of a plural of each individual value falling within the range as individually listed, and each individual value is incorporated in the specification as if it is individually listed herein. Unless otherwise stated herein or clearly contradictory to the context, all the methods as described herein can be performed in any suitable order. Unless otherwise defined in the claims, any and all examples or exemplary languages (e.g., "such as") as used herein are merely intended to illustrative, and not to limit the scope of the application. Any language in the specification should not be construed as indicating that any element which is not claimed in the claims is necessary to practice the application.

Exemplifying embodiments of the present application are described herein, including the mode known by the inventors for carrying out the application. Upon reading of the description, variations of those exemplified embodiments will be apparent to those of ordinary skill in the art.

The inventors expect that the skilled person can apply such variants if required, and the inventors intend to implement the present application in a manner other than those specifically described herein. Thus, the present application includes all the modifications and equivalents of the subject matter described in the appended claims as permitted by applicable laws. Moreover, the present application comprises any combination of all possible variations of the aforesaid elements, unless otherwise indicated or clearly contradict with the context.

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: siRNA against Pdk3

<400> SEQUENCE: 1

ggacctgcat catgaacaat g                                              21
```

All references as cited herein, including publications, patent applications and patents, are hereby incorporated by reference, as if it is individually and in particular stated that each of the references is incorporated by reference and to the extent that the reference is completely set forth herein.

In the context of the present application (especially in the context of the following claims, unless otherwise stated herein or clearly contradictory to the context, the terms "a" and "an" and "the" and "at least a/an/one" and similar referents are to be understood as comprising both singular and plural forms. Unless otherwise stated herein or clearly contradictory to the context, when the term "at least one" is followed by one or more of items as listed (for example, "at least one of A and B"), it is to be understood as one of the listed items (A or B) or any combination of two or more of the listed items (A and B). Unless otherwise noted, the terms

What is claimed:

1. A method for rejuvenating an aged HSPC, comprising: attenuating an expression and/or function of Sphk2 of said aged HSPC; and/or enhancing an expression and/or function of Pdk3 of said aged HSPC.

2. The method of claim 1, wherein said aged HSPC is obtained from an aged subject.

3. The method of claim 1, wherein said expression and/or function of said Sphk2 is attenuated by inhibiting an expression and/or function of the Sphk2 gene, and/or inhibiting an expression and/or function of the Sphk2 protein.

4. The method of claim 1, wherein said expression and/or function of said Sphk2 is attenuated with a Sphk2 inhibitor.

5. The method of claim 4, wherein said Sphk2 inhibitor comprises a compound of formula (I) or a pharmaceutically salt thereof:

(I)

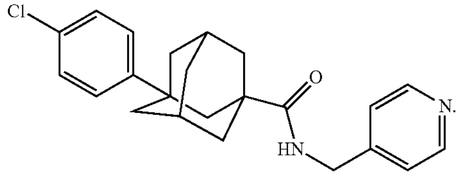

6. The method of claim 4, wherein said SphK2 inhibitor comprises a compound of formula (II) or a pharmaceutically acceptable salt thereof:

(II)

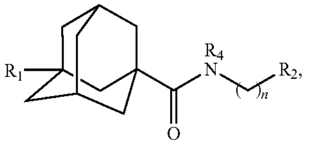

wherein:

$R_1$ s phenyl, or a phenyl substituted with a halogen;

$R_2$ is aryl, heteroaryl, or a substituted aryl or heteroaryl;

$R_4$ is H or alkyl; and n is an integer of at least 1.

7. The method of claim 2, wherein said subject has been subjected to chemotherapy.

8. The method of claim 2, wherein said subject has been subjected to bone marrow transplantation.

* * * * *